United States Patent
Barron et al.

(10) Patent No.: US 9,566,381 B2
(45) Date of Patent: Feb. 14, 2017

(54) DISPOSABLE FLUID CONNECTOR HAVING MULTIPLE TUBING COMPONENTS AND AN ELECTRICAL CONNECTOR

(75) Inventors: Traci Barron, St. John, IN (US); Niels Clausen-Stuck, London (GB); Mark Fisher, Highland Park, IL (US); Joseph Graceffa, Chicago, IL (US); David J. Hajicek, Minnetonka, MN (US); Martin G. Hieb, St. Louis Park, MN (US); Anastasios G. Karahalios, Skokie, IL (US); Karen Kensok, Minnetonka, MN (US); Robert Kim, Shoreview, MN (US); Lawrence Lunzer, St. Louis Park, MN (US); Manfred Maiers, Savage, MN (US); Adolfo Menendez, Jr., Woodbury, MN (US); Khader Mohiuddin, Plymouth, MN (US); Richard A. Oftedahl, Jordan, MN (US); Volker Roos, Unterfoehring (DE); Jeremiah O'Leary, Chicago, IL (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 1103 days.

(21) Appl. No.: 13/620,198

(22) Filed: Sep. 14, 2012

(65) Prior Publication Data

US 2013/0053692 A1    Feb. 28, 2013

Related U.S. Application Data

(63) Continuation of application No. 12/094,009, filed as application No. PCT/US2006/060983 on Nov. 16, 2006, now Pat. No. 9,259,526.

(Continued)

(51) Int. Cl.
*A61M 5/00* (2006.01)
*A61M 5/142* (2006.01)
(Continued)

(52) U.S. Cl.
CPC ........... *A61M 5/007* (2013.01); *A61M 5/1452* (2013.01); *A61M 5/14216* (2013.01);
(Continued)

(58) Field of Classification Search
CPC ........... A61B 6/548; A61M 2005/1403; A61M 5/007; A61M 5/14216; A61M 5/1452; A61M 5/16809; A61M 5/16827; A61M 5/36; A61M 5/365; G06F 19/3406
See application file for complete search history.

(56) References Cited

U.S. PATENT DOCUMENTS 4,950,245 A    8/1990   Brown et al.
5,252,044 A    10/1993  Raines et al.
(Continued)

FOREIGN PATENT DOCUMENTS

CN    1145812 A    3/1997
CN    1431918 A    7/2003
(Continued)

OTHER PUBLICATIONS

English translation of the substantive content of Japanese office action for Japanese Patent Application No. 2011-288211, dated Mar. 18, 2013, entitled "Reasons, Japanese Patent Appln. No. 2011-288211," 4 pages.
(Continued)

*Primary Examiner* — Amanda Lauritzen Moher
(74) *Attorney, Agent, or Firm* — Shumaker & Sieffert, P.A.

(57) ABSTRACT

A disposable fluid connector includes a first single-use tubing component having proximal and distal ends and a
(Continued)

second single-use tubing component having proximal and distal ends, where the first single-use tubing component and the second single-use tubing component are each usable only for a single patient procedure. The disposable fluid connector also includes a connection comprising an electrical connector that is configured to electrically connect the connection to both a powered injector and to an external medical device, where the disposable fluid connector comprises a disposable cassette including a portion that is non-removably attached to both the first single-use tubing component and the second single-use tubing component.

4 Claims, 56 Drawing Sheets

Related U.S. Application Data

(60) Provisional application No. 60/738,829, filed on Nov. 21, 2005.

(51) Int. Cl.
| | | |
|---|---|---|
| *A61M 5/145* | (2006.01) | |
| *G06F 19/00* | (2011.01) | |
| *A61B 6/00* | (2006.01) | |
| *A61M 5/168* | (2006.01) | |
| *A61M 5/36* | (2006.01) | |
| *A61M 5/14* | (2006.01) | |

(52) U.S. Cl.
CPC ........ *A61M 5/16827* (2013.01); *A61M 5/365* (2013.01); *G06F 19/3406* (2013.01); *A61B 6/481* (2013.01); *A61B 6/504* (2013.01); *A61B 6/548* (2013.01); *A61M 5/16809* (2013.01); *A61M 5/36* (2013.01); *A61M 2005/1403* (2013.01)

(56) References Cited

U.S. PATENT DOCUMENTS

| | | | |
|---|---|---|---|
| 5,254,096 | A | 10/1993 | Rondelet et al. |
| 5,330,431 | A | 7/1994 | Herskowitz |
| 6,361,518 | B1 | 3/2002 | Brierton et al. |
| 6,626,862 | B1 | 9/2003 | Duchon et al. |
| 6,692,241 | B2 | 2/2004 | Watanabe |
| 7,128,729 | B2 | 10/2006 | Duchon et al. |
| 7,169,135 | B2 | 1/2007 | Duchon et al. |
| 7,470,261 | B2 | 12/2008 | Lynn |
| 7,566,320 | B2 | 7/2009 | Duchon et al. |
| 7,662,124 | B2 | 2/2010 | Duchon et al. |
| 8,463,362 | B2* | 6/2013 | Fago .................. A61M 5/1413 600/420 |
| 8,571,881 | B2* | 10/2013 | Rousso ................. A61B 5/417 600/431 |
| 8,628,514 | B2* | 1/2014 | Fago .................... A61M 5/007 137/557 |
| 9,265,885 | B2* | 2/2016 | Strobl .................. A61M 5/007 |
| 2002/0016569 | A1* | 2/2002 | Critchlow et al. ........... 604/131 |
| 2002/0085952 | A1 | 7/2002 | Ellingboe et al. |
| 2002/0115933 | A1 | 8/2002 | Duchon et al. |
| 2002/0198496 | A1 | 12/2002 | Duchon et al. |
| 2003/0018252 | A1 | 1/2003 | Duchon et al. |
| 2003/0030011 | A1* | 2/2003 | Brown et al. ............ 250/455.11 |
| 2003/0216692 | A1* | 11/2003 | Fago .................. A61M 31/005 604/150 |
| 2003/0231990 | A1* | 12/2003 | Faries, Jr. ............. A61B 46/00 422/119 |
| 2004/0031756 | A1 | 2/2004 | Suzuki et al. |
| 2004/0073161 | A1 | 4/2004 | Tachibana |
| 2004/0084358 | A1 | 5/2004 | O'Mahony |
| 2004/0143185 | A1 | 7/2004 | Zatezalo et al. |
| 2004/0143212 | A1 | 7/2004 | Trombley, III et al. |
| 2004/0254525 | A1* | 12/2004 | Uber, III ............... A61M 5/007 604/67 |
| 2005/0029277 | A1 | 2/2005 | Tachibana |
| 2005/0230575 | A1 | 10/2005 | Zelenski et al. |
| 2009/0149743 | A1 | 6/2009 | Barron et al. |
| 2012/0030610 | A1 | 2/2012 | Diperna et al. |

FOREIGN PATENT DOCUMENTS

| | | |
|---|---|---|
| EP | 0340427 A2 | 11/1989 |
| EP | 0589328 A2 | 3/1994 |
| JP | 6-190037 | 7/1994 |
| JP | H06190037 A | 7/1994 |
| JP | 2002210007 A | 7/2002 |
| JP | 2005/013413 A | 1/2005 |
| WO | 9924095 A2 | 5/1999 |
| WO | 2004/006994 A1 | 1/2004 |
| WO | 2004004802 A2 | 1/2004 |
| WO | 2004006994 A1 | 1/2004 |
| WO | 2004/014267 A1 | 2/2004 |
| WO | 2004014267 A1 | 2/2004 |
| WO | 2005031628 A2 | 4/2005 |

OTHER PUBLICATIONS

Machine translation of important content of Japanese publication No. 03-292964, dated Dec. 24, 1991, 1 page.
Machine translation of important content of Japanese publication No. 2002-210007, dated Jul. 30, 2002, 6 pages.
Machine translation of important content of Japanese publication No. 62-84435, dated May 29, 1987, 1 page.
Communication pursuant to Article 94(3) EPC for corresponding European application No. 12 160411.0-2320, dated Feb. 8, 2013, 3 pages.
U.S. Appl. No. 13/620,068, filed Sep. 14, 2012.
U.S. Appl. No. 13/620,123, filed Sep. 14, 2012.
Response to European Office Action dated Oct. 8, 2014, from European Application No. 12 160 411.0-1662, filed on Feb. 13, 2015, 48 pp.
Notice of Allowance from counterpart Korean Patent Application No. 10-2013-7022835, dated Jul. 1, 2014, 4 pp.
Response to European Patent Application dated Oct. 21, 2013, from European Patent Application No. 12160411.0-1662, filed Apr. 28, 2014, 9 pp.
Office action for U.S. Appl. No. 12/094,009, mailed Jun. 21, 2013, 14 pages.
Response to office action for U.S. Appl. No. 12/094,009, filed Mar. 8, 2013, 14 pages.
Response to the communication under Rule 70(2) and Rule 70a(2) EPC for patent application No. 12160411.0, dated Dec. 20, 2012, 7 pages.
Office action for U.S. Appl. No. 12/094,009, mailed Dec. 13, 2012, 8 pages.
Response to Final Office Action mailed Jun. 21, 2013, from U.S. Appl. No. 12/094,009, filed Sep. 19, 2013, 16 pp.
Response to Office Action dated Apr. 12, 2013, from European patent application No. 12160420.1-1952, filed Aug. 20, 2013, 5 pp.
Communication pursuant to Article 94(3) EPC for European Patent Application No. 12 160 411.0-1662, dated Oct. 21, 2013, 3 pages.
Office Action and English translation thereof for Korean patent application No. 10-2013-7022835, dated Dec. 23, 2013, 7 pages.
Examination Report from Counterpart European Patent Application No. 12160411.0, dated Oct. 8, 2014, 4 pp.
Office Action from corresponding Chinese Application No. 201310150127.7, dated Feb. 2, 2015, 11 pp.
Third Office Action and translation thereof counterpart Chinese Application No. 201310150127.7, dated Apr. 21, 2016, 14 pp.
Second Office Action and English Translation from counterpart Chinese Patent Application No. 201310150127.7, dated Oct. 14, 2015, 13 pp.
Extended European Search Report from European application No. 12160418.5, dated May 29, 2012, 6 pp.

(56) References Cited

OTHER PUBLICATIONS

Extended European Search Report from European application No. 12160411.0, dated May 29, 2012, 5 pp.
Extended European Search Report from European application No. 12160415.1, dated May 25, 2012, 7 pp.
Extended European Search Report from European application No. 12160420.1, dated May 25, 2012, 8 pp.
Office Action from Chinese patent application No. 200680050825.8, dated Jul. 13, 2012, 6 pp.
Communication from European associate regarding responding to the communication dated Mar. 22, 2010, under Article 94(3) EPC, filed with the European Patent Office for European Patent Application No. 06846325.6, dated Sep. 30, 2010, 7 pp.
Communication from Japanese associate regarding Official Action from JPO for Japanese Patent Application No. 2008-542502, dated Aug. 9, 2011, 4 pp.
Supplementary European Search Report from European application No. 06846325, dated Jan. 28, 2010, 9 pp.

* cited by examiner

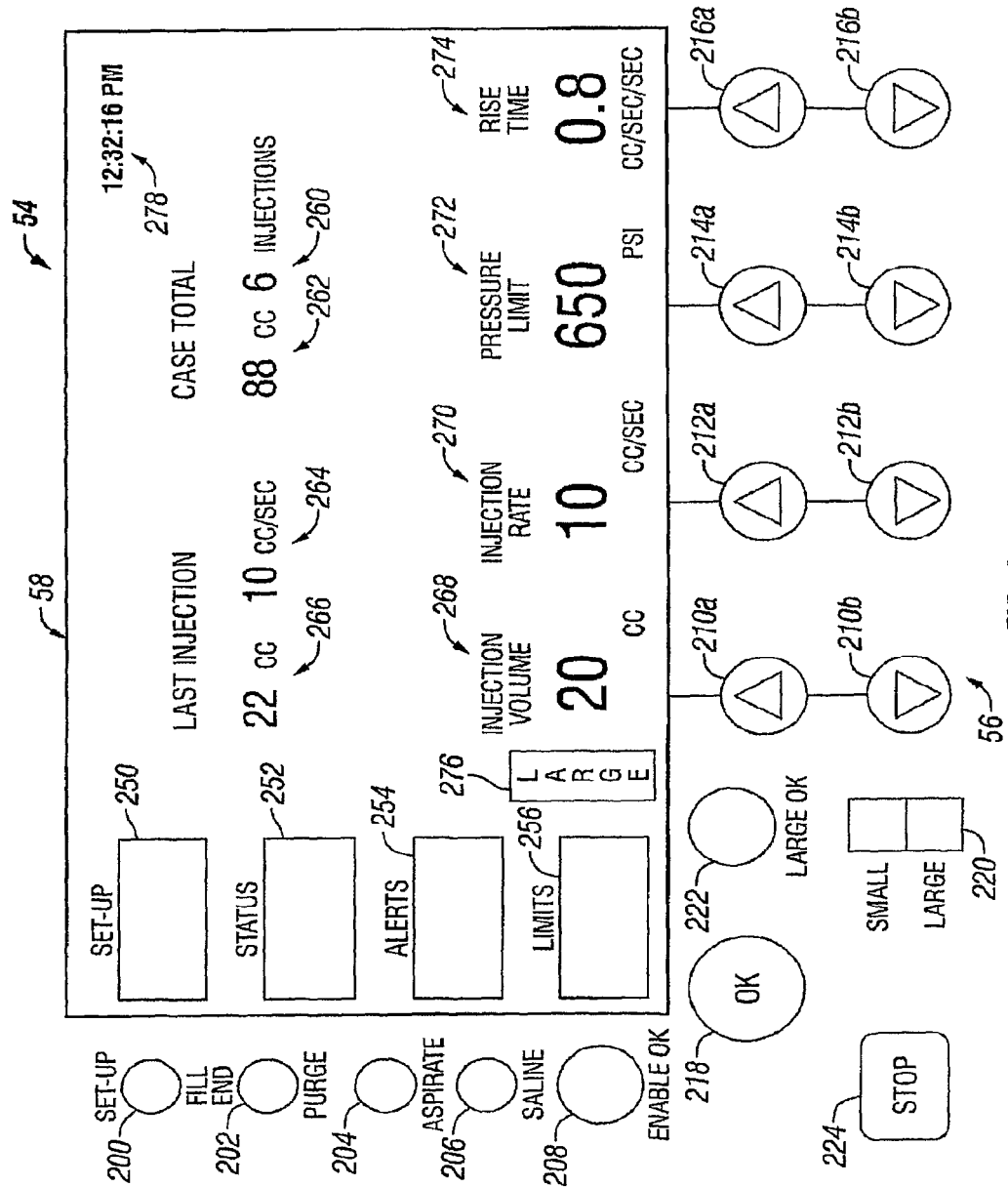

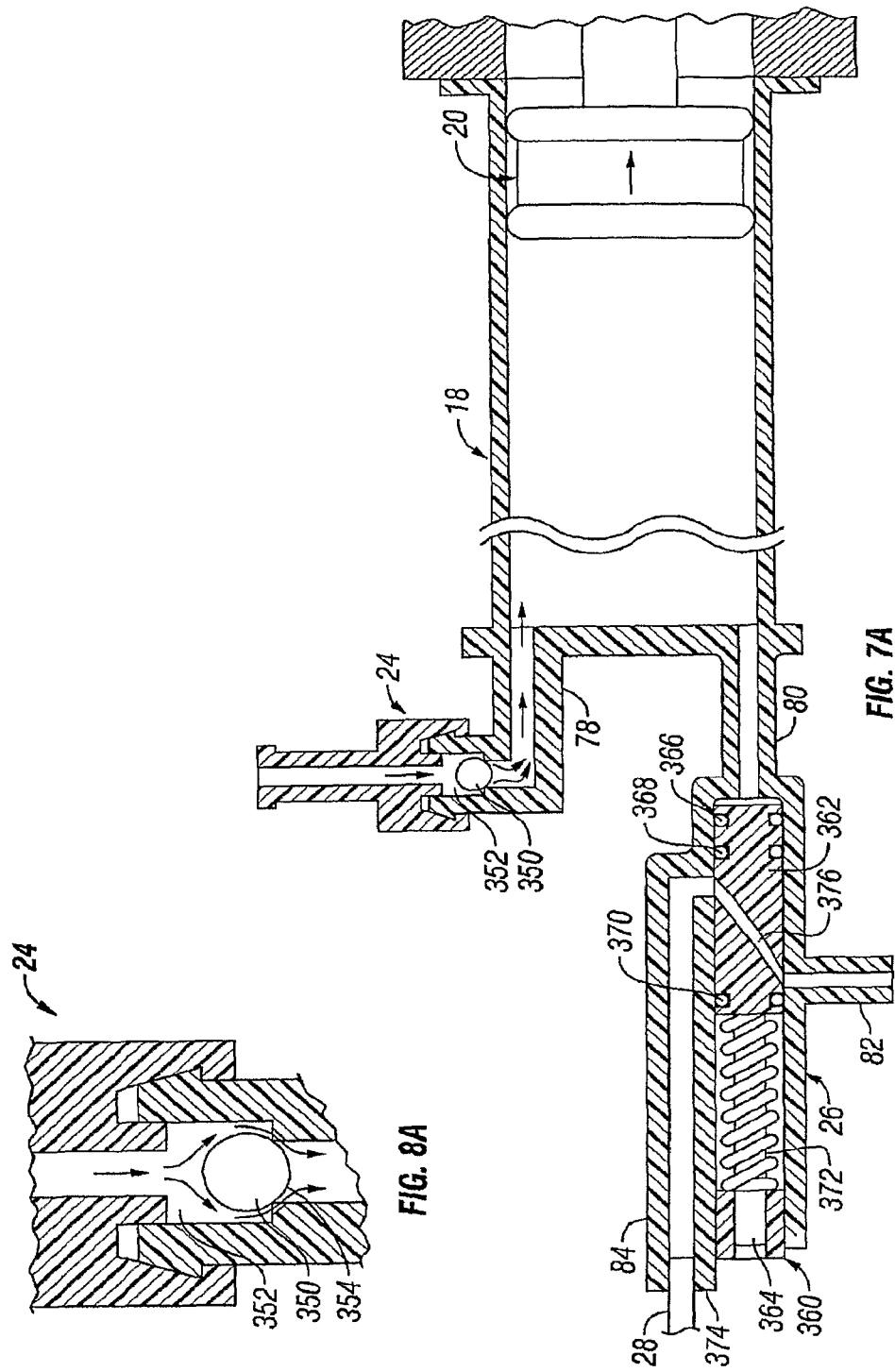

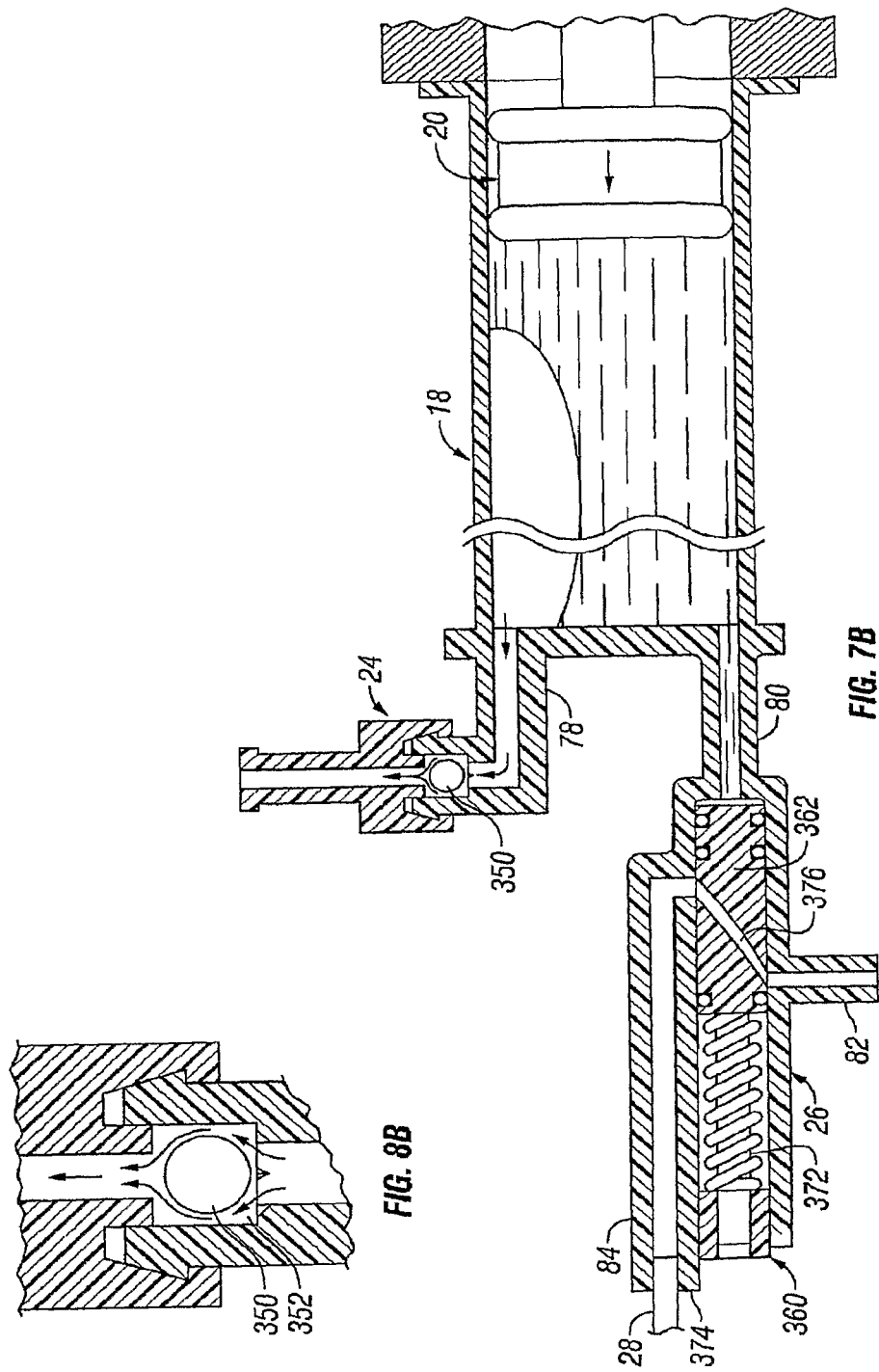

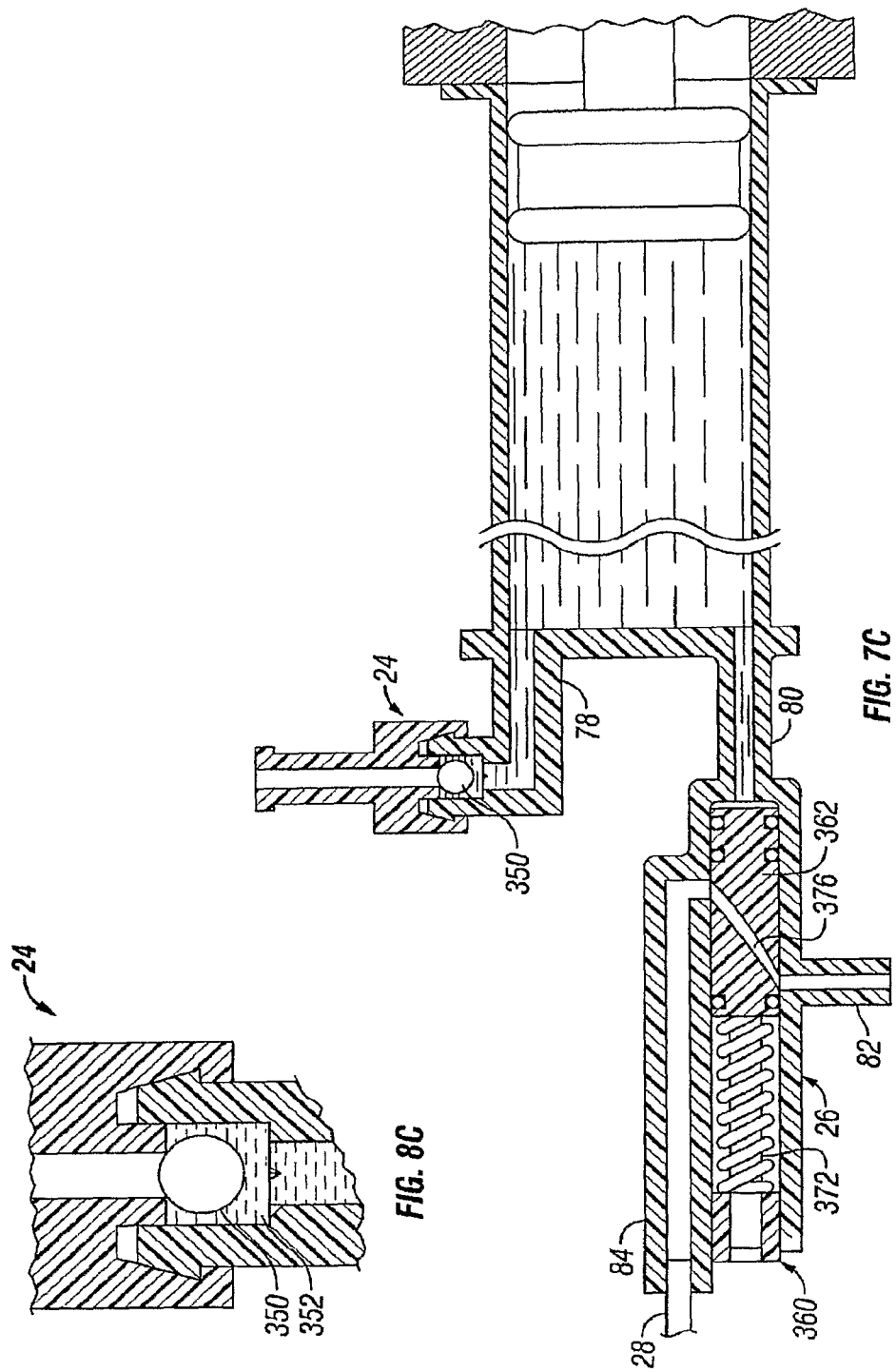

| LEFT CORONARY | | | FIXED | SELECT INJECTION |
|---|---|---|---|---|
| FLOW RATE | VOLUME | PRESSURE | RISE TIME | ⊘ LCA |
| | 13.0 | 625 | 0.2 | ○ RCA |
| | mL | PSI | sec | ○ LV/Ao |

| 7 8 9 Back | INDICATORS | SELECT MODE |
|---|---|---|
| 4 5 6 ENTER | | ○ INJECT |
| 1 2 3 0 | | ○ SALINE |
| | | ○ ASPIRATE |
| | | ○ PURGE |

| CONTRAST TOTAL: 0mL   PATIENT WEIGHT: 110.0 Kgs | ACIST 3.1.0 |
|---|---|
| LAST INJECTION: 0.0mL @ 0.0mL/s | |
| FIXED RATE    AUTO-REFILL | ○ END CASE |

FIG. 32

| LEFT CORONARY | | | | SELECT INJECTION |
|---|---|---|---|---|
| FLOW RATE | VOLUME | PRESSURE | RISE TIME | ⊘ LCA |
| | 13 | 625 | 0.2 | ○ RCA |
| | mL | PSI | sec | ○ LV/Ao |

| Press the desired Flow Rate (mL/s) | INDICATORS | SELECT MODE |
|---|---|---|
| 1 2 4 6 8 10 CANCEL | | ○ INJECT |
| | | ○ SALINE |
| | | ○ ASPIRATE |
| | | ○ PURGE |

| CONTRAST TOTAL: 0mL   PATIENT WIEGHT: 110.0 Kgs | ACIST 3.1.0 |
|---|---|
| LAST INJECTION: 0.0mL @ 0.0mL/s | |
| VARIABLE RATE    AUTO-REFILL | ○ END CASE |

DISPOSABLE FLUID CONNECTOR HAVING MULTIPLE TUBING COMPONENTS AND AN ELECTRICAL CONNECTOR

RELATED APPLICATIONS

This application is a continuation of U.S. application Ser. No. 12/094,009 filed Nov. 20, 2008, which is the national stage filing of corresponding international application number PCT/US2006/060983, filed Nov. 16, 2006, which claims priority to and the benefit of U.S. Provisional Application No. 60/738,829 filed Nov. 21, 2005, all of which are hereby incorporated by reference.

FIELD OF THE INVENTION

This application relates generally to an improved injector system for injecting medical fluids, such as radiographic contrast fluids, particularly for angiography.

BACKGROUND OF THE INVENTION

Angiography is a procedure used in the diagnosis and treatment of cardiovascular conditions including abnormalities or restrictions in blood vessels, the network of passageways through which blood travels in a human or animal body. During angiography, a radiographic contrast material is injected through a catheter into a vein or artery, which then passes to vascular structures in fluid communication with the vein or artery. When X-rays are passed through the region of the body into which the contrast material is injected, they are absorbed by the contrast material, providing radiographic images of the desired vascular structure(s). The images can be recorded on film or video tape and/or displayed on a fluoroscope monitor. The images can be used for many purposes, as for example, diagnostics and for therapeutic procedures such as angioplasty, wherein a balloon is inserted into a vascular system and inflated to open a stenosis.

The contrast material can be injected into the catheter by either manual or automated injection systems. While the apparatus for injecting the contrast material can vary, most current systems include a syringe operatively connected with the catheter. The syringe has a chamber for holding the contrast material and a plunger reciprocally moveable within the chamber. The contrast material is suctioned into the chamber when the plunger is moved to create a partial vacuum within the chamber. A reversal of the plunger direction first forces air out of the chamber and then delivers the contrast material to the catheter at a rate and volume determined by the speed of movement of the plunger.

In a manual system the user or operator loads the syringe and ejects air from the chamber before connecting the syringe to the catheter. The user of a manual system adjusts the rate and volume of injection by altering the manual force applied to the plunger. The maximum injection pressure for manual systems is typically limited to about 150 p.s.i. (i.e. the maximum pressure that can be applied by the human hand), and the maximum quantity of fluid is about 12 cc. Such manual systems typically do not accommodate any safety features such as the restriction or prevention of injections outside of predetermined injection parameters (such as rate or pressure), and generally do not include active sensors or alarms to detect air bubbles or other hazards.

Angiography can include the injection of fluids other than the contrast material. For example, a saline flush and/or the injection of fluid medications may be desired. One of the most commonly used manual injection systems includes a valve mechanism having a plurality of manually activated valves that the operator selectively opens and closes to direct flow of the desired fluids into or out of fluid channels connected to the syringe or catheter. When the operator aspirates or injects the contrast fluid into or out of the syringe chamber, the fluid flows through the path of least resistance as directed by the relative positions of the valves. When changing the valve positions, one or more fluids may be selectively injected.

Certain automated fluid delivery systems provide a control panel or user interface that may be used, or operated, by a trained professional, such as a physician. The professional may enter one or more injection parameters using the control panel. The user interface may comprise a touch-panel screen. These parameters can then be used during a patient injection procedure. Certain automated injection systems require entry of the following injection parameters: the volume of contrast material to be injected, the flow rate of injection, the maximum permitted injection pressure and the rate of change of injection flow rate (i.e. the rise time). The control panel may be connected directly to an injector head or to a patient bed table.

SUMMARY OF THE INVENTION

According to certain embodiments, there is provided an injection system having a dual-syringe assembly. One syringe is capable of holding a first fluid medium (such as contrast), and the second syringe is capable of holding a second fluid medium (such as saline). Each syringe comprises independent inlet and outlet ports. The inlet port is used to fill the syringe with fluid, and the outlet port is used to expel fluid from the syringe.

According to certain embodiments, there is provided an injection system that uses a disposable cassette providing fluid connections to the injection system. Fluid that is dispensed by the injection system is provided to the patient via the disposable cassette. One or more tubing components are coupled between the injection system and the disposable cassette. Valves, and particularly pinch valves, may be used to prevent flow of fluid to the disposable cassette in certain scenarios, and to also prevent backflow of fluid. The disposable cassette provides fluid connections between the cassette and the injection system, and also provides connections for tubing that may be connected to the patient. The disposable cassette may be a single-use component that is discarded after each patient use.

According to certain embodiments, there is provided an injection system that provides multiple display devices. In this aspect, a small display device may be provided directly on the injector, while a larger display device (main control panel) may be located remotely from the small display device. The small display device may be used to provide setup information, error and troubleshooting information, and other system information, and it may also be used to obtain certain input from the user, such as bottle or bag size. In one aspect, there is further provided an additional remote display that may be the size of a personal digital assistant (PDA). This additional remote display may be in communication with the main control panel via a wireless connection, according to one embodiment. A physician may utilize this additional remote display with flexibility, because the display is mobile. Due to its size, the additional display is also very portable and convenient to use. In one implementation, the additional display provides both user input capabilities and display output capabilities.

According to certain embodiments, there is provided an injection system that implements a method for using contextual lighting to assist a user of a fluid injection system. In these embodiments, the method comprises providing a first visual indicator on the fluid injection system instructing the user to perform a setup function on the system, providing a second visual indicator on the system if the user has improperly performed the setup function, and providing a third visual indicator on the system if the user has properly performed the setup function.

According to certain embodiments, there is provided an injection system having an improved graphical user interface (GUI) for display within a display device in the system. One aspect also provides customizable area injection buttons, icons for fast navigation, and a range of predefined icons. In some embodiments, the GUI provides an interface for the user during either guided or express setup modes of the system. In these embodiments, the functionality of the GUI may be synchronized with one or more aspects of the contextual lighting. Various other items in the GUT provide an improved interface with the user.

The details of one or more embodiments of the invention are set forth in the accompanying drawings and the description below. Other features, objects, and advantages will be apparent from the description and drawings, and from the claims.

BRIEF DESCRIPTION OF THE DRAWINGS

FIG. 4 illustrates front panel controls and displays of a preferred embodiment of the injector system.

FIGS. 7A-7D illustrate the operation of the inlet check valve and manifold during contrast fill, air purge, and patient inject operations.

FIGS. 8A-8C illustrate operation of the inlet check valve in greater detail.

FIG. 32 is an illustration of the MAIN display screen of FIG. 30 illustrating the keypad that is displayed when the Fixed Rate mode of operation is selected.

FIG. 33 is an illustration of the MAIN display screen of FIG. 30 illustrating the keypad that is displayed when the Variable Rate mode of operation is selected.

FIG. 34 is an illustration of the MAIN display screen of FIG. 30, illustrating operation in a Manual Purging mode.

FIG. 35 is an illustration of the MAIN display screen of FIG. 30, illustrating operation in a Manual Refilling mode.

DETAILED DESCRIPTION

Figure 1:
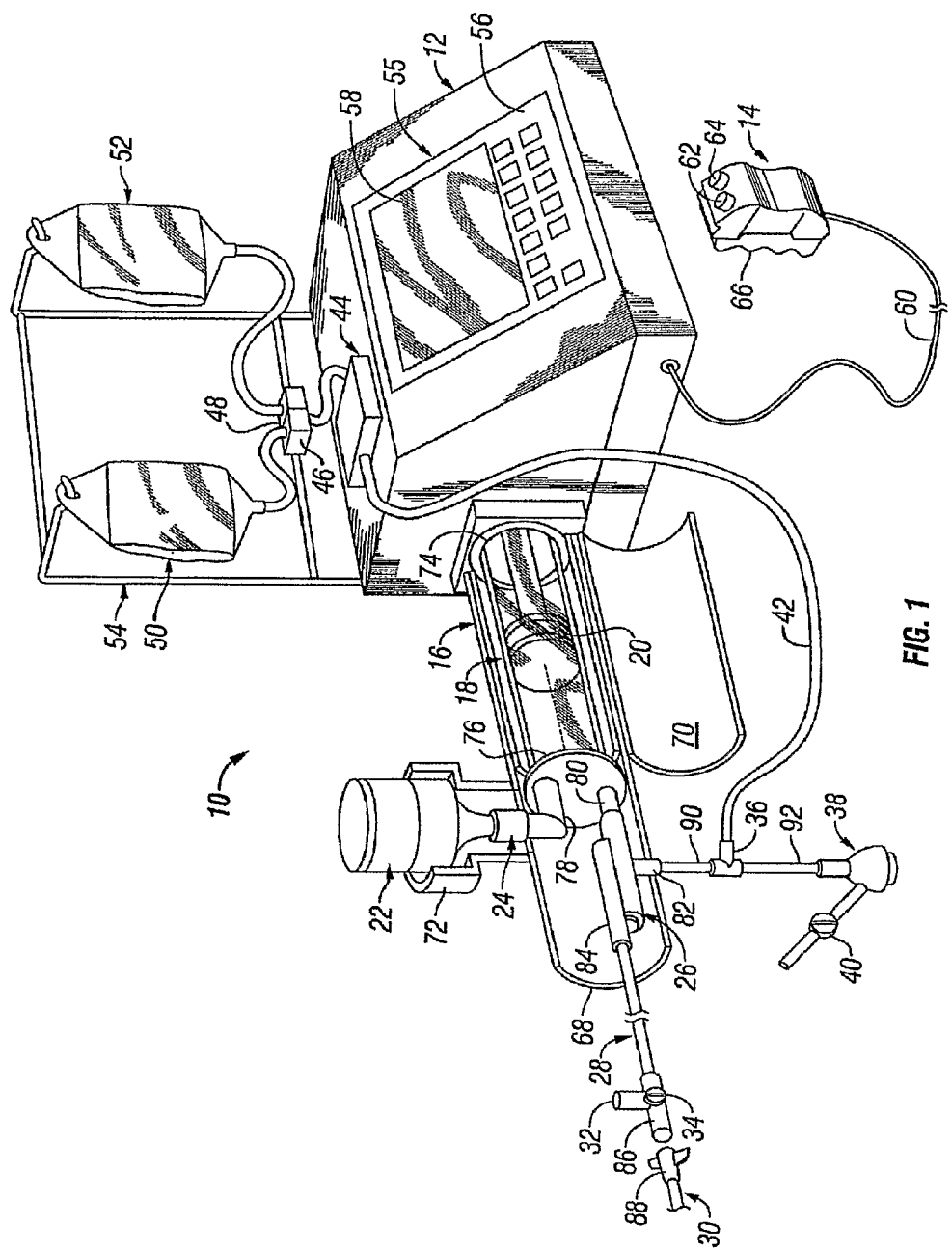
FIG. 1 is a perspective view illustrating a preferred embodiment of an angiographic injector system.

As will be appreciated upon a more detailed description herein, the principles of various embodiments of this invention can be applied to many different physical configurations of automated injector systems. Example of such systems will be generally described below. Referring to the Drawings, FIG. 1 shows an injector system 10 for injecting radiographic contrast material into a blood vessel under interactive physician control. System 10 includes main console 12, hand held remote control 14, syringe holder 16, syringe body 18, syringe plunger 20, radiographic material reservoir (bottle) 22, one-way valve 24, manifold 26, high pressure tube 28, catheter 30, patient medication port 32, three-way stop-cock 34, T-connector 36, pressure transducer 38, stop-cock 40, tubing 42, peristaltic pump 44, saline check valve 46, waste check valve 48, saline bag 50, waste bag 52, and bag support rack 54.

Console 12 houses the electrical controls for system 10, together with the motors which drive piston 20 and peristaltic pump 44. On the front surface of console 12, user interface 55 provides control switches 56 and display 58 through which the user may enter control settings and monitor the operational state of system 10. The console can be free-standing, preferably configured for mounting on a transport cart assembly.

Electrical power is provided to all electrical components of the system by an appropriate power supply which also provides electrical safety isolation from the main power source. The power supply can be located within the console 12, but is preferably mounted separately therefrom either on a wall or on a mounting cart.

Remote control 14 is connected to console 12 by cable 60 (although in other embodiments remote control 14 may be connected by a wireless connection such as an RF, infrared optic, or ultrasonic link). Remote control 14 is, in the embodiment shown in FIG. 1, a hand-held control which includes reset and saline push button switches 62 and 64, respectively, and flow rate control lever or trigger 66. By squeezing trigger 66, the user can provide a command signal to console 12 to provide a continuously variable injection rate.

Syringe holder 16 projects from the left hand side of console 12. Syringe holder 16 is preferably a clear material, and includes a half cylindrical back shell 68, a half cylindrical front door 70 (which is shown in open position in FIG. 1), and reservoir holder 72.

Syringe 18 is a transparent or translucent plastic cylinder having its open end 74 connected to console 12. Closed end 76 of syringe 18 contains two ports: upper port 78 and lower port 80.

Plunger 20 is movable within syringe body 18. Plunger 20 is connected to, and driven by a motor located within console 12.

Radiographic contrast material reservoir 22 is connected through one-way check valve 24 to upper port 78. Radiographic contrast material is drawn from reservoir 22 through check valve 24 and upper port 78 into the pumping chamber defined by syringe body 18 and plunger 20. Check valve 24 is preferably a weighted one-way valve which permits air to flow from syringe body 18 back into reservoir 22, but will not permit radiographic contrast material to flow from syringe body 18 to reservoir 22. This permits automatic purging of air from the system, as will be described in more detail later.

Lower port 80 of syringe body 18 is connected to manifold 26. Manifold 26 includes a spring biased spool valve which normally connects transducer/saline port 82 and patient port 84. When radiographic contrast material is to be injected, the pressure of the radiographic material causes the spool valve to change states so that lower port 80 is connected to patient port 84.

High pressure tube 28 is a flexible tube which connects patient port 84 to catheter 30. Three-way stop-cock 34 is located at the distal end of tube 28. Rotatable luer lock connector 86 is connected to stop-cock 34 and mates with luer connector 88 at the proximal end of catheter 30. Stopcock 34 either blocks flow between tube 28 and catheter 30, permits flow, or connects medication port 32 to catheter 30.

In addition to injecting radiographic material into a patient through catheter 30, system 10 also permits other related functions to be performed. A device for delivering the patient medication (not shown in FIG. 1) may be connected to medication port 32 when medication is to be delivered through catheter 30 to the patient.

When catheter 30 is in place in the patient, and an injection of radiographic contrast material is not taking place, pressure transducer 38 monitors the blood pressure through the column of fluid which extends from catheter 30, tube 28, patient port 84, manifold 26, transducer/saline port 82, tubing 90, T-connector 36, and tubing 92. Transducer 38 has an associated stop-cock 40 which allows transducer 38 to be exposed to atmospheric pressure during calibration and also allows for removal/expulsion of trapped air so the dome chamber of transducer 38 can be flushed with saline.

Peristaltic pump 44 supplies saline solution from bag 50 through saline check valve 46, tubing 42, T-connector 36 and tubing 90 to saline port 82. When peristaltic pump 44 is operating to supply saline solution, the saline solution is supplied through manifold 26 to patient port 84 and then through tube 28 to catheter 30.

Peristaltic pump 44 also operates in an opposite direction to draw fluid from catheter 30 and through tube 28, manifold 26, tubing 90, T-connector 36 and tubing 42 to waste check valve 48 and then into waste collection bag 52.

In a preferred embodiment of the present invention, syringe body 18, manifold 26, tube 28, catheter 30, T-connector 36, tubing 42, check valves 46 and 48, bags 50 and 52, and tubing 90 and 92 are all disposable items. They must be installed in system 10 each time an angiography procedure is to be performed with a new patient. Once system 10 is set up with all the disposable items installed, door 70 is closed, and syringe body 18 filled with contrast material and purged of air, the user (typically a physician) enters into system 10 the safety parameters that will apply to the injection of radiographic contrast material. These safety parameters typically include the maximum amount of radiographic contrast material to be injected during any one injection, the maximum flow rate of the injection, the maximum pressure developed within syringe body 18, and the maximum rise time or acceleration of the injection. To actuate an injection of contrast material, the user operates remote control 14 by squeezing trigger 66. Within the preset safety parameters, system 10 causes the flow rate of the injection to increase as the force or distance of travel of trigger 66 is increased.

Typically, the user will meter the amount and rate of contrast material injected based upon continuous observation of the contrast outflow into the structure being injected using fluoroscopy or other imaging methods. System 10 allows the user to tailor the contrast injections to the needs of the patient, thereby maximizing the quality of the procedure, increasing the safety, and reducing the amount of contrast material required to perform the fluoroscopic examination.

Figure 2A:
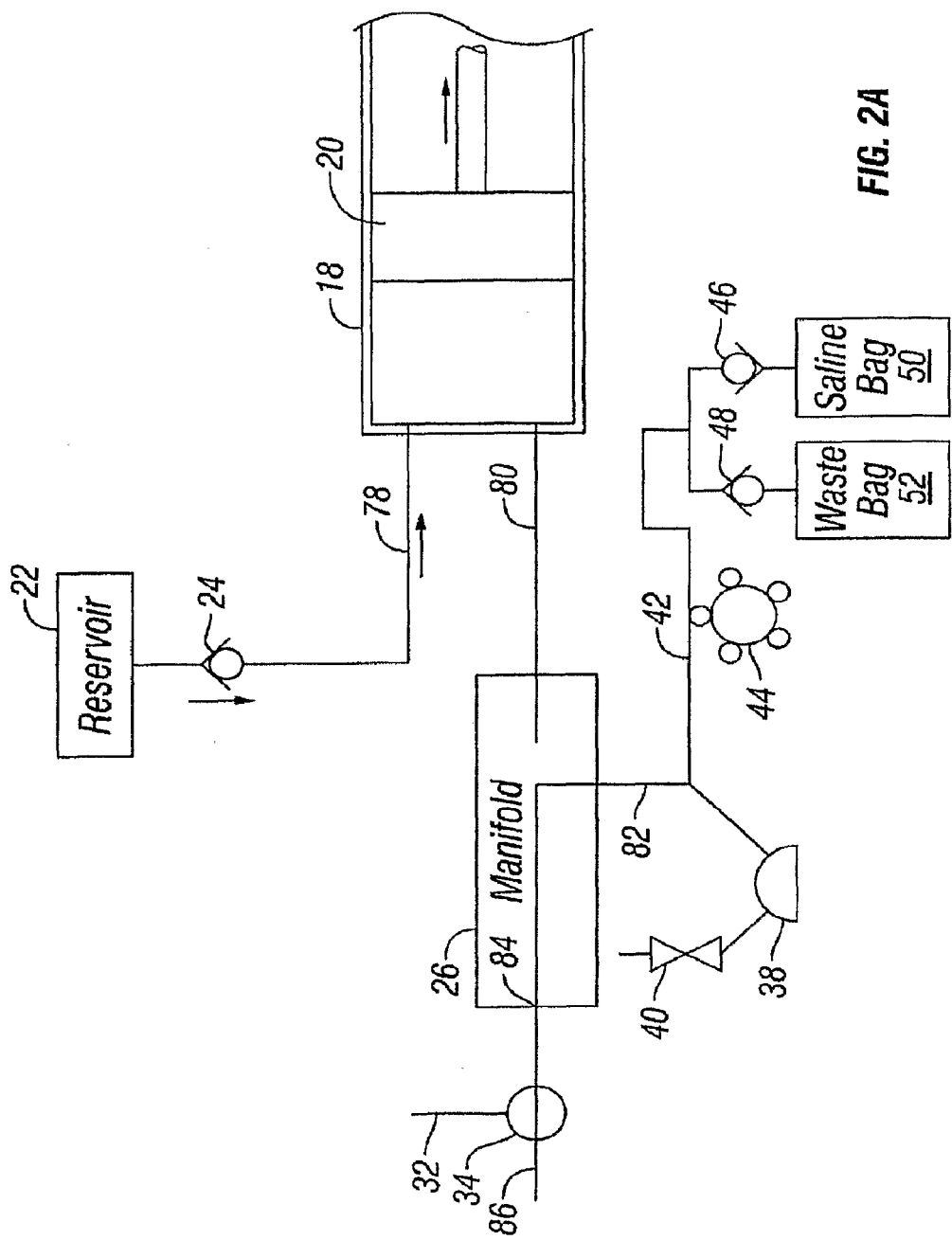
FIGS. 2A-2G are diagrams illustrating operations of the system of FIG. 1.
Figure 2B:
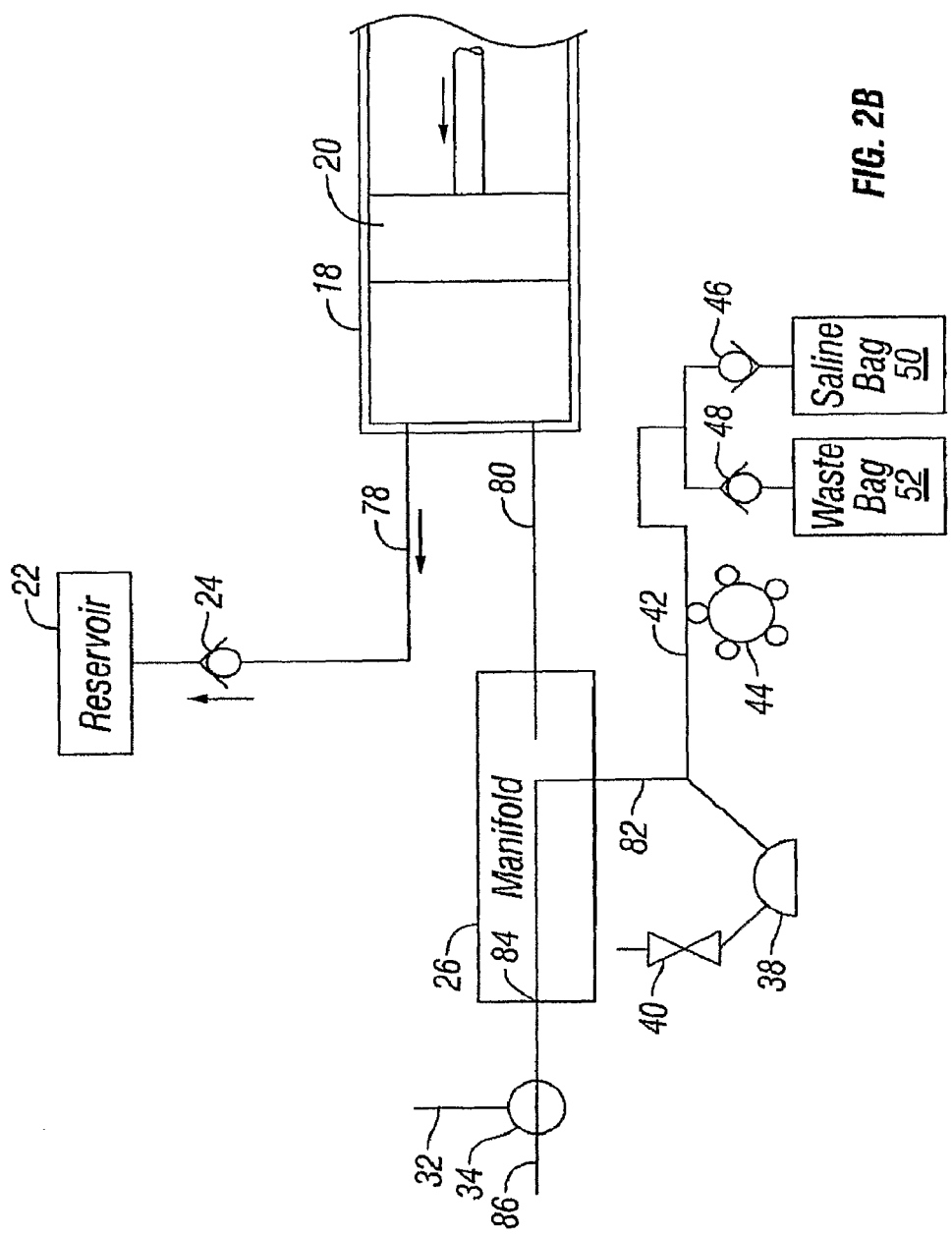
Figure 2C:
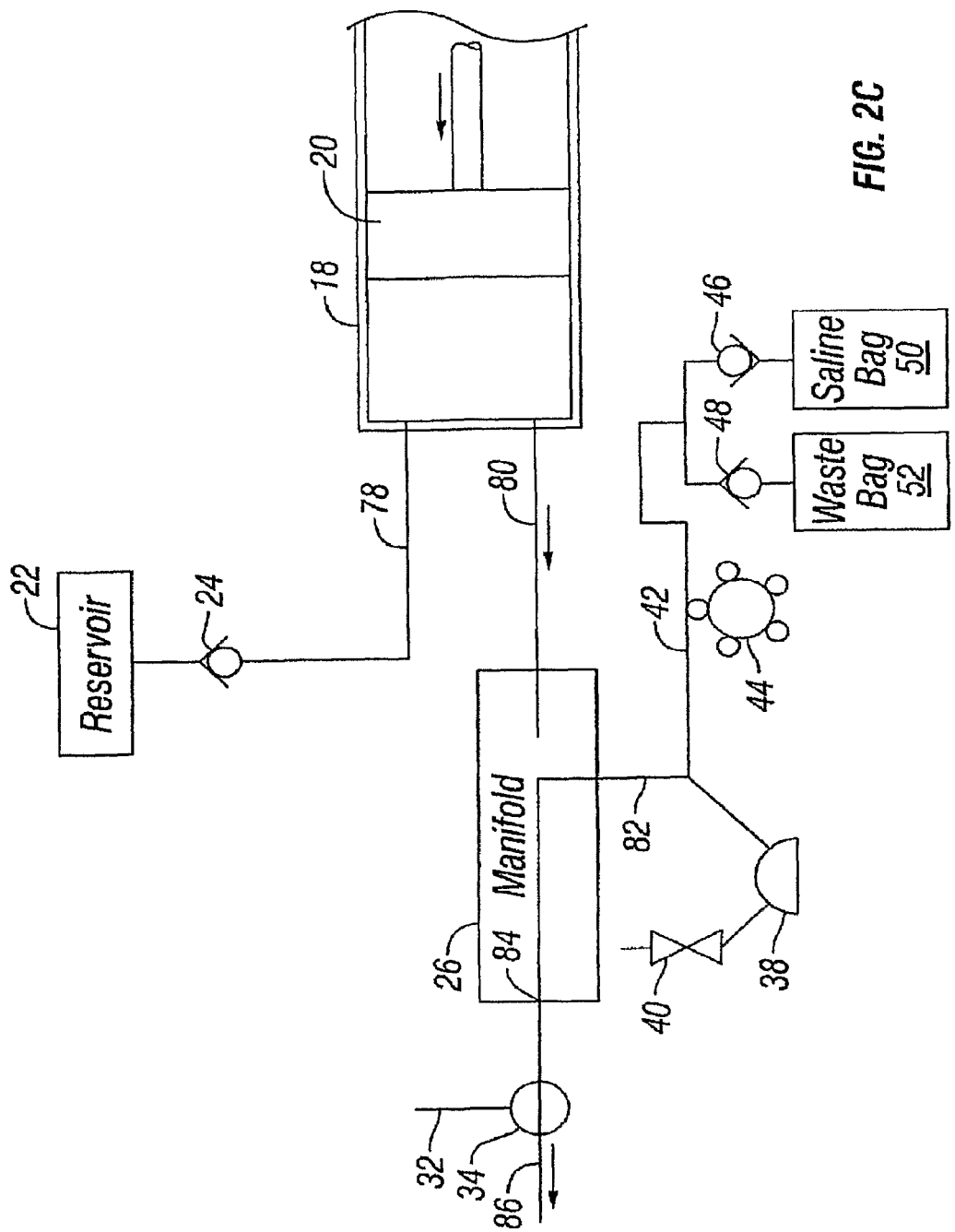
Figure 2D:
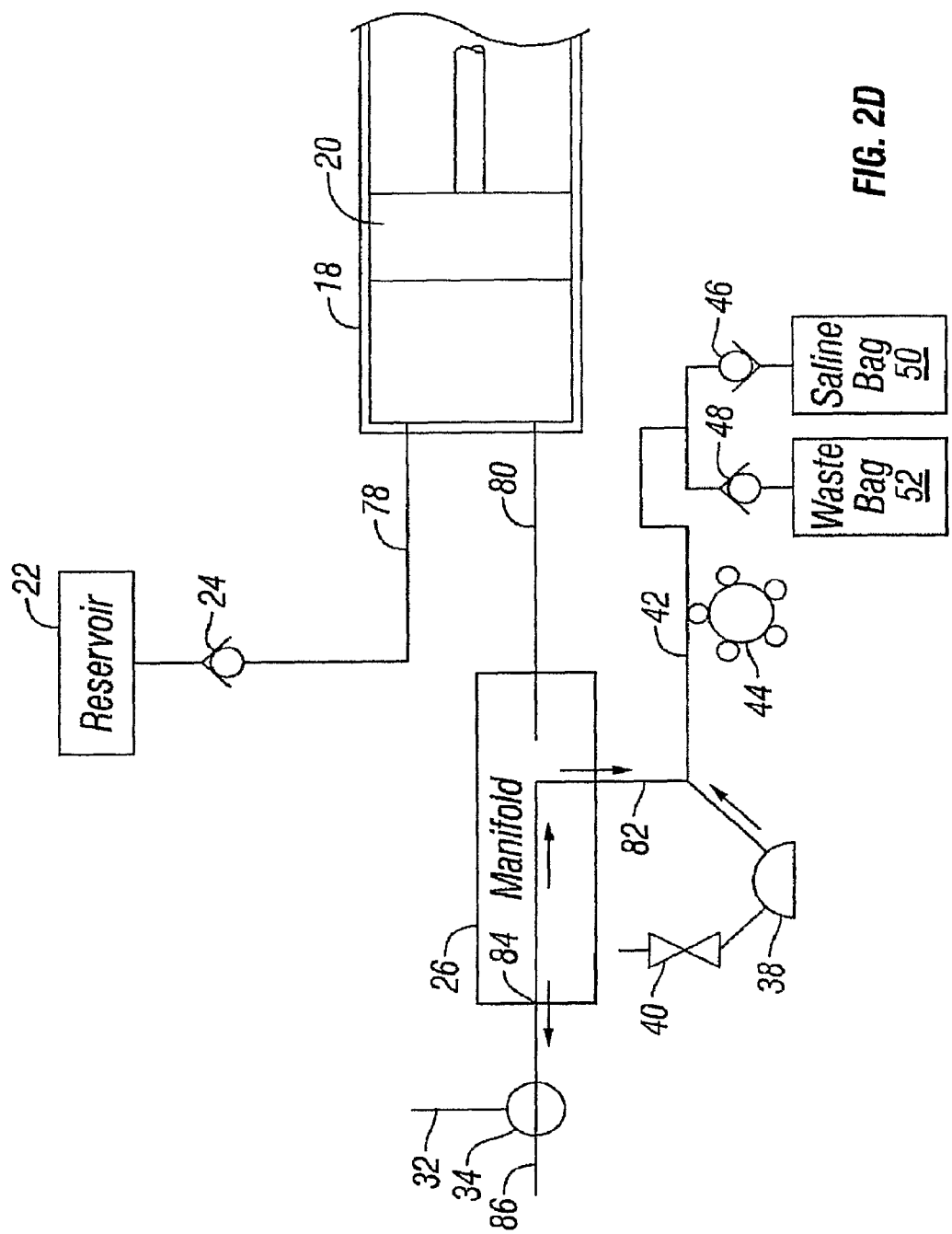
Figure 2E:
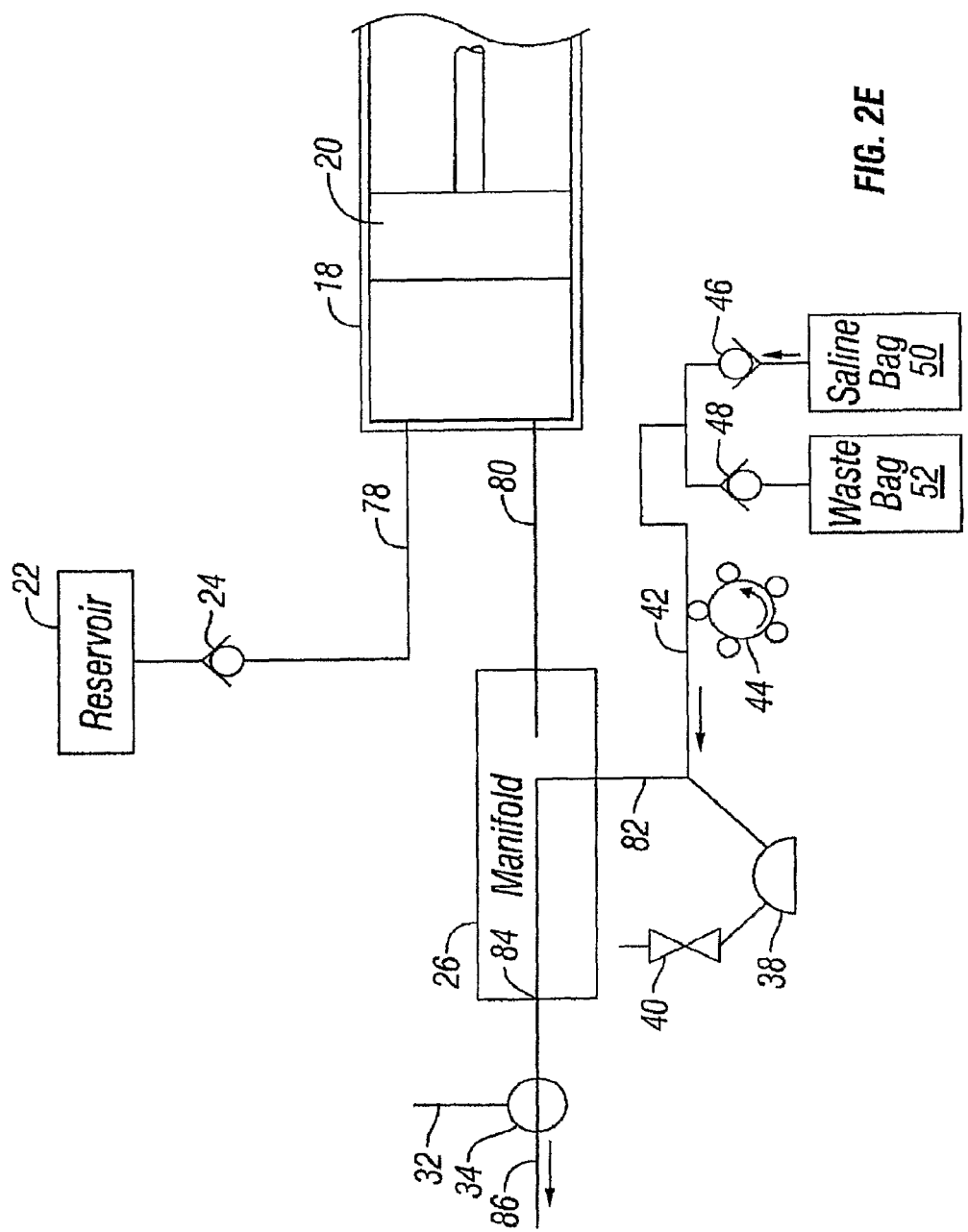
Figure 2F:
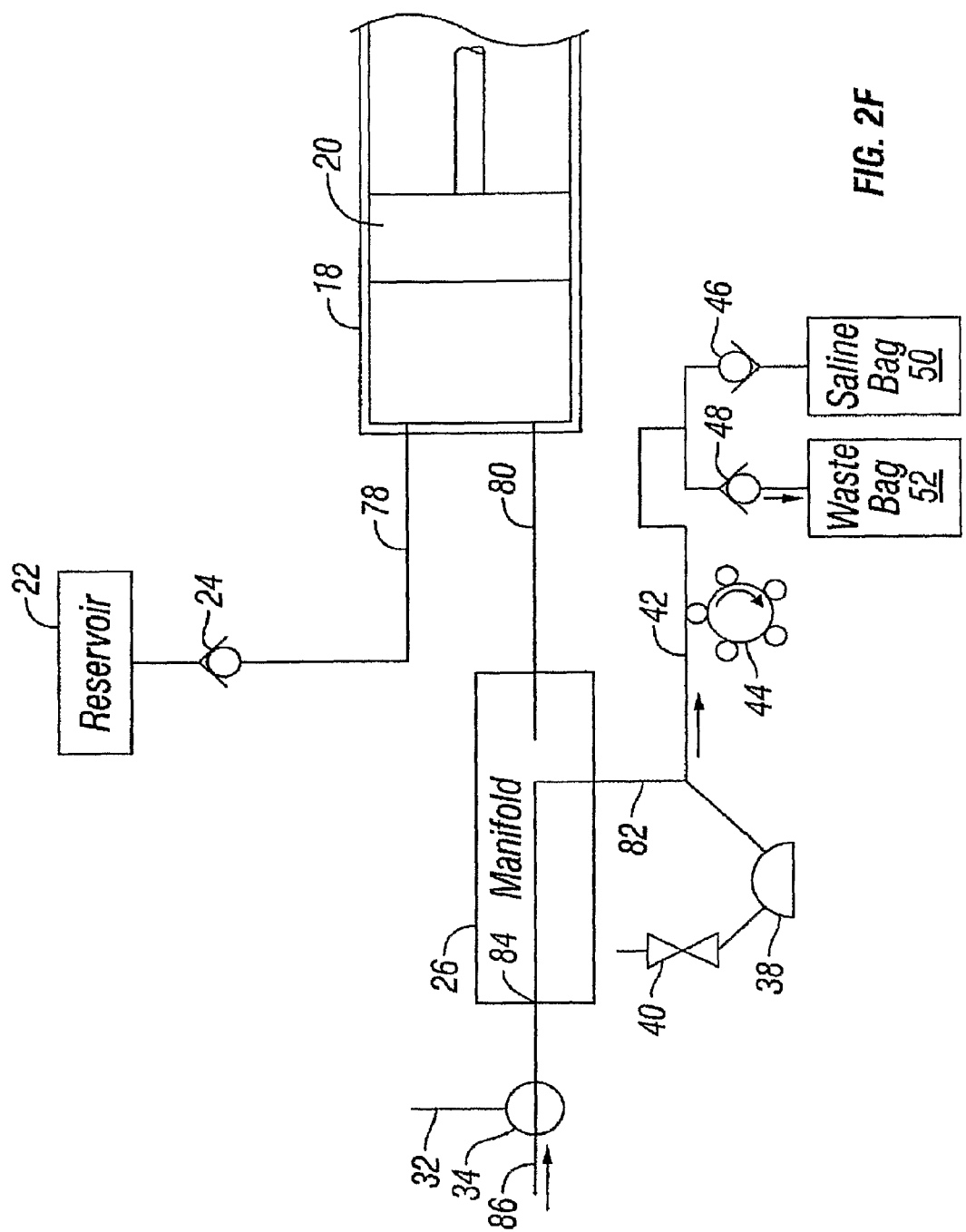
Figure 2G:
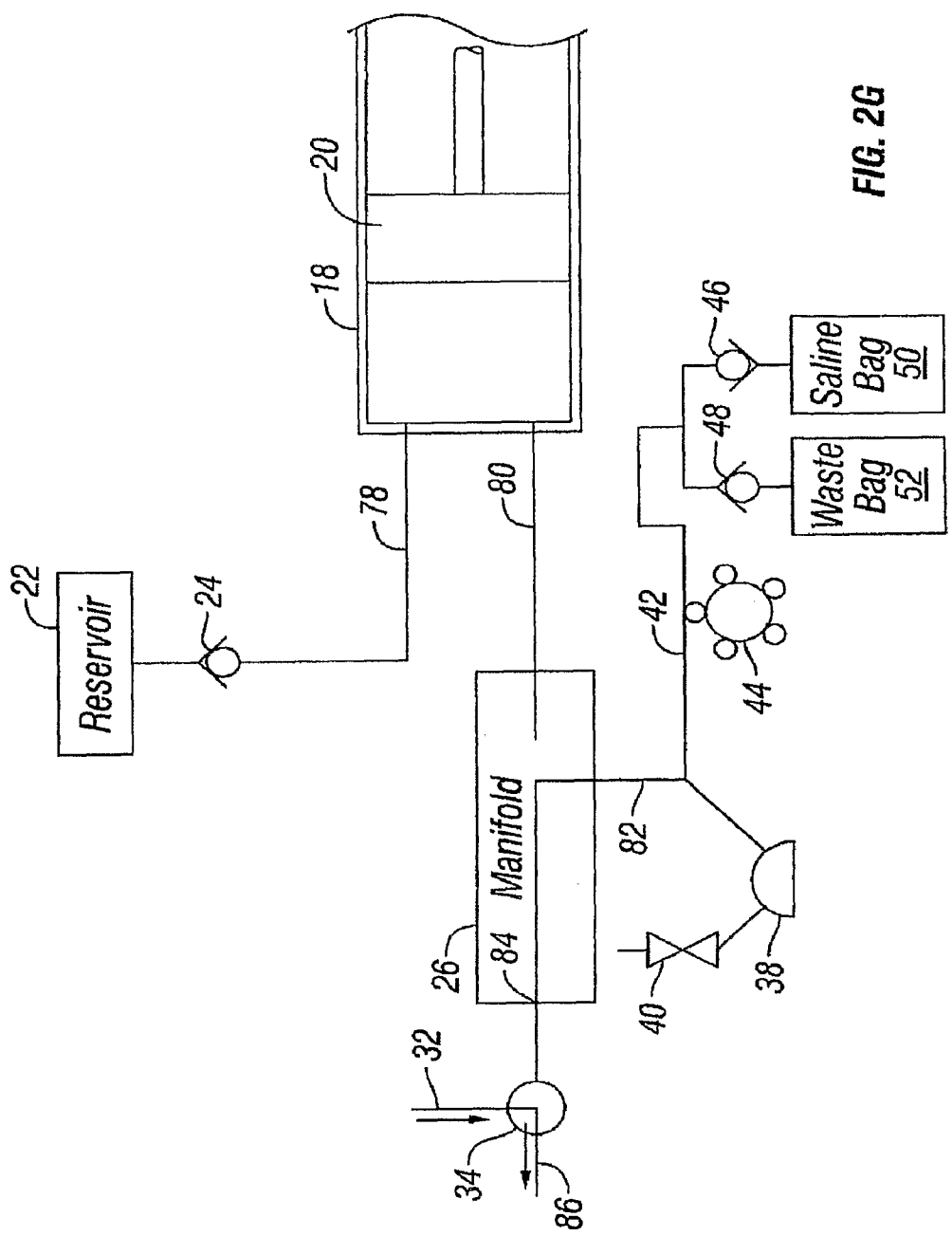

FIGS. 2A-2G are diagrams illustrating fluid flow paths during seven different operations of system 10. Those operational are contrast fill (FIG. 2A), air purge (FIG. 2B), patient inject (FIG. 2C), patient pressure (FIG. 2D), saline flush (FIG. 2E), aspirate waste (FIG. 2F), and medicate patient (FIG. 2G).

The contrast fill operation illustrated in FIG. 2A involves the filling of syringe body 18 with radiographic contrast material from reservoir (contrast media supply) 22. The contrast fill operation is performed during initial set up of system 10, and may be repeated during operation of system 10 whenever syringe body 18 is running low on radiographic contrast material.

During initial set up of system 10, plunger 20 is initially driven to its furthest forward position adjacent closed end 76 of syringe body 18. This will expel to the atmosphere the majority of the air which is located within syringe body 18.

Plunger 20 is then retracted, which creates a vacuum within syringe body 18 which draws contrast material from reservoir 22 through check valve 24 into syringe body 18 through upper port 78.

The Contrast Fill operation typically will result in some air being drawn into or remaining within syringe body 18. It is important, of course, to prevent air from being injected into the patient through catheter 30. That is the purpose of the Air Purge operation shown in FIG. 2B. Also, the location of two ports at different elevations allows for a greater amount of safety in preventing air bubbles in the injection.

During the Air Purge operation, plunger 20 travels forward to expel trapped air within syringe body 18. The air, being lighter than the contrast material, gathers near the top of syringe body 18. As plunger 20 moves forward, the air is expelled from syringe body 18 through upper port 78 and one-way valve 24. In the embodiment illustrated in FIG. 2B, one-way valve 24 is a weighted one-way valve which allows flow of radiographic contrast material from reservoir 22 to upper port 78, but will not allow radiographic contrast material to flow in the opposite direction from upper port 78 to reservoir 22. Valve 24 will, however, allow air to flow from port 78 to reservoir 22. As soon as radiographic contrast material begins flowing out of syringe body 18 through upper port 78 to valve 24, valve 24 closes to prevent any further flow toward reservoir 22.

Valve 24 can also, in alternative embodiments, be a solenoid actuated or motor driven valve operated under control of the electric circuitry within console 12. In either case, valve 24 is capable to withstanding the relatively high pressures to which it will be subjected during the inject operation. Preferably, valve 24 is capable of withstanding static fluid pressures up to about 1200 p.s.i.

FIG. 2C illustrates the Patient Inject operation. Plunger 20 travels forward under the interactive control of the user, who is controlling trigger 66 of remote control 14. The movement of Plunger 20 creates hydraulic pressure to force contrast material out of syringe body 18 through lower port 80 and through manifold 26 and high pressure tube 28 into catheter 30. As shown in FIG. 2C, syringe lower port 80 and patient port 84 are connected for fluid flow during the patient inject operation.

Manifold 26 contains a valve which controls the routing of fluid connections between patient port 84 and either syringe bottom port 80 or transducer/saline port 82. In one embodiment of the present invention, manifold 26 includes a spool valve which is spring biased so that patient port 84 is normally connected to transducer/saline port 82 (as illustrated in FIGS. 2A and 2B). When the pressure at syringe bottom port 80 builds with the movement of plunger 20 forward, the bias force against the spool valve is overcome so that syringe bottom port 80 is connected to patient port 84, and transducer/saline port 82 is disconnected the valve within manifold 26 protects pressure transducer 38 from being exposed to the high pressure generated by the patient inject operation.

The spool valve opens automatically during the patient inject operation in response to increase pressure exerted on it from the syringe lower port 80. The spool valve closes and returns to its original position allowing for connection of patient port 84 to transducer 38 when a slight vacuum is applied by retraction of plunger 20 at the end of each Patient Inject operation In an alternative embodiment, the valve within manifold 26 is an electromechanical or motor driven valve which is actuated at appropriate times to connect either syringe lower port 80 or transducer/saline port 82 to patient port 84. The actuator mechanism is controlled by console 12. Once again in this alternative embodiment, the valve protects pressure transducer 38 from being exposed to high pressure.

FIG. 2D illustrates the Patient Pressure operation. System 10 allows for reading of the patient's blood pressure, which is monitored through catheter 30. Patient blood pressure can be monitored through the use of pressure transducer 38, at any time except during the patient inject, saline flush, and waste aspirate operations. The pressure reading being produced by pressure transducer 38 may be normalized by manually opening stop-cock 40 and closing stop-cock 34 to expose pressure transducer 38 to atmospheric pressure.

During the Saline Flush operation illustrated in. FIG. 2E, saline solution is used to flush all of the internal lines, pressure transducer chamber 38, tube 28, and catheter 30. As shown in FIG. 2E, peristaltic pump 44 is operating in a direction which causes saline solution to be drawn from bag 50 through check valve 46 and through tubing 42 to saline port 82. Manifold 26 connects saline port 82 to patient port 84 so that saline solution is pumped out of patient port 84 and through tube 28 and catheter 30.

During the Aspirate Waste operation, patient port 84 is again connected to saline port 82. During this operation, peristaltic pump 44 is operating in the opposite direction from its rotation during the saline flush operation. As a result, patient fluids are aspirated from patient port 84 to saline port 82 and then through tubing 42 and check valve 48 into waste collection bag 52. Peristaltic pump 44 acts as a valve pinching/occluding tubing 42 and preventing back flow to/from saline and waste containers 50 and 52 in conjunction with check valves 46 and 48.

With catheter 30 in place within the patient, it may be desirable to supply patient medication. System 10 allows for that option by providing patient medication port 32. As shown in FIG. 2G, when stop-cock 34 is open, a medication source connected to port 32 will be connected to patient port 84, and thereby to catheter 30. During the medicate patient operation, peristaltic pump 44 and plunger 20 are not moving.

Figure 3A:
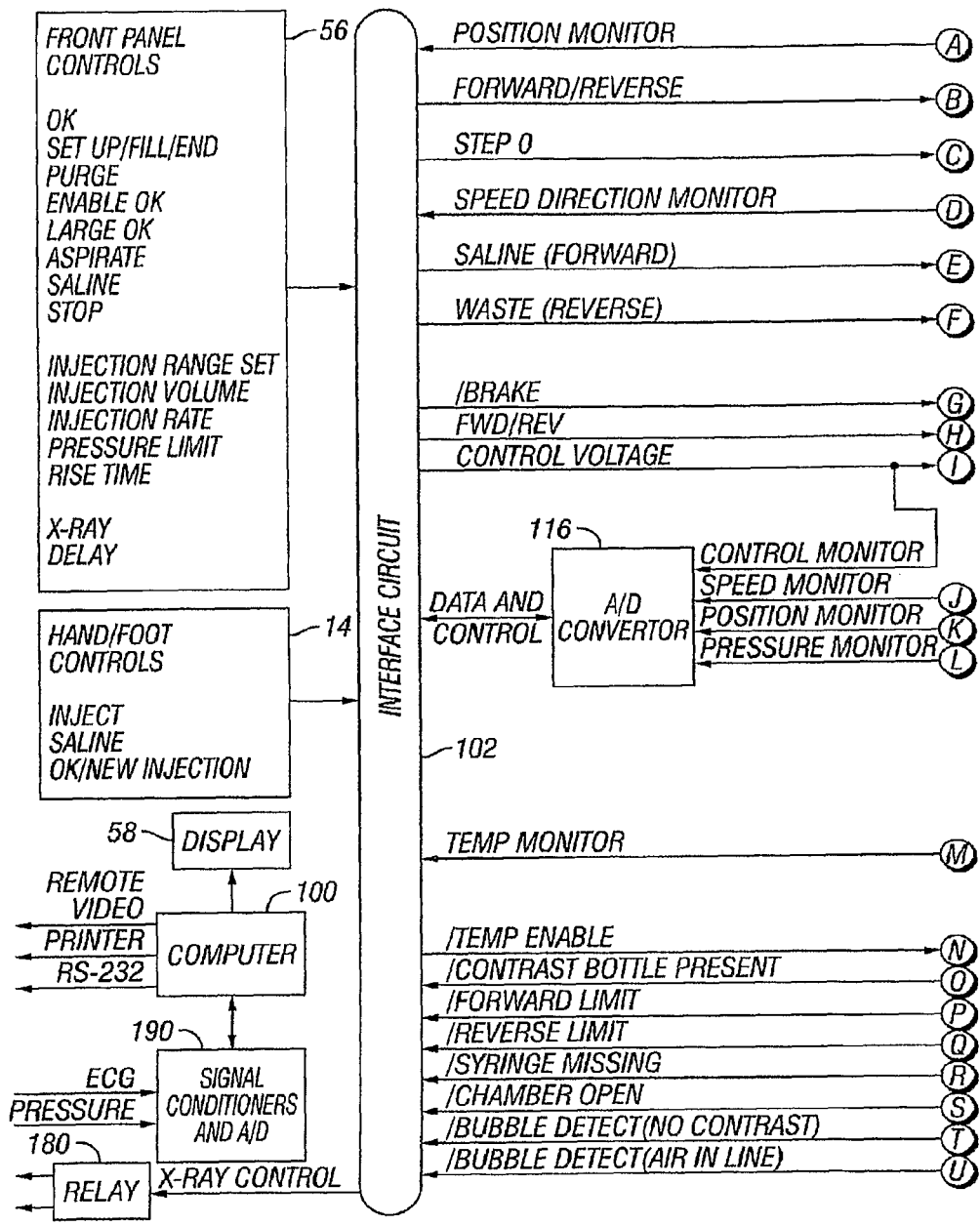
FIG. 3 is an electrical block diagram of the control system of the injector system of FIG. 1.
Figure 3B:
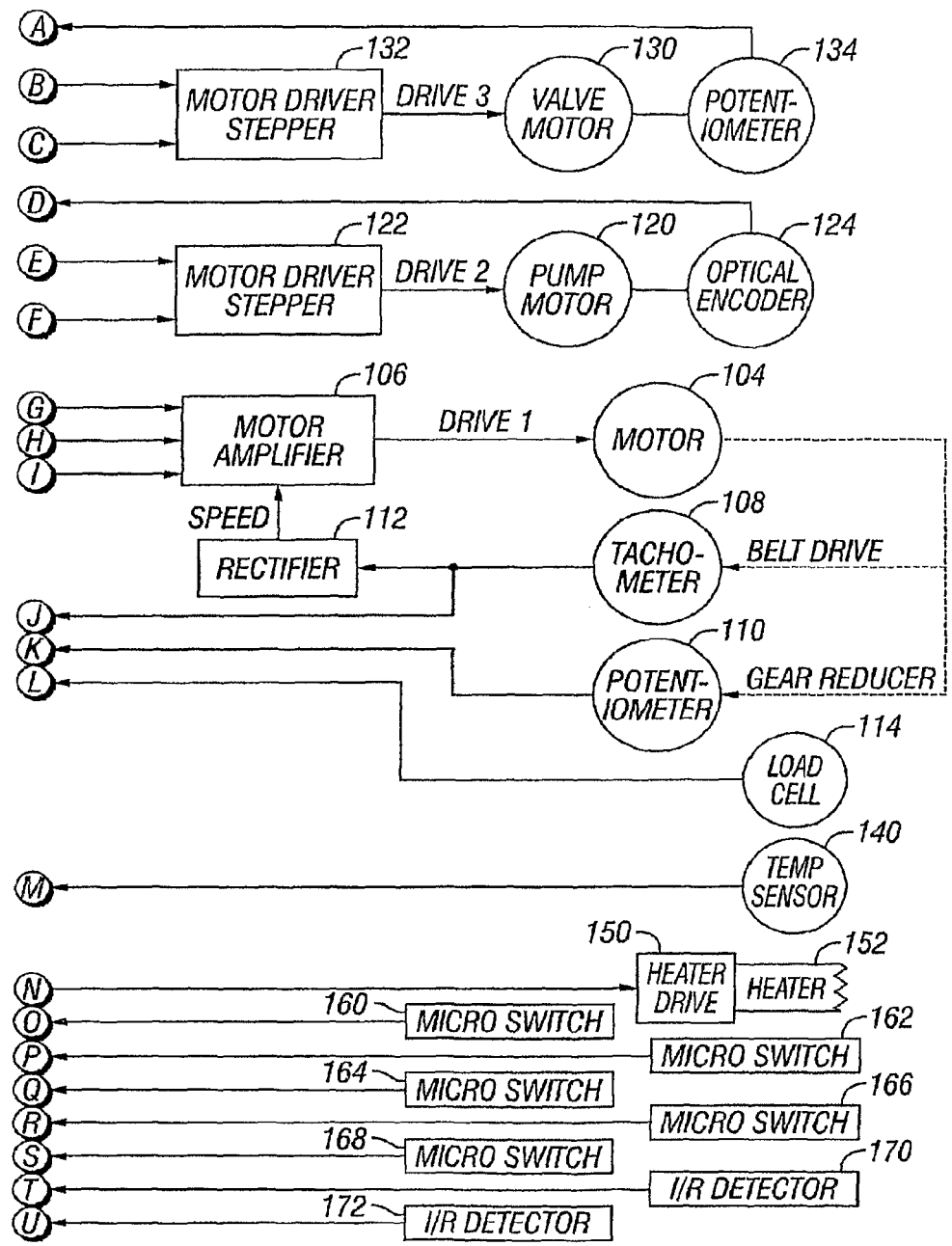

FIG. 3 is an electrical block diagram of a control system that has been used with above-described angiographic injector system. The electrical control system of FIG. 3 includes a single digital computer 100, which receives input signals from remote control 14 and front panel controls 56 through interface 102, and provides signals to display 58 to display operation data, alerts, status information and operator prompts. A subsequent preferred embodiment will describe an improved electrical control system; however the single computer system is being described herein to complete the functional description of an angiographic injector system that incorporates the components of the angiographic injector system 10 described above.

Computer 100 controls the motion of plunger 20 through a motor drive circuit which includes motor 104, motor amplifier 106, tachometer 108, potentiometer 110, a rectifier 112, pressure sensing load cell 114, and A/D converter 116.

Motor amplifier 106 provides a Drive 1 signal to motor 104 in response to Control Voltage, Fwd/Rev, and/Brake signals from computer 100 and a speed feedback signal from tachometer 108 through rectifier 112. The outputs of tachometer 108 and potentiometer 110 are supplied to computer 100 through A/D converter 116 as Speed Monitor and Position Monitor signals. These allow computer 100 to check motor speed, motor direction, and position (volume is a calculated value).

Pressure sensor 114 senses motor current or plunger force in order to measure the pressure being applied to the radiographic contrast material within syringe body 18. This Pressure Monitor Signal is supplied through A/D converter 116 and interface 102 to computer 100.

Peristaltic pump 44 is driven under the control of computer 100 through pump motor 120, motor driver 122 and optical encoder 124. Computer 100 provides Saline (Forward) and Waste (Reverse) drive signals to motor driver 122 to operate pump motor 120 in a forward direction for saline flush and a reverse direction for waste aspiration. Optical encoder 124 provides the Speed Direction Monitor signal to interface 102 which indicates both the speed and the direction of rotation of pump motor 120.

FIG. 3 illustrates an embodiment of the control system in which valve motor 130 is used to actuate valves such as one-way valve 24 and the valve within manifold 26. In this embodiment, computer 100 controls valve motor 130 through motor driver 132, and monitors position through a Position Monitor feedback signal from potentiometer 134. In this particular embodiment, valve motor 130 is a stepper motor.

Computer 100 monitors temperature of the contrast material based upon a Temp Monitor signal from temperature sensor 140. Temperature sensor 140 is preferably positioned near syringe body 18. If the temperature being sensed by temperature sensor 140 is too high, computer 100 will disable operation motor 104 to discontinue patient injection. If the temperature is too low, computer 100 provides a/Temp Enable drive signal to heater drive 150, which energizes heater 152. In one preferred embodiment, heater 152 is a resistive film heater which is positioned within syringe holder 116 adjacent to syringe body 18.

Computer 100 also receives feedback signals from contrast bottle sensor 160, forward limit sensor 162, reverse limit sensor 164, syringe missing sensor 166, chamber open sensor 168, no contrast bubble detector 170, and air in line bubble detector 172.

Contrast bottle sensor 160 is a miniature switch located within reservoir holder 72. The state of the Contrast Bottle Present signal from sensor 160 indicates whether a reservoir 22 is in position within holder 72. If reservoir 22 is not present, computer 100 will disable the fill operation.

Forward limit and reverse limit sensors 162 and 164 sense the end limit positions of plunger 20. When plunger 20 reaches its forward limit position, no further forward movement of plunger 20 is permitted. Similarly, when reverse limit sensor 164 indicates that plunger 20 has reached its reverse limit position, no further reverse movements are permitted.

Syringe missing sensor 166 is a miniature switch or infrared emitter/detector which indicates when syringe body 18 is not in position within syringe holder 16. If syringe body 18 is not in position, all movement functions are disabled except that plunger 20 can move to its reverse limit position (i.e., return to zero).

Chamber open sensor 168 is a miniature switch or infrared emitter/detector which senses when door 70 of syringe holder 16 is open. When the signal from sensor 168 indicates that door 70 is open, all movement functions are disabled. Only when door 70 is closed and locked may any movement be allowed. When door 70 is indicated as closed and sensor 166 indicates the syringe body 18 is in position, other normal functions of the system 10 can proceed.

Bubble detector 170 is positioned between reservoir 22 and top port 78, and is preferably an infrared emitter/detector which senses air bubbles. If an air bubble is sensed in the flow path between reservoir 22 and top port 78 during a fill operation, the fill operation is disabled until a new reservoir is connected.

Bubble detector 172 is positioned to sense air bubbles in high pressure line 28. It is preferably an infrared emitter/detector type of bubble detector. Any air bubble which is sensed in high pressure line 28 results in the disabling of all fluid push out functions, whether the fluid is saline solution from peristaltic pump 44 or contrast material from syringe body 18.

The control system of FIG. 3 also includes the capability to provide a control signal to x-ray equipment through relay 180 which is controlled by computer 100. In addition, computer 100 receives data from blood pressure transducer 38 and from an electrocardiograph (ECG) system, which is separate from injector system 10. The Pressure and ECG signals are received through signal conditioners and A/D converter 190, and are transferred to computer 100. The ECG signal is used by computer 100 in one preferred embodiment, to synchronize operation of motor 104 (and thus the Patient Inject operation) with heart beats.

Blood flow to the heart occurs predominantly in diastole (when the heart is between contractions). Continuous injection of contrast material results in spillage of the contrast material into the aorta during systole (during contraction). By injecting primarily during diastole, contrast dosage can be reduced without impairing the completeness of the contrast injection into the coronary artery.

In a preferred embodiment, the injection of radiographic contrast material is synchronized to the coronary artery blood flow. The time periods of systole and diastole are determined using an electrocardiographic (ECG) electrical signal, arterial blood pressure waveform analysis, or other timing based on the heart rate. By controlling speed of motor 104, speed and therefore movement of plunger 20, the injection of contrast material is interrupted during the period of systole, which reduces or stops contrast injection during this time. In combination with remote control 14, the operator can vary the rate of contrast injection into the coronary artery while computer 100 automatically pulses the contrast injection to the cardiac cycle.

The inertial forces of the moving contrast material and expansion of the containers and tubing holding the contrast material and transmitting it to the patient can cause a phase lag between movement of plunger 20 within syringe body 18 and movement of contrast material out of catheter 30 into the patient. To adjust to the phase lag between the plunger 20 movement and contrast expulsion into the patient, a variable time offset can be entered through control panel 54 such that the timing of the cardiac cycle can be offset by a selected time. Since the magnitude of the phase lag may be dependent on the frequency of the heart rate, an algorithm within computer 100 continuously and automatically adjusts the magnitude of the time offset, based on the instantaneous heart rate during the injection of contrast material.

FIG. 4 shows one embodiment of control panel 54 which illustrates the front panel control switches 56 and display 58 of one embodiment of the present invention. Front panel control switches 56 include Set Up/Fill/End switch 200, Purge switch 202, Aspirate switch 204, Saline switch 206, Enable OK switch 208, Injection Volume Limit switches 210a and 210b, Injection Flow Rate Limit switches 212a and 212b, Injection Pressure Limit switches 214a and 214b, Rise Time switches 216a and 216b OK switch 218, Injection Range Toggle switch 220, Large Injection OK switch 222, and Stop switch 224.

Set Up/Fill/End switch 200 is a momentary push button switch. When it is first activated, the user will be notified to place syringe 18 in syringe holder 16. When syringe 18 has been placed in syringe holder 16 (which is indicated to computer 100 by sensor 166), the user will be instructed to close and lock the chamber (i.e., to close door 70). Plunger 20 is moved to its full forward position expelling all air within the syringe. Display 58 then indicates to the operator that contrast reservoir 22 should be connected. Once contrast reservoir 22 has been put in place, the operator is requested to depress OK switch 218, at which time plunger 20 will retract at a set rate (preferably corresponding to a flow rate of 10 ml per second) to the maximum syringe volume. If the real speed (as indicated by feedback to computer 100 from A/D converter 116) is greater than the set speed, system 10 will stop.

Once plunger 20 is at its rearward most position, motor 104 is actuated to move plunger 20 forward to purge all air bubbles. Pressure sensor 114 provides an indication of when one-way valve 24 is closed and pressure is beginning to build up within syringe body 18. Once the purge is completed, the total volume injected and the number of injections counter is reset.

The actuation of switch 200 also allows for Ml retraction and disengagement of plunger 20 from syringe body 18.

Purge switch 202 is a protected momentary push button switch. When activated, Purge switch 202 causes plunger 20 to move forward to expel air through top port 78. The forward movement of plunger 20 is limited and stopped when a predetermined pressure within syringe 18 is reached. This is sensed by pressure sensor 114. The purge operation, which is initiated by Purge switch 202 will expel air within syringe 20. The user may also use Purge switch 202 to purge fluid through patient port 84 by depressing and holding Purge switch 202 continuously on.

Aspirate switch 204 is a momentary push button switch which causes computer 100 to activate pump motor 120 of peristaltic pump 44. Pump motor 120 is operated to aspirate catheter 30 at a set speed, with the aspirated fluid being collected in waste bag 52. All other motion functions are disengaged during aspiration. If the real speed of motor 120 is greater than a set speed, computer 100 will stop motor 120.

Saline switch 206 is an alternate action switch. Pump motor 120 is activated in response to Saline switch 206 being pushed on, and saline solution from bag 50 is introduced into manifold 26 and catheter 30 at a set speed. If Saline switch 206 is not pushed a second time to stop the flow of saline solution within 10 seconds, computer 100 automatically stops pump motor 120. If a time-out is reached, Saline switch 206 must be reset to its original state prior to initiating any further actions.

Enable OK switch 208 is a momentary push button switch. After the system has detected a disabling function at the end of an injection other than a limit, Enable OK switch 208 must be activated prior to activating OK switch 218 and initiating any further function.

Injection Volume Limit keys 210a and 210b are pushed to either increase or decrease the maximum injection volume that the system will inject during any one injection. Key 210a causes an increase in the maximum volume value, and key 210b causes a decrease. Once the maximum injection volume limit has been set, if the measured volume reaches the set value, computer 100 will stop motor 104 and will not restart until OK switch 218 has been depressed. If a large injection (i.e., greater than 10 ml) has been selected, OK switch 218 and Large Injection OK switch 220 must both be reset prior to initiating the large injection.

Injection Flow Rate Limit keys 212a and 212b allow the physician to select the maximum flow rate that the system can reach during any one injection. If the measured rate (which is determined by the feedback signals from tachometer 108 and potentiometer 110) reaches the set value, computer 100 will control motor 104 to limit the flow rate to the set value.

Injection Pressure Limit keys 214a and 214b allow the physician to select the maximum pressure that the system can reach during any one injection. If the measured pressure, as determined by pressure sensor 114, reaches the set value, computer 100 will control motor 104 to limit the pressure to the injection pressure limit. The injection rate will also be limited as a result.

Rise Time keys 216a and 216b allow the physician to select the rise time that the system will allow while changing flow rate during any one injection. Computer 100 controls motor 104 to limit the rise time to the set value.

In alternative embodiments, keys 210a-210b, 212a-212b, 214a-214b, and 216a-216b can be replaced by other devices for selecting numerical values. These include selector dials, numerical keypads, and touch screens.

OK switch 218 is a momentary push button switch which resets functions and hardware sensors. In response to OK switch 218 being activated, computer 100 controls display 58 to ask the operator to acknowledge that the correct function has been selected. Activation of OK switch 218 causes the status to be set to Ready.

Injection Range switch 220 is a toggle switch. Depending on whether switch 220 is in the "small" or "large" position, it selects either a high or a low injection volume range for the next injection.

Large Injection OK switch 222 is a momentary push button switch. When the large injection range has been selected by injection range switch 220, the Large Injection OK button 222 must be activated to enable OK switch 218. OK switch 218 must be activated prior to each injection. On large volume injections, the user is required to verify the volume selected by activating first Large Injection OK switch 222 and then OK switch 218.

Stop switch 224 is a momentary push button switch. When stop switch 224 is pushed, it disables all functions. Display 58 remains active.

Display panel 58 includes Set-Up display 250, Status display 252, Alerts display 254, Limits display 256, total number of injections display 260, total volume injection display 262, flow rate display 264, injection volume display 266, injection volume limit display 268, injection rate limit display 270, pressure limit display 272, rise time minimum display 274, large injection display 276, and real time clock display 278.

Set-Up display 250 contains a series of messages which are displayed as the operator goes through the set up procedure. The display of messages in set up display 250 are initiated by the actuation of set up switch 200 as described previously.

Status display 252 provides a flashing indication of one of several different operating conditions. In the embodiment shown in FIG. 4, these status conditions which can be displayed include "Ready", "Set-Up", "Injecting", "Filling", "Flushing", and "Aspirating".

Alerts display 254 and Limits display 256 notify the operator of conditions in which system 10 has encountered a critical control parameter and will disable operation, or has reached an upper or lower limit and will continue to function in a limited fashion, or has reached an upper or lower limit and will continue to operate.

Total number of injections display 260 displays the total number of injections (cumulative) given for the current patient case. The cumulative total volume injected during the current patient case is displayed by total volume display 262.

Displays 264 and 266 provide information on the current or last injection. Display 264 shows digital value of the real time flow rate to the patient during injection. Once the injection is completed, the value displayed on display 264 represents the peak flow rate reached during that injection. Display 266 shows the digital value of the volume injected during the most recent injection.

Display 268 displays the digital value of the maximum injection volume selected by operation of switches 210a and 210b. Similarly, display 270 shows the digital value of the maximum flow rate that the system will allow, as selected by switches 212a and 212b.

Display 272 shows the digital value of the maximum pressure that the system will allow to be developed in syringe 18. The pressure limit is selected by switches 214a and 214b.

Display 274 displays the minimum rise time that the system will allow while changing flow rate. The minimum rise time is selected through switches 216a and 216b.

Large injection display 276 provides a clear indication when the large injection scale has been selected by the operator.

Real-time clock display 278 shows the current time in hours, minutes, and seconds.

Figure 5A:
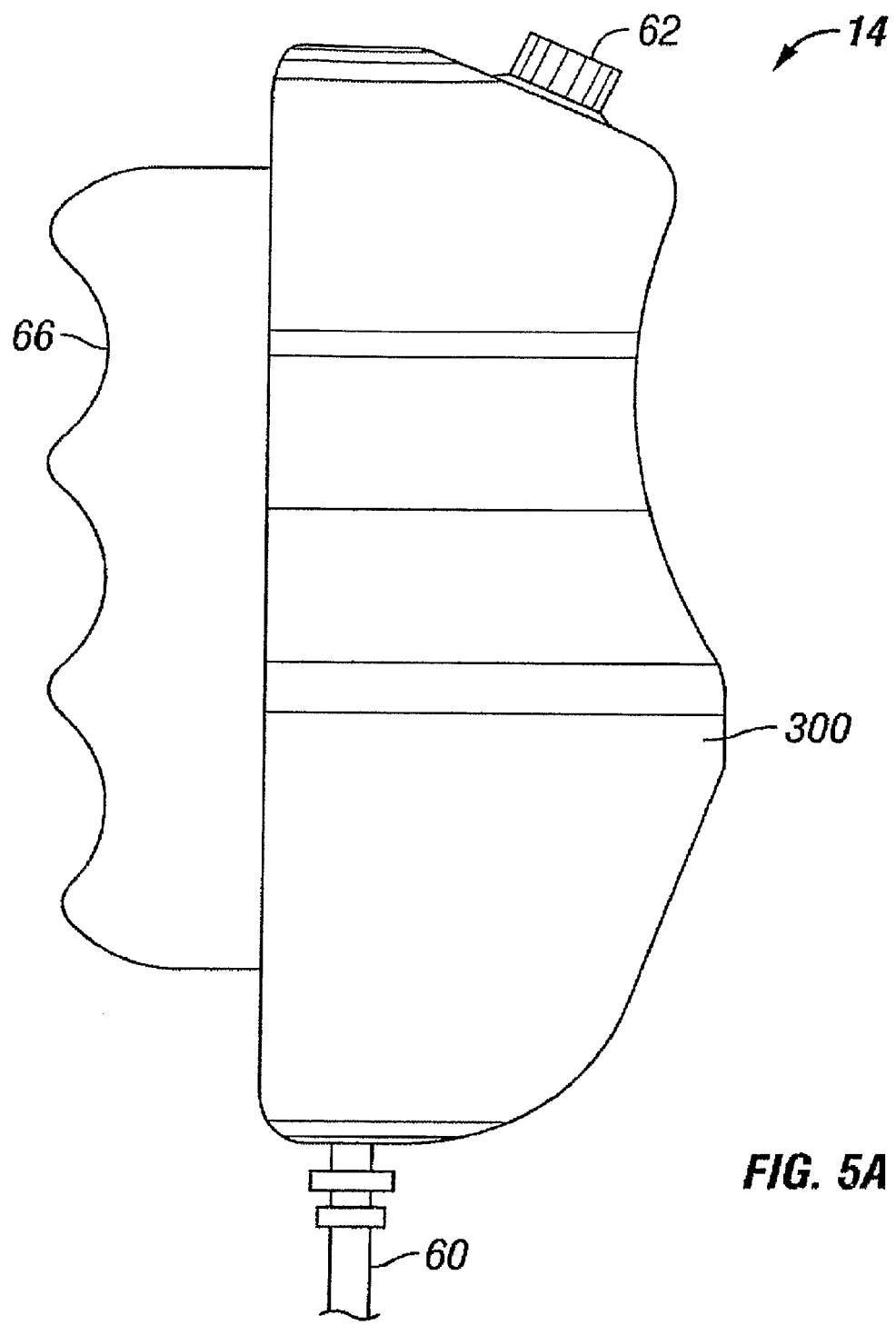
FIGS. 5A and 5B are side and partial top perspective views of a remote control of the system of FIG. 1.
Figure 5B:
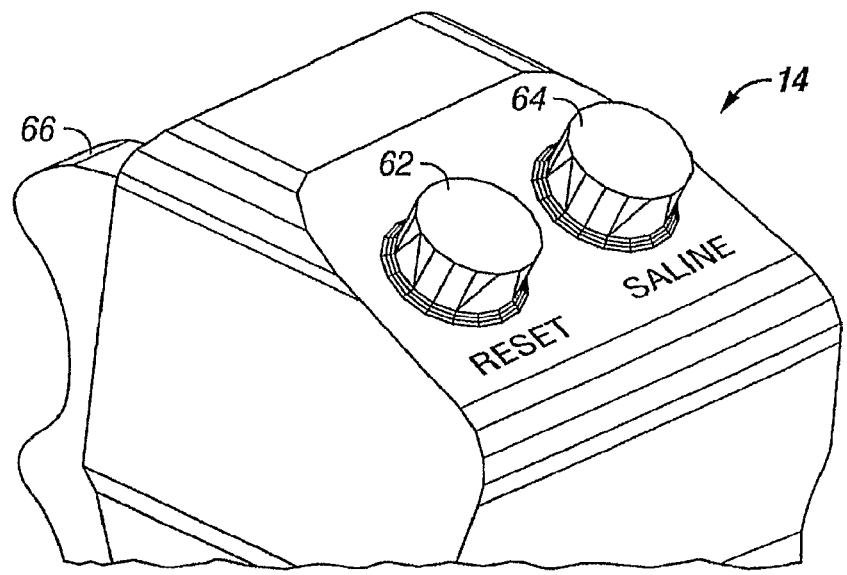
Figure 6:
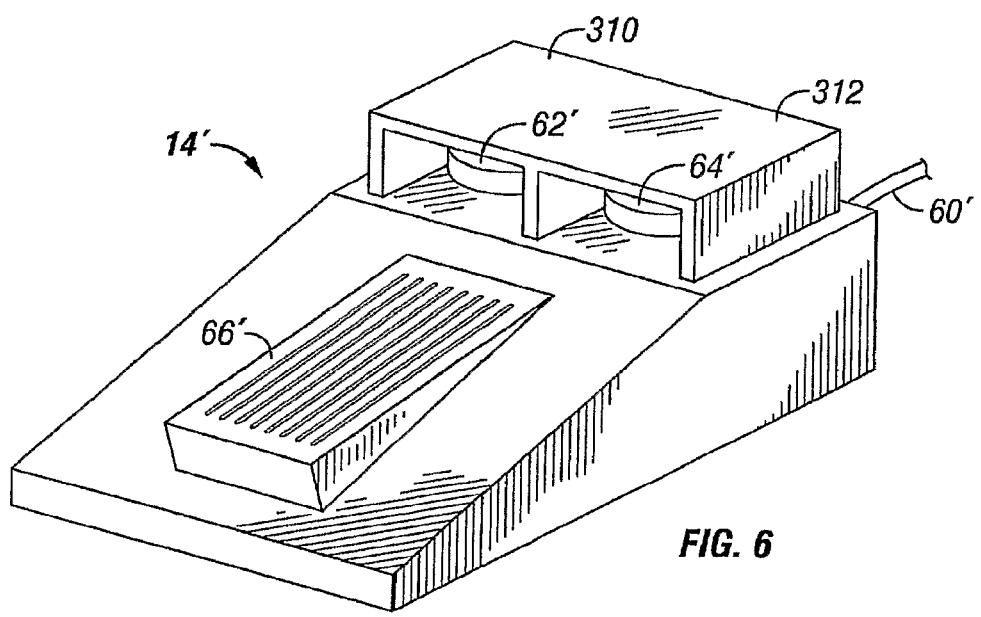
FIG. 6 is a perspective view of a foot operated remote control.

FIGS. 5A and 5B show one embodiment of a remote control 14 which includes main housing 300, which is designed to conform to the users hand. Trigger 66 is movable with respect to housing 300, and the position of trigger 66 generates a command signal which is a function of trigger position. In one embodiment, trigger 66 is linked to a potentiometer within housing 300. The command signal controls the injunction flow rate or speed. The flow rate is directly proportional to trigger position.

Reset switch 62 is a momentary push button switch whose function is identical to that of OK switch 218. Alternatively, Reset switch 62 may also be labeled "OK".

Saline switch 64 on remote control 14 is an alternate action push button switch which is pushed to turn on and pushed again to turn off. The function of Saline switch 62 is the same as that of Saline switch 206 on front panel 54.

As illustrated in another embodiment of the present invention, an alternative remote control 14' in the form of a foot pedal is used instead of the hand held remote control 14 illustrated in FIG. 1 and in FIGS. 5A and 5B. Foot pedal remote control 14' includes foot operated speed pedal or trigger 66' for providing a command signal, as well as Reset or OK switch 62' and Saline switch 64'. Covers 310 and 312 protect switches 62' and 64' so that they can only be actuated by hand and not accidentally by foot. Foot pedal remote control 14' is connected to console 12 by cable 60', but could alternatively be connected by a wireless link.

FIGS. 7A-7D and FIGS. 8A-8C illustrate the construction and operation of one way valve 24 and manifold 26 during Contrast Fill, Air Purge and Patient Injection operation.

FIGS. 7A and 8A illustrate one way or check valve 24, manifold 26, syringe body 18, and plunger 20 during a Contrast Fill operation. Inlet check valve of one way valve 24 includes weighted ball 350 which is positioned at its lower seated position within valve chamber 352 in FIGS. 7A and 7B. Contrast material is being drawn into syringe body 18 by the rearward movement of plunger 20. The contrast material flows through passages 354 around ball 350 and into upper port 78.

Manifold 26 contains spring loaded spool valve 360, which includes spool body 362, shaft 364, O-rings 366, 368 and 370, bias spring 372, and retainer 374. As shown in FIG. 7A, during the Contrast Fill operation, bias spring 372 urges spool body 362 to its right-most position toward syringe body 18. In this position, spool body 362 blocks lower port 80 of syringe body 18 while connecting transducer saline port 82 to patient port 84 through diagonal passage 376. O-rings 366 and 368 on the one hand, and O-ring 370 on the other hand, are positioned on the opposite sides of diagonal passage 376 to provide a fluid seal.

FIGS. 7B and 8B illustrate the Air Purge operation. Syringe body 18 has been filled with contrast fluid, but also contains trapped air. Plunger 20 is driven forward to force the air out of syringe body 18 through upper port 78 and through check valve 24. The force of the air may cause a slight lifting of ball 350 in check valve 20. Ball 350, however, is sufficiently heavy that the air being forced out of syringe body 18 and back toward reservoir 22 cannot lift ball 350 into its uppermost seated position where it would block the flow of air out of syringe body 18.

During the Air Purge operation, spool valve 360 is in the same position as in FIG. 7A. Diagonal passage 376 connects transducer saline port 82 with patient port 84. As a result pressure monitoring by pressure transducer 38 can be performed during the Air Purge (as well as the Contrast Fill) operation.

FIGS. 7C and 8C illustrate the state of manifold 26 and check valve 24 at the end of the Air Purge operation and at the beginning of a Patient Inject operation.

In FIG. 7C, all air has been expelled from syringe body 18. Ball 350 may float on the radiographic contrast material, so that when all air has been removed and the radiographic contrast material begins to flow out of syringe body 18 and through upper port 78 to valve chamber 352, ball 350 is moved upwards to its upper seated position. Ball 350 blocks any continued upward flow of radiographic contrast material, as is illustrated in FIGS. 7C and 8C.

In the state which is illustrated in FIG. 7C, the pressure within syringe body 18, and specifically the pressure in lower port 80 has not yet reached a level at which the bias force of spring 372 has been overcome. As a result, spool body 362 has not yet moved to the left and diagonal passage 376 continues to connect transducer saline port 82 with patient port 84.

Figure 7D:
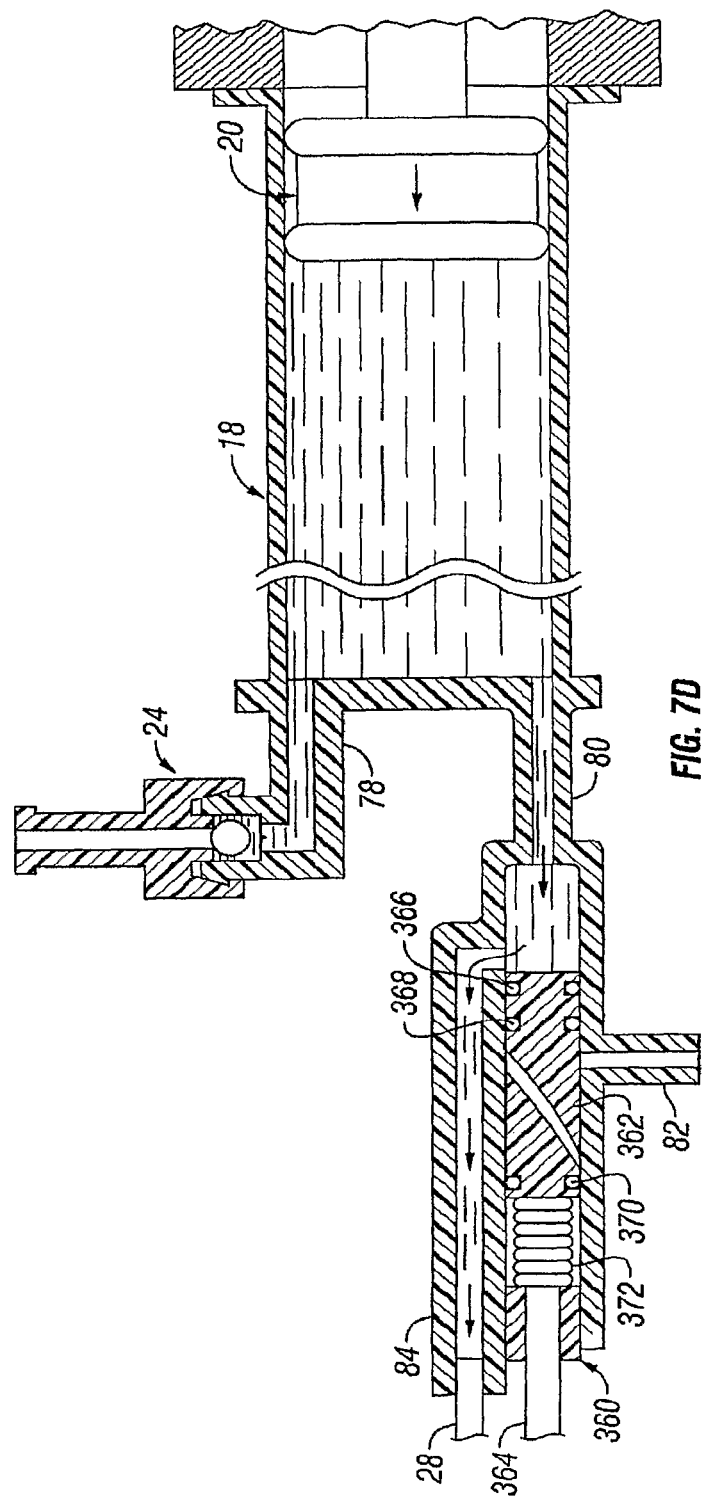

FIG. 7D illustrates the patient inject operation. Plunger 20 is moving forward, and inlet check valve 24 is closed. The pressure at lower port 80 has become sufficiently high to overcome the bias force of spring 372. Spool body 362 has been driven to the left so that lower port 80 is connected to patient port 84. At the same time spool body 362 blocks transducer/saline port 82.

By virtue of the operation of spool valve 360, the high pressure generated by movement of plunger 20 and syringe body 18 is directly connected to patient port 84, while saline port 82 and pressure transducer 38 are protected from the high pressure. The pressure to actuate may be variable and determined after manufacture by increasing or decreasing the syringe preload.

Those skilled in the art will appreciated that other configurations of the general angiographic injector system 10 can be configured. For example, the alternative syringe and mounting system portions of the referenced angiographic injector system described in U.S. Pat. No. 6,099,502, entitled "Dual Port Syringe" (herein incorporated by reference), could be employed to replace and/or modify those previously described. Further, those skilled in the art will recognize other improvements such as to the manifold portion of the assembly, as for example described in U.S. Pat. No. 6,221,045, entitled "Angiographic Injector System with Automatic High/Low Pressure Switching" (herein incorporated by reference), could be employed, as well as other configurations of the remote control 14. Several alternative configurations of the remote control assembly are described in this referenced application and in U.S. Pat. No. 5,916,165, entitled "Pneumatic Controller-and Method" and U.S. Pat. No. D404,717, entitled "Hand-Held Pneumatic Control Device, all of which are herein incorporated by reference.

Figure 9A:
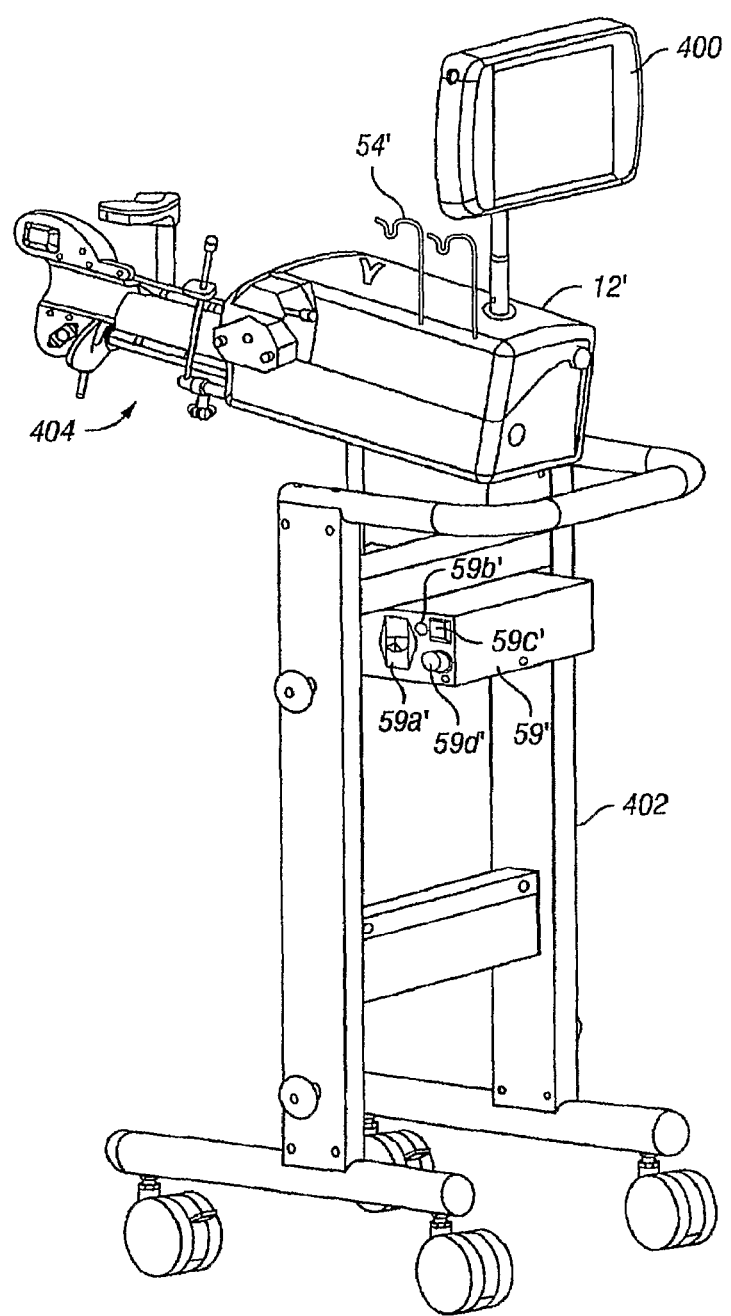
FIGS. 9A and 9B are perspective views illustrating a second embodiment configuration of an angiographic injector system.
Figure 9B:
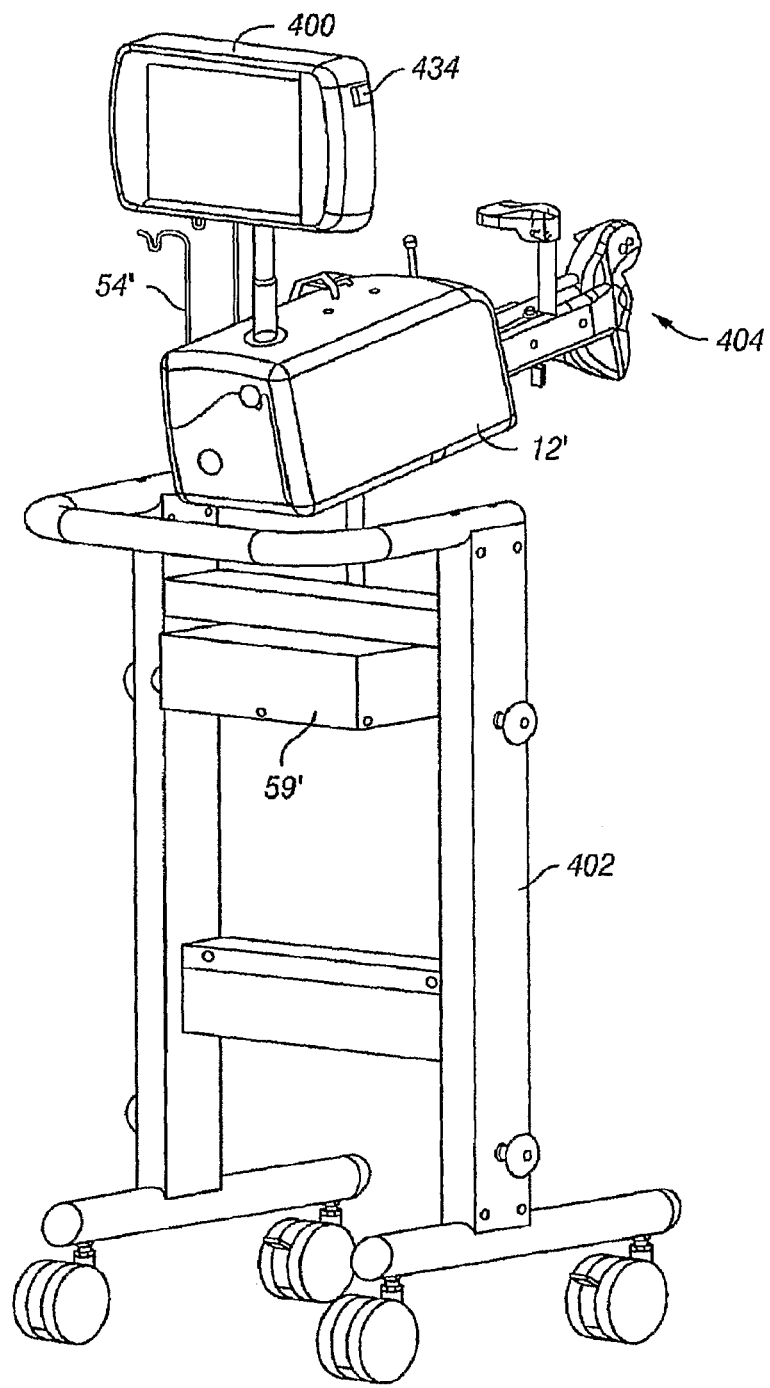
Figure 10:
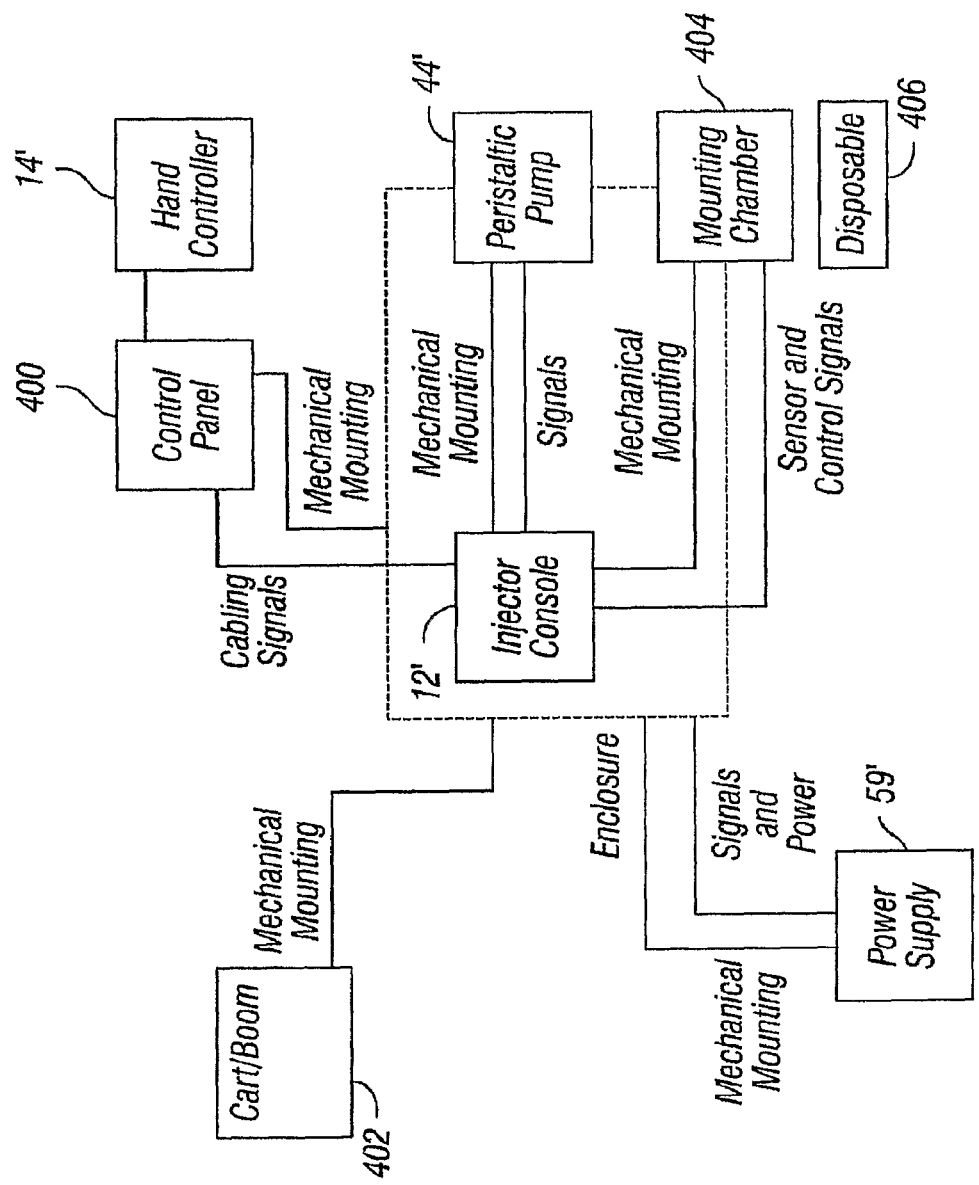
FIG. 10 is a mechanical block diagram illustrating the mounting configuration of the portions of the system disclosed in FIG. 9.

An alternative embodiment configuration of the angiographic injector system of the preceding figures is generally indicated at 10' in FIGS. 9a and 9b. In the embodiment illustrated in FIG. 9, the physical locations of some of the components of the angiographic injector system 10 have been rearranged for facilitating use of the system. For example, the user interface 54, the control switches 56 and the display 58 of the first described embodiment have been consolidated into a single control panel 400. In the second embodiment illustrated, the control panel 400 mounts to the console or injector head 12' on a swivel base that may be disconnected and reconnected by the user for optimal placement. A mechanical diagrammatic chart of the FIG. 9 configuration is illustrated in FIG. 10. Referring to FIGS. 9 and 10, the Power supply 59' circuits are illustrated as being mechanically mounted separate from the console 12'. The console and power supply are mounted to a cart, generally indicated at 402 which includes wheels for easy movement and which is preferably designed to provide stability and deter tipping when used in its intended method. The cart enables the console and power supply assemblies to be rapidly attached and detached for allowing docking of the console and power supply to a bed or other stationary device equipped with a mating connection device. Referring to FIG. 10, the hand controller 14' is illustrated as being operatively connected to the control panel 400, and the peristaltic pump assembly 44' is indicated as being mechanically mounted to the console 12'. The assembly for holding the syringe and related components that have been previously described with regard to the first embodiment of the invention are generally indicated by the functional block entitled "mounting chamber" 404. Those components previously described and referred to as "disposable" items (i.e.: the syringe, the piston within the syringe body, the contrast valve, the patient manifold, the contrast spike and the patient blood pressure port) are generally designated by the functional block 406.

Figure 11A:
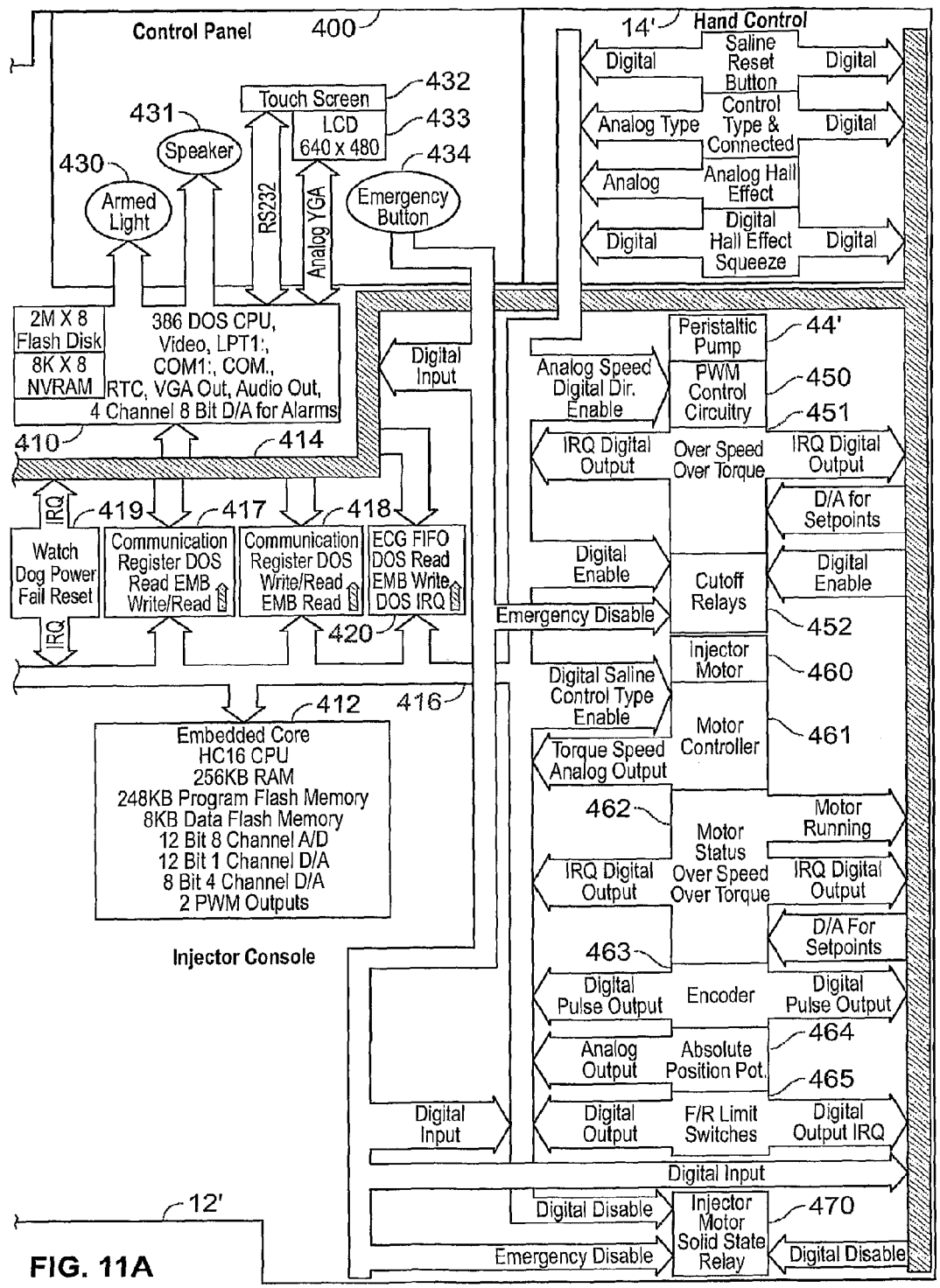
FIGS. 11A and 11B are an electrical block diagram of the control system and electrical functions of the system of FIGS. 9 and 10.
Figure 11B:
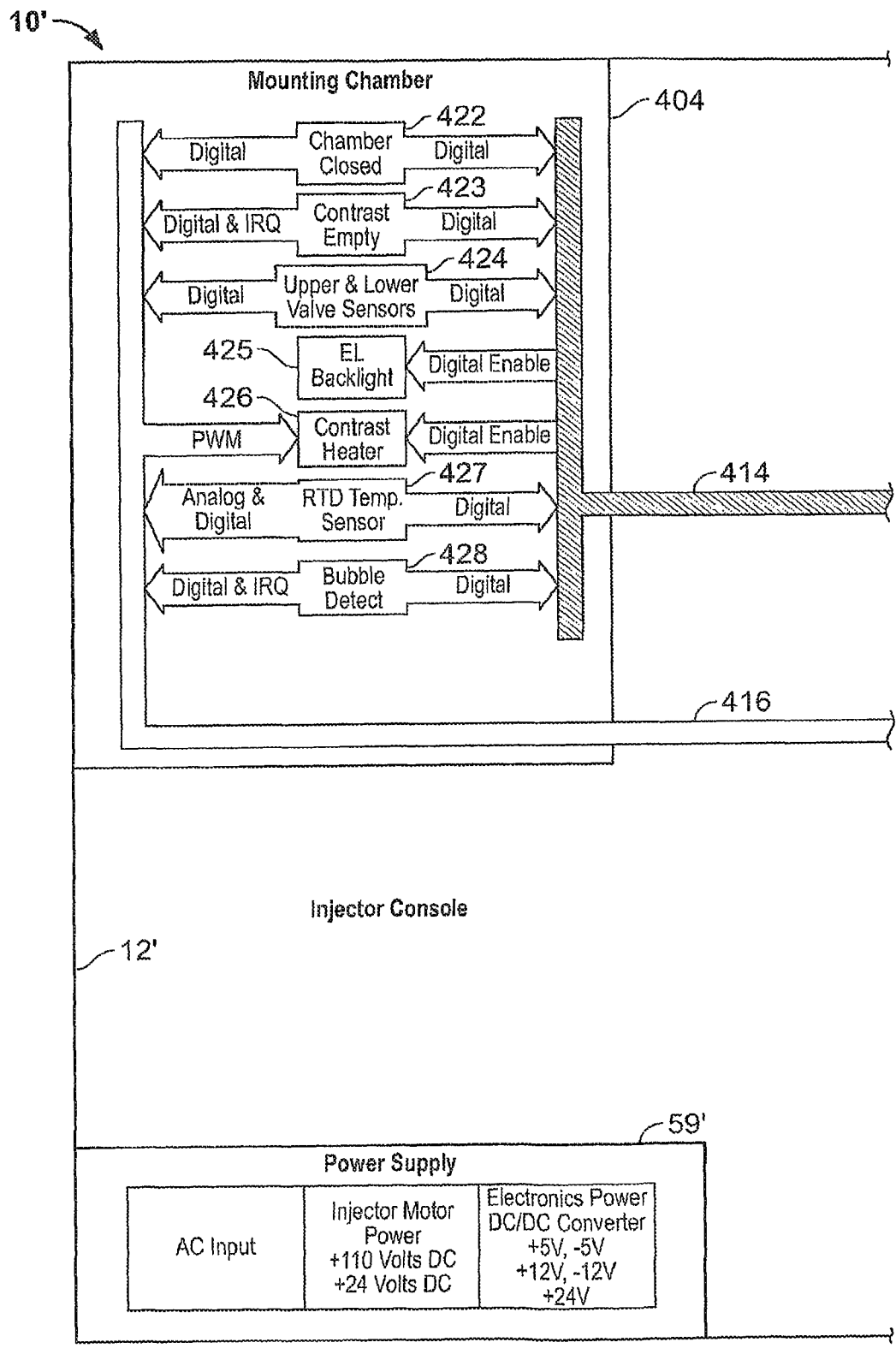

An electrical functional block diagram of a second preferred control configuration for the angiographic injector system 10' is illustrated in FIG. 11. The multiple figures (FIG. 11a and FIG. 11b) collectively comprise the electrical control network of the angiographic injector system 10'. For ease of description of the FIG. 11 network, numbers previously used for comparable electrical components of the first embodiment will not necessarily be duplicated in the description of similarly functioning electrical components of FIG. 11. Referring to FIG. 11, the control system includes two separate computer systems, each having intelligence for monitoring and controlling functions of the injector system. As with the prior embodiment, the computer system generally receives input signals from the control panel 400 and provides signals to display data, alerts, status information and operator prompts. In the preferred embodiment, the computer system comprises two micro-computers. A PC processor, generally indicated at 410 acts as the master processor of the control system, and an embedded processor, generally indicated at 412, acts as the slave processor. In general, the master processor instructs the embedded processor to perform commands, but both processors monitor the actions taken. Both processors serve as independent monitors of action, for safety. Key functions such as the injector motor movement and peristaltic motor movement are monitored by both micro-computers. In the preferred embodiment, the PC processor 410 has a 386 DOS central processing unit, and the embedded core processor 412 has an HC16 bit central processing unit. It will be appreciated that other types of microprocessors can be used within the spirit and intent of this invention.

Referring to FIG. 11, it will be noted that PC processor 410 communicates with electrical components throughout the system by means of a first communication bus 414, and the embedded core processor 412 communicates with electrical circuits throughout the system by means of a second communication bus 416. The two processors communicate with one another by means of their respective buses and a pair of communication registers generally indicated at 417 and 418. General "watch dog/power fail/reset" functions are indicated by the functional block 419, and ECG acquired information can be collected on a first-in first-out basis by the functional block 420 for processing by both microprocessors. In general, the type of communication between the various electrical functional blocks of the system and the two buses 414 and 416 as indicated by the individual signal flow paths of FIG. 11 which are associated with the respective electrical functional blocks and by the signal flow notations within those signal flow paths.

Referring to FIG. 11, the various electrical and sensing functions associated with the mounting chamber 404 include: a sensor entitled "chamber closed" (422) that indicates when the front loading chamber door used to load the disposable syringe into the mounting chamber is closed; a contrast bottle sensor indicated by "contrast empty" (423) which is located within the bottle holder and indicates whether fluid is present in the bottle; two valve sensors, indicated as "upper & lower valve sensors" (424) that are used by the computer to determine the state of the patient manifold valve and contrast valve; an electroluminescent back light, indicated by "EL backlight" (425) which facilitates manual bubble detection within the syringe and disposable items; a heating element, indicated by "contrast heater" (426) located inside the syringe holder adjacent to the syringe body; a pair of temperature sensors, indicated by "RTD Temp Sensor" (427) positioned near the syringe body for providing signals to control the contrast heater for maintaining the contrast material at a relatively constant temperature; and an air column detection sensor, indicated by "bubble detect" (428) positioned to sense air in the high pressure line which monitors fluid that is pumped to the patient for any bubbles or air columns. As indicated in FIG. 11, except for the EL backlight 425, each of the sensors in the mounting chamber communicate with both of the processors.

In general, the control panel 400 includes an arm light 430, a speaker 431, a touch screen 432, a display 433, and an emergency switch 434. The arm light 430 is lit when the injector is ready to perform an injection. The speaker 431 is an optional feature which can provide audible interface communication with the user. The display 433 is in the preferred embodiment a liquid crystal (LCD) panel which is used to display the operational state of the system. The touch screen 432 is overlayed on the LCD panel and is used by the user to control the system, as will be described in more detail hereinafter. All of the functions of the control panel communicate directly with the PC processor 410. The emergency switch 434 communicates directly with both of the communication buses 414 and 416 as well as with cutoff relays and the injector motor solid state relay hereinafter described.

The hand control functional block 14' includes the circuit functions of the remote hand control unit. As previously described, the hand controller is a device used to control the angiographic injector pump in a manner such that when actuated by a user, outputs an electrical signal which is proportional to the displacement of the hand controlled device. The controller is a passive electromechanical device that communicates with both of the microprocessors as indicated in FIG. 11. The hand controller contains a pair of scaled on-contact sensors that can remotely determine position of an object and which are used to determine the active travel distance and placement of the hand movable portion of the controller. The sensors are indicated by the two functional blocks indicated as "analog Hall effect" (440) and "digital Hall effect squeeze" (441). The saline reset function is indicated by "saline reset button" (442), and the functional block indicated as "control type and connected" (443) provides for a setting indication through the hand controller to the microprocessors as to whether the system is being used to perform a "fixed rate" or "variable rate" injection. Under the variable rate mode of operation, the operator is allowed to vary the instantaneous injection rate by means of the hand controller up to a predetermined maximum flow rate. In the fixed mode of operation, when the operator squeezes the hand controller actuator, the control system will respond by simply injecting the contrast material at the predetermined fixed rate that has been entered into the control system prior to the injection procedure.

The peristaltic pump 44' is driven under the control of the microprocessors through a pump motor and motor driver. The motor driver, generally indicated by the "PWM control circuitry" (450) provides a pulse width modulated control signal to the peristaltic pump motor. The computer provides both forward (Saline) and reverse (Waste) drive signals to the motor driver to operate the pump motor in a forward direction for a saline flush and in a reverse direction for waste aspiration. The peristaltic pump of the preferred embodiment includes an "overspeed overtorque" sensor 451 and "cutoff relays" 452. The overspeed/overtorque sensors 451 provide feedback signals to the microprocessors for accurately controlling the speed of the peristaltic pump by way of the pump drive circuits 450. The cutoff relays 452 can be activated by either of the microprocessors or by the emergency stop switch 434.

The injector motor 460 is operatively connected to move the piston or wiper within the syringe and is controlled by a "motor controller" amplifier (461). In the preferred embodiment, the motor driver 461 is an off-the-shelf servo amplifier which can be accurately controlled by means of a nested loop control configuration, hereinafter described. In general, the motor amplifier provides a drive signal to the motor in response to a control voltage. Forward, reverse and break signals come from the computer, and a speed feedback signal from an optical encoder is used to control the speed. Monitoring of the motor status is generally indicated by the functional block entitled "motor status overspeed/overtorque" (462) and an independent optical encoder sensor for sensing the motor speed and position, indicated by the "encoder" functional block (463). A potentiometer is used to provide a back-up signal to the embedded microprocessor indicating the absolute "position" of the motor. The potentiometer is indicated in the block diagram as the "absolute position pot." functional block (464). The outputs of the optical encoder and potentiometer are supplied to the processors as speed monitor and position monitor signals and allow the computers to check motor speed, motor direction and position. A pair of forward and reverse limit sensors sense the end limit positions of the syringe piston and are indicated by the functional block entitled "F/R limit switches" (465). When the piston reaches its forward limit position, no further forward movement is permitted. Similarly, when the reverse limit sensor indicates that the piston has reached its reverse limit position, no further reverse movements are permitted. The injector motor control also includes a solid state relay (470) for disabling the injector motor under command from either of the processors or the emergency switch 434.

The power supply 59' provides all electrical power to the system and includes an externally selectable voltage range switch 59a' enabling selection of connection of the power supply to either 110-120 volts AC or 220-240 volts AC. In the preferred embodiment, the line voltage operating frequency must be between 47 and 63 Hz, and the line voltage must be capable of carrying ten amps of current. The power supply further includes a power indicator light 59b' an on/off switch 59c' and a cable connector 59d' providing a connector for a cable leading to the circuits within the chassis 12'.

Figure 12:
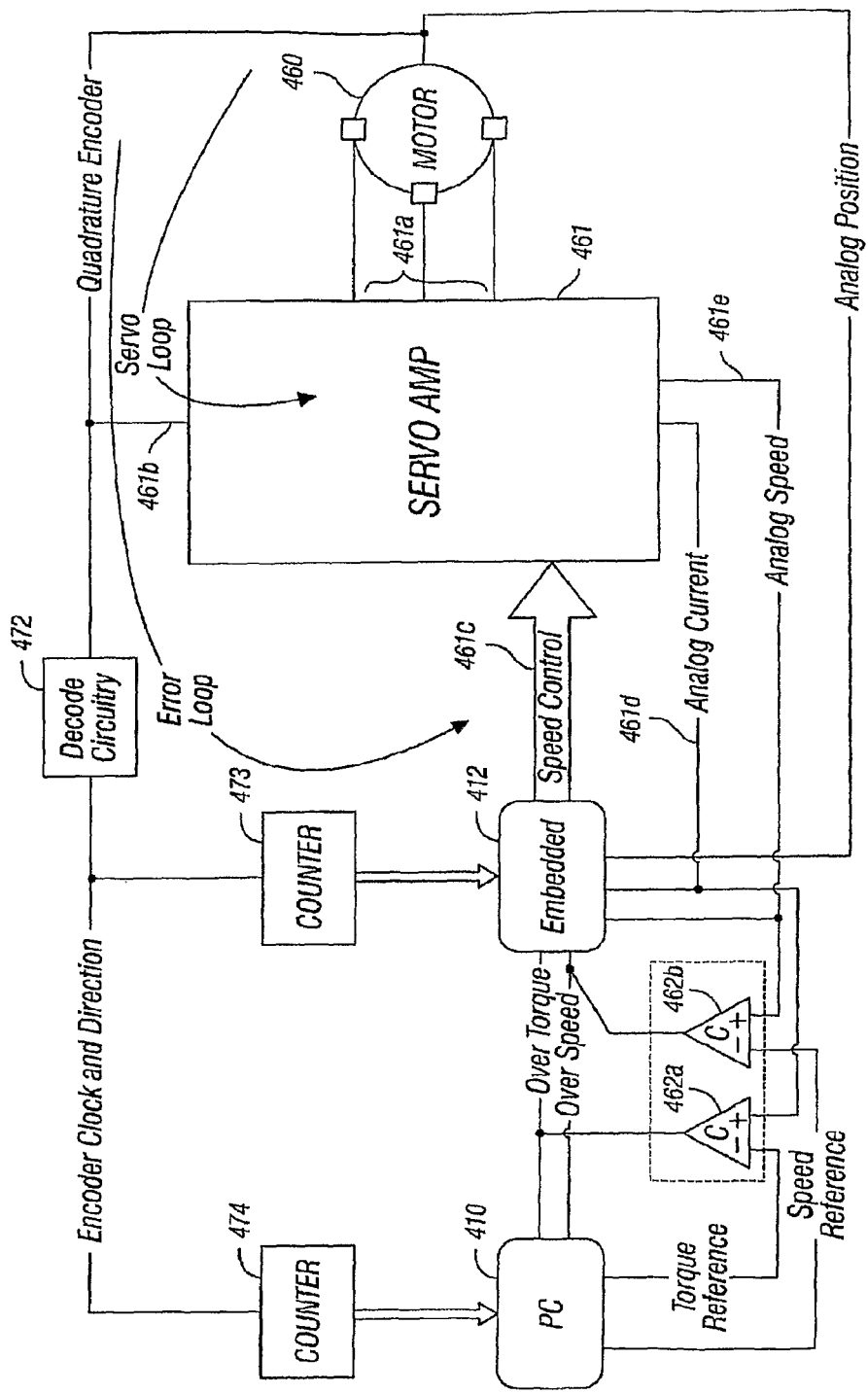
FIG. 12 is an electrical block diagram of the injector motor control portion of the control system of FIG. 11.

A more detailed electrical functional block circuit network for a preferred nested control loop configuration for control of the injector motor 460 is illustrated in FIG. 12. Referring thereto, the injector motor 460 is in the preferred embodiment, a brushless DC motor controlled by the servo amplifier network circuit 461. In the preferred embodiment, the servo amplifier network 461 is a BE30A Series PWM Brushless Servo Amplifier model BE25A20 designated to drive a brushless DC motor at a high switching frequency. In the preferred embodiment, the servo amplifier uses a quadrature encoder feedback input signal for velocity control. The servo amplifier has an output drive port generally indicated at 461a, a feedback signal input port 461b, a speed control signal input port 461c and a pair of analog output signal ports 461d and, 461c respectively. The output port 461d carries a voltage signal developed within the servo amplifier that is proportional to the pressure or torque of the motor 460, and provides a signal to an output feedback line referred to as the "Analog Current" line. The output port 461c carries a voltage signal developed within the servo amplifier that is proportional to the speed of the motor 460, and provides a signal to the line indicated as "Analog Speed". An optical quadrature encoder (not illustrated in FIG. 12) is operatively connected to the output drive of the injector motor 460 (and indicated at 463 in FIG. 11), provides a pulse train feedback signal back to the feedback input port 461*b* of the servo amplifier 461 to provide accurate speed control of the motor 460 through the servo amplifier 461. This loop is referred to as the first loop or the "Servo Loop" in the figure. In the preferred embodiment, the servo amplifier 461 is an off-the-shelf amplifier that provides very accurate control of the speed of the injector motor 460 through this standard Servo Loop configuration and requires little further control. The quadrature encoder signal is also fed back through a signal conditioning Decode Circuit indicated at 472 to a pair of counters 473 and 474 which respectively provide cumulative count signals to the embedded processor 412 and the PC processor 410 respectively. The Analog Current and Analog Speed signals from the output ports 461*d* and 461*c* respectively of the servo amplifier 461 are directly fed as input signals to the embedded processor 412 and are respectively applied to first signal inputs of comparators 462*a* and 462*b* of the "motor status overspeed overtorque" functional block 462. The reference signal inputs for the comparators 462*a* and 462*b* are connected to receive input signals from the PC processor 410 corresponding to "torque reference" and "speed reference" input signals.

The comparators 462*a* and 462*b* respectively compare the feedback signals received from the servo amplifier 461 with the reference voltage signals received from the PC processor 410 and provide signal outputs representing "overtorque" and "overspeed" respectively to both the embedded processor 412 and the PC processor 410, as indicated in FIG. 12.

During an injection procedure, the master PC processor 410 instructs the embedded processor 412 to perform the injection. As part of this command, the embedded processor is told by the PC processor what the desired flow rate and maximum pressure allowed conditions are. Immediately prior to the PC processor issuing the injection command, it sets reference voltage values in the two comparators 462*a* and 462*b*, one being representative of the maximum flow rate the embedded processor is allowed to achieve and the other representing the maximum allowable pressure. During the injection, the "Analog Current" and the "Analog Speed" feedback signals from the servo amplifier 461 are fed back to the comparators 462*a* and 462*b*. If either of these feedback signal voltages exceed the respective reference voltages of the comparators, an appropriate output signal is provided by the triggered comparator, back to both of the processors. If either processor receives one or both signals from the comparators, that processor will cut power to the injector motor 460, immediately stopping the injection.

During an injection, the embedded processor 412 uses the digital encoder 463 to determine the current position of the ram or syringe piston. In the preferred embodiment, for each millimeter of contrast material injected 1,317 counts are received from the encoder 463. As the piston moves during an injection, the embedded processor looks at the current position of the ram or piston every ten milliseconds. The embedded processor then calculates the theoretical position of the ram based on a simple trapezoidal type move. If the current position is more than a predetermined number of millimeters different than the actual position, the injection is stopped and error is reported.

The potentiometer 464 which provides the "Analog Position" signal is used in a similar fashion, however its tolerance is higher. During ram or piston movement calibration, the system calculates a constant that is representative of the number of ohms per millimeter of movement. During the injection, the embedded processor uses the same theoretical trapezoidal move to determine the theoretical position of the piston. As with the digital encoder process, if the current position of the ram is more than a predetermined number of ohms different than the actual analog position reading, the injection is stopped and an error is reported.

Accordingly, a nested loop control network is established wherein the primary direct Servo feedback loop control of the motor 460 is supplemented by the "Error Loop" control provided through the encoder signal which is fed back through the decoder circuitry 472 and counter 473 and embedded processor 412 back to the signal input terminal 461*c* of the servo amplifier 461. The first or "servo loop" is a standard velocity control loop that uses proportional integration; whereas the outer "error loop" is a position control loop which simply periodically checks on the servo loop control to ensure that the servo loop is accurately controlling the motor speed. The potentiometer which is operatively connected to the gear train output of the motor 460 is an absolute position sensor that simply acts as a back-up to the encoder loop. Similarly, the encoder feedback to the PC processor 410 through counter 474 acts as a redundant back-up to the primary error loop control through embedded processor 412, should the processor 412 fail to operate in its intended manner in providing speed correction signals through the secondary "error loop".

As briefly described above, the availability of multiple processors provides the capability of true multi-redundancy sensing using intelligence in both sensing circuits. In addition, the dual or multiple processor feature provides the capability for redundant control and monitoring safety features of key functions of the system such as injection motor movement and peristaltic motor movement. Both of these conditions are actively monitored by both microprocessors as described above, and as indicated in FIGS. 11 and 12. For example, an "overspeed safety circuit" for the injection motor is provided by the quadrature encoder 463 feeding signals through the decode circuitry 472 and the pair of counters 473 and 474 to the two processors. The use of two independent processors for receiving the encoder information acts as a safety circuit for sensing the flow rate, since both the embedded and PC processors count pulses to determine the injection flow rate. As stated above, the individual counts are accumulated over a specified time interval and the average speed is computed. The safety feature is provided by the fact that either processor may independently shut down the injector motor based on its own decision making capability, in the event of an overspeed condition. Such redundant sensing path dual processor control allows for safety monitoring in the event of a single component failure.

Similarly, an "over volume safety circuit" is provided, by the same hardware used to provide the over-speed safety circuit. The pulses provided through counters 473 and 474 from the encoder to the embedded and PC processors allow both processors to independently count pulses to determine injection volume. Either processor may independent shut down the injector motor in the event of an over-volume condition.

A further dual safety feature, which does not require multiple processors, is provided by the "analog position" signal received from the potentiometer 464 which allows the embedded processor to check the volume by reading the change in the analog voltage output from the potentiometer.

By providing the potentiometer as a back-up for the quadrature encoder, further dual redundancy safety is provided for sensing the injection volume.

Dual redundant motor safety circuits are provided as previously described for the injector motor "over current" and "overspeed" conditions. These circuits were previously described with respect to comparators 462a and 462b. The comparator 462a uses the "analog current" feedback signal from the servo amplifier 461 to provide dual input signals to both the embedded and PC processors to provide dual processor current measurement safety circuit sensing. Similarly, comparator 462b applies dual input signals to both of the processors as the result of the "analog speed" signal from the servo amplifier 461 to provide dual redundant sensing of the injector motor speed.

Figure 13:
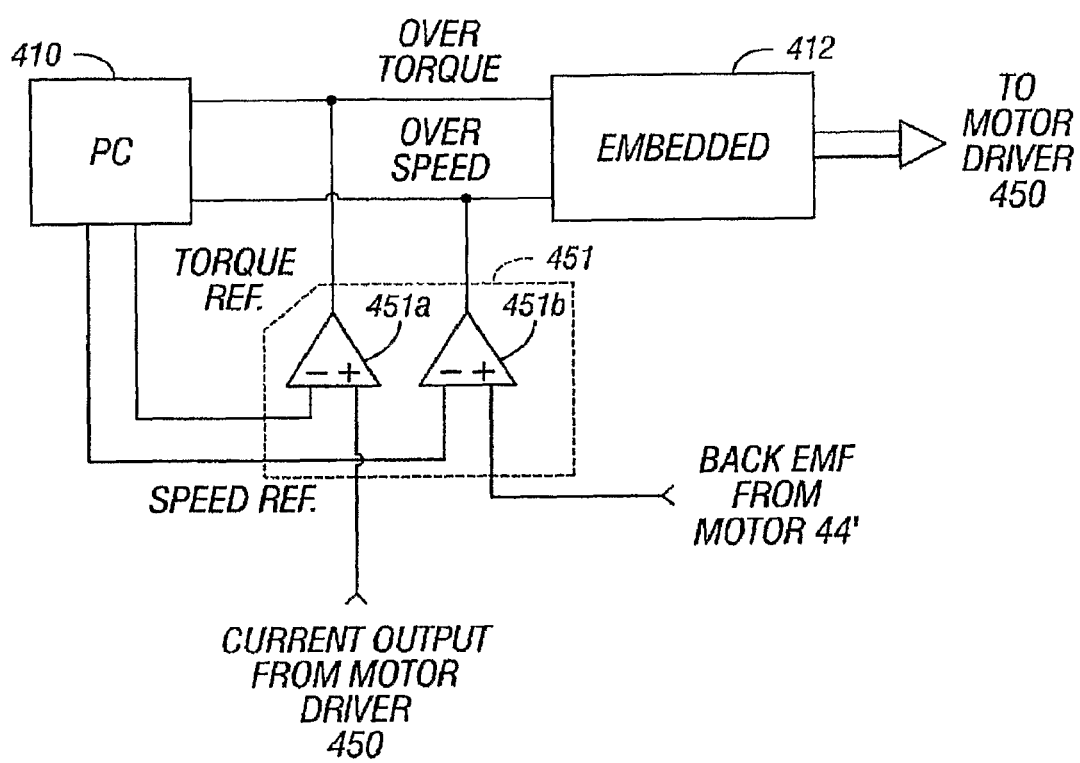
FIG. 13 is an electrical block diagram of the safety circuits associated with the peristaltic pump motor control portion of the control system of FIG. 11.

Similar safety circuits are provided for control of the peristaltic pump 44'. As indicated in FIG. 11, the peristaltic pump also includes an overspeed/overtorque network 451. In the preferred embodiment, the peristaltic pump 44' is not a brushless motor like the injection motor, and receives a pulse width modulated input signal from the PWM control circuitry 450. Pump motor 44' develops a back EMF that can be sensed and used as a feedback signal along with the output current from the motor driver circuit 450. An electrical block diagram representation of the peristaltic pump safety circuits is illustrated in more detail in FIG. 13. Referring thereto, the PC and embedded processors are indicated at 410 and 412 respectively. The safety circuit illustrated in FIG. 13 is virtually identical to that used for sensing the speed and current of the injector motor. A pair of comparators 451a and 451b of the overspeed/overtorque network 451 are used in manner similar to the comparators 462a and 462b previously described with respect to the safety circuits of the injector motor. The comparator 451a provides an overtorque output signal to both of the processors, and the comparator 451b provides an overspeed input signal to both of the processors. Comparator 451 receives a torque reference voltage signal from the PC processor 410 and the comparator 451b receives a speed reference voltage signal from the processor 410. The comparator 451a monitors a current output signal from motor driver network 450 and provides an output signal whenever the monitored current output signal exceeds the torque reference signal provided from processor 410. The comparator 451b monitors a back EMF signal from motor 44' and provides an output signal whenever the back EMF signal exceeds the speed reference voltage signal applied by processor 410. The embedded processor 412 provides the primary drive control signal to the motor driver 450.

In the embodiment of the invention illustrated in FIG. 9, all operator/user interface with the system is performed through the control panel, except for turning on the power supply and activation of the emergency stop switch. Communication with the processor or processors of the system is performed through switches on the touch screen 432 overlying the display 433. The computer generates various screens on the display, with appropriate simulated switch indicators that align with touch pads on the touch screen, which enable the operator to communicate with the microprocessor(s) through the touch screen. When power is initialized to the system, the control panel display will communicate to the user that the system is performing self diagnostic tests. Following the diagnostic and calibration tests, the display will illustrate various set-up windows providing a series of instructions for the operator that will guide the operator through the step-by-step set-up procedure, generally including syringe loading, locking and filling, disposable connections, and flushing.

Figure 14:
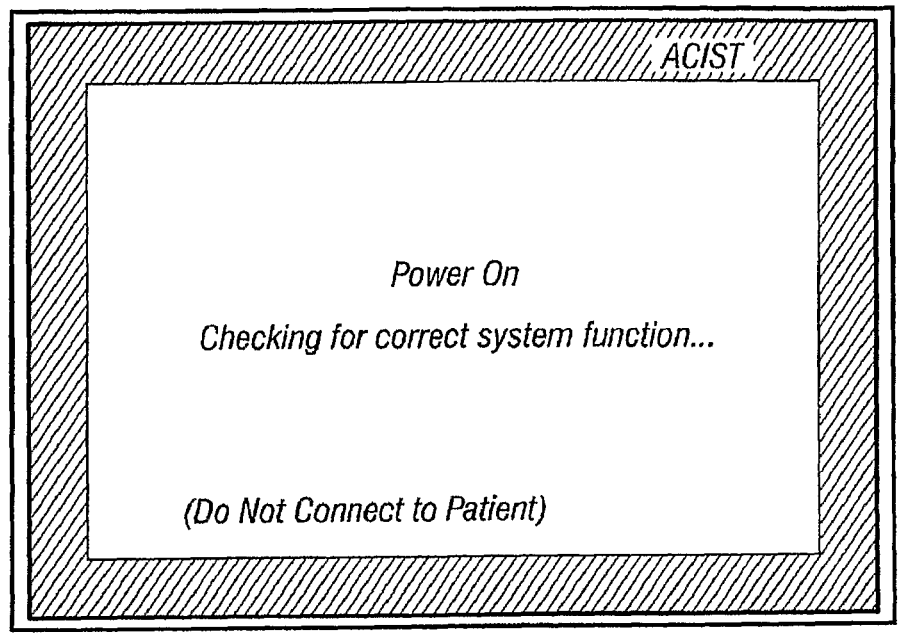
FIG. 14 is an illustration of a Power Up screen of the display of the system of FIG. 11.
Figure 15:
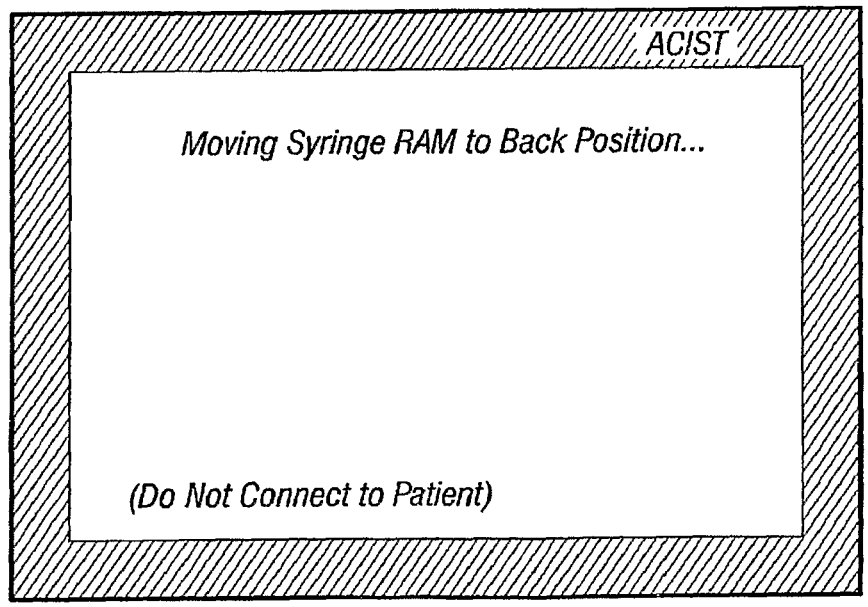
FIG. 15 is an illustration of a Back Calibration screen of the display of the system of FIG. 11.
Figure 16:
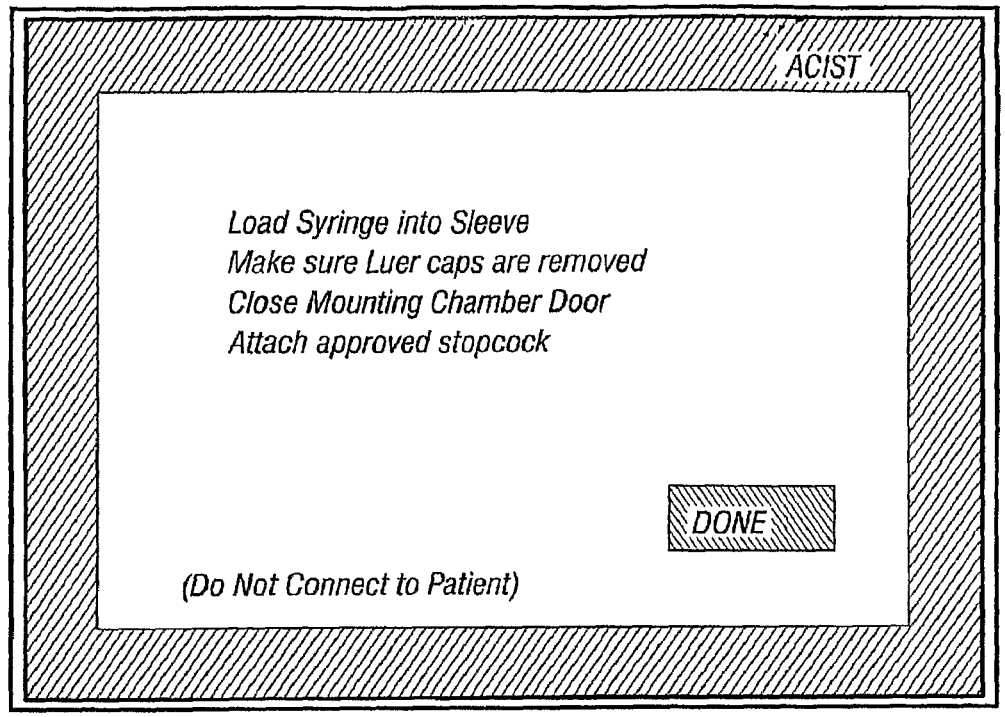
FIG. 16 is an illustration of a Check Screen of the display of the system of FIG. 11.
Figure 17:
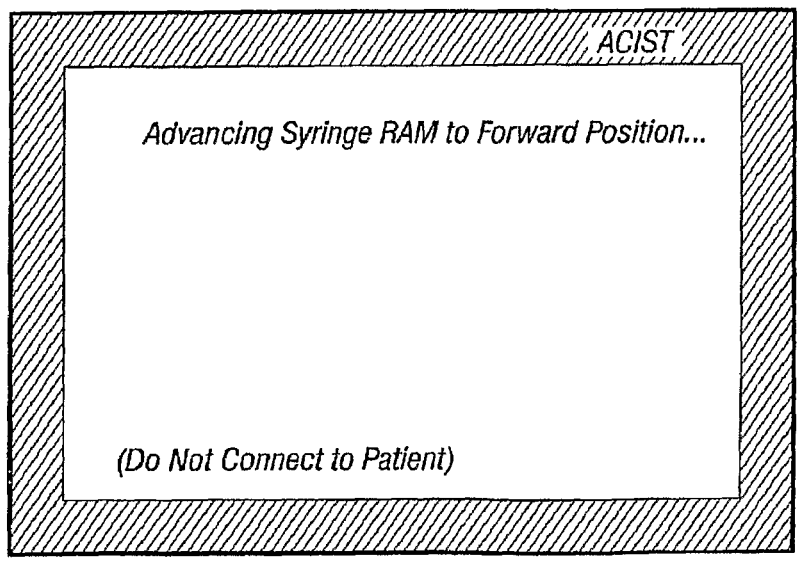
FIG. 17 is an illustration of a Forward Calibration screen of the display of the system of FIG. 11.

Sample screens that are generated by the PC processor and which are displayed to the user for the power-up, calibration and self diagnostic functions are illustrated in FIGS. 14-17. Referring thereto, the initial Power-up screen is illustrated in FIG. 14. This screen remains visible while the system runs in an internal diagnostic check to make sure all functions are working properly. The system will then automatically begin set-up and calibration. The screen of FIG. 15 will appear as the syringe ram moves to a back position, after which the screen of FIG. 16 will be displayed which instructs the operator how to load the syringe assembly. Upon completion of the syringe loading sequence, the operator pushes the "Done" pad on the touch screen of FIG. 16. The system is now ready to begin the "set-up" procedure, and displays the screen of FIG. 17 while the syringe ram is moved to its forward position.

Figure 18:
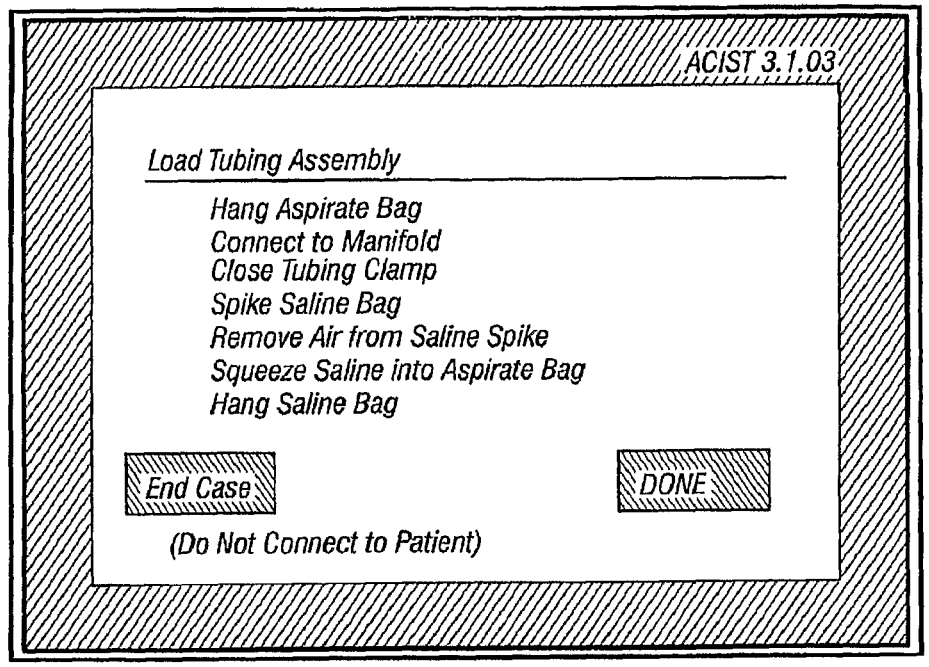
FIG. 18 is an illustration of a First Start-Up Instruction screen of the display of the system of FIG. 11.
Figure 19:
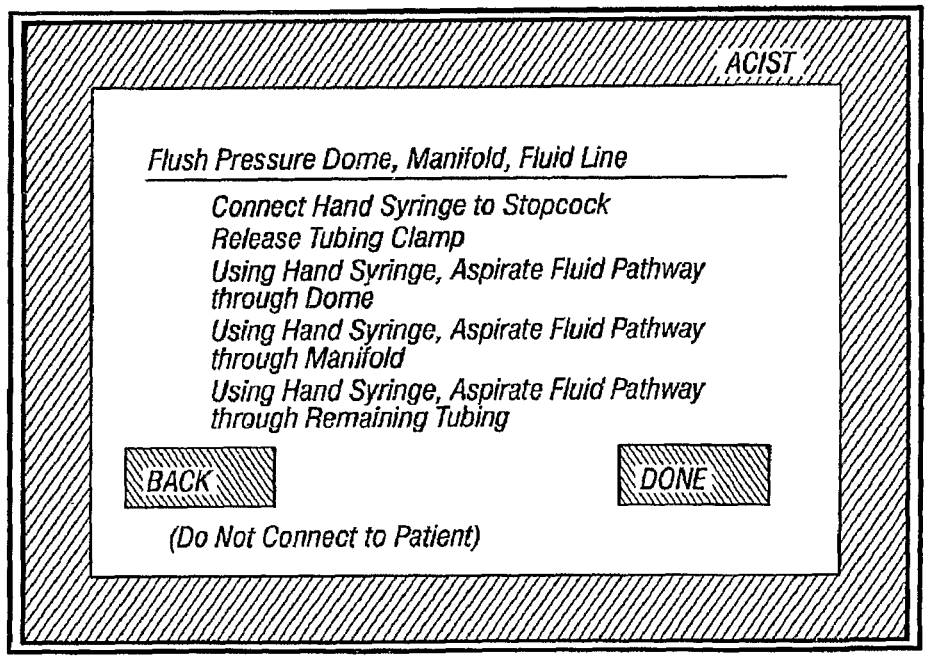
FIG. 19 is an illustration of a Second Start-Up Instruction screen of the display of the system of FIG. 11.
Figure 20:
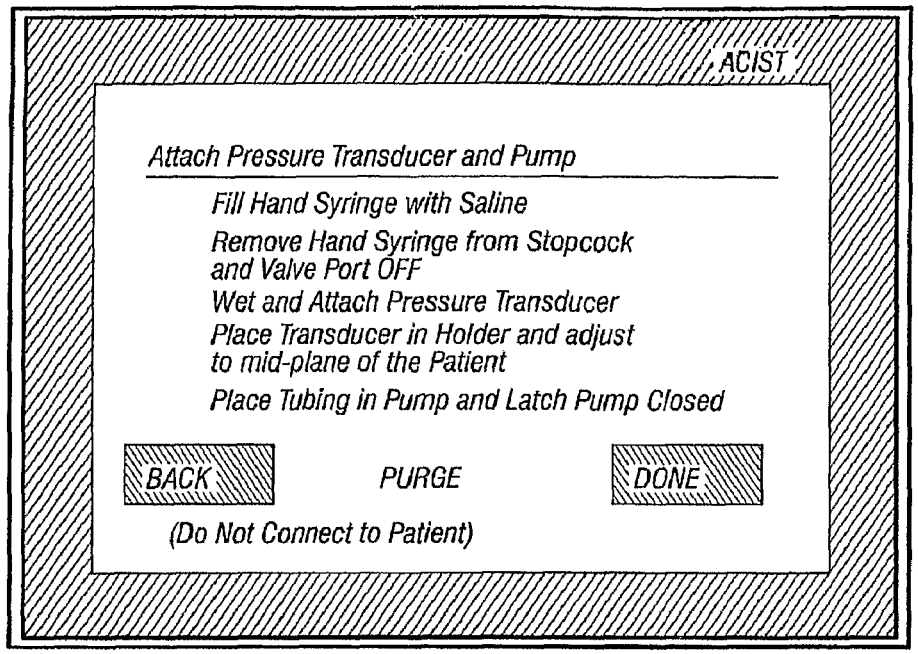
FIG. 20 is an illustration of a Third Start-Up Instruction screen of the display of the system of FIG. 11.
Figure 21:
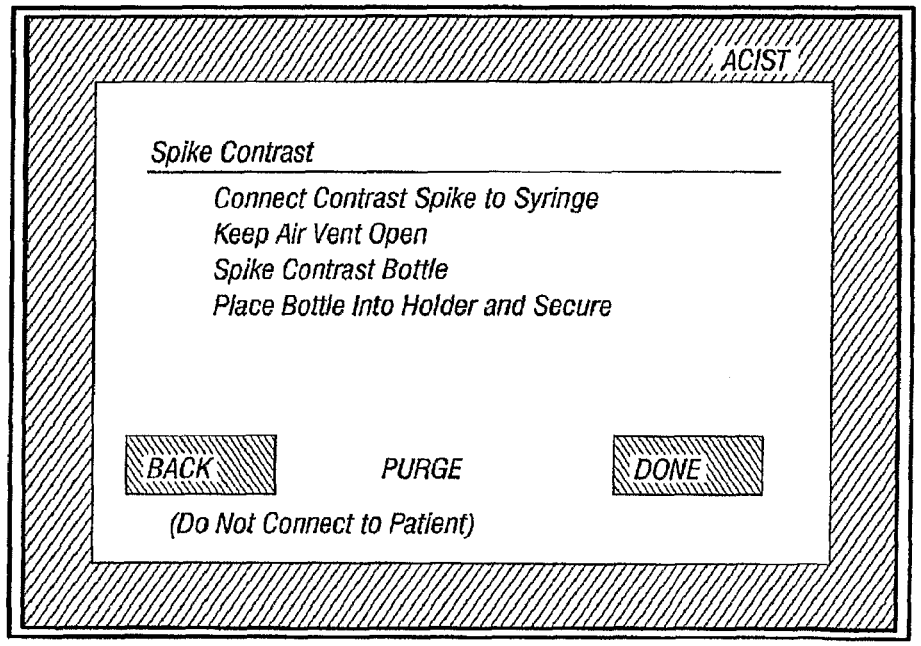
FIG. 21 is an illustration of a Fourth Start-Up Instruction screen of the display of the system of FIG. 11.

The "set-up" instructions begin with the screen of FIG. 18. Referring thereto, the operator is instructed in a step-by-step manner as to how to load the tubing assembly portion of the system. When the operator has completed the steps identified in FIG. 18, he activates the touch screen by pushing the "Done" switch, and proceeds to the steps indicated on the screen of FIG. 19. The screen of FIG. 19 includes flushing operations of the pressure dome, manifold and fluid lines. When these steps have been completed and the "Done" switch has been activated, the set-up instruction screen of FIG. 20 will be displayed. Screen 20 provides instructions for attaching the pressure transducer and pump assemblies of the system. Upon completion of the FIG. 20 screen items and activation of the "Done" switch, the set-up instructions of the screen of FIG. 21 will be displayed. The steps of FIG. 21 complete the set-up instructions, and when the operator activates the "Done" switch of the FIG. 21 screen, the system is ready to fill the syringe. It will be noted that during all of the set-up steps included on the screens of FIGS. 18-21, the operator has the option of reverting to a prior screen by pushing the "Back" switch area on the screen.

Figure 22:
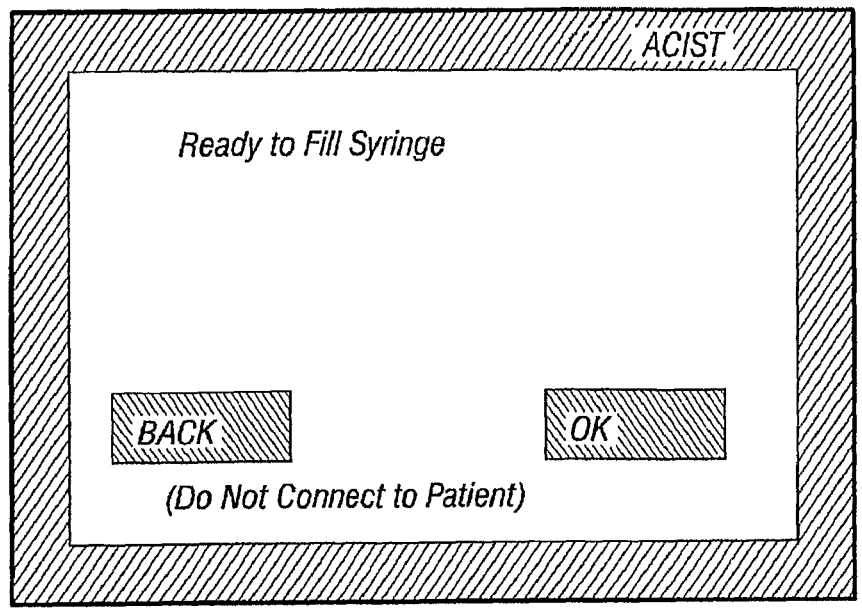
FIG. 22 is an illustration of a Ready to Fill Syringe screen of the display of the system of FIG. 11.
Figure 23:
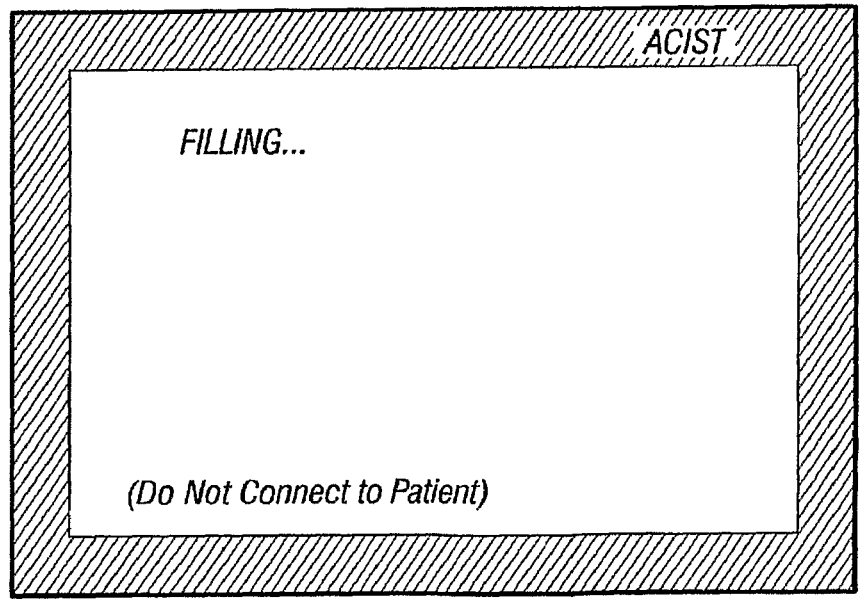
FIG. 23 is an illustration of a Syringe Filling Notice screen of the display of the system of FIG. 11.
Figure 24:
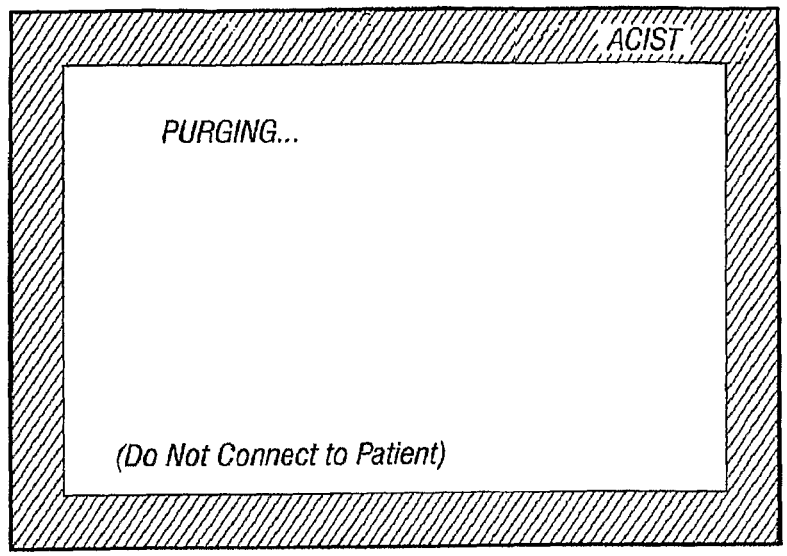
FIG. 24 is an illustration of a Purging Notice screen of the display of the system of FIG. 11.
Figure 25:
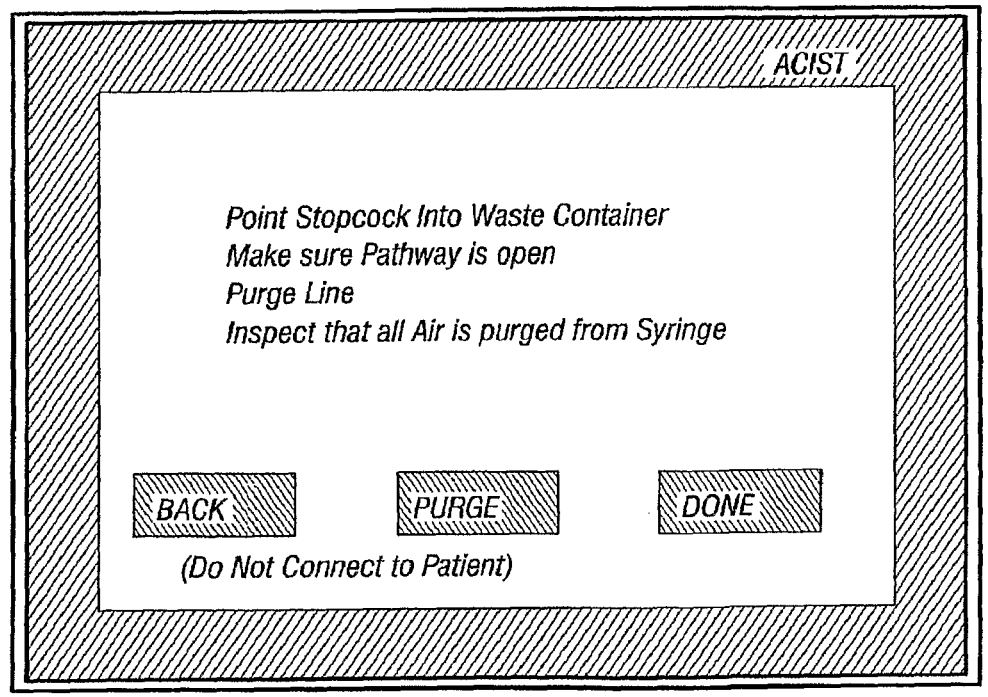
FIG. 25 is an illustration of a Line Purge Instruction screen of the display of the system of FIG. 11.
Figure 26:
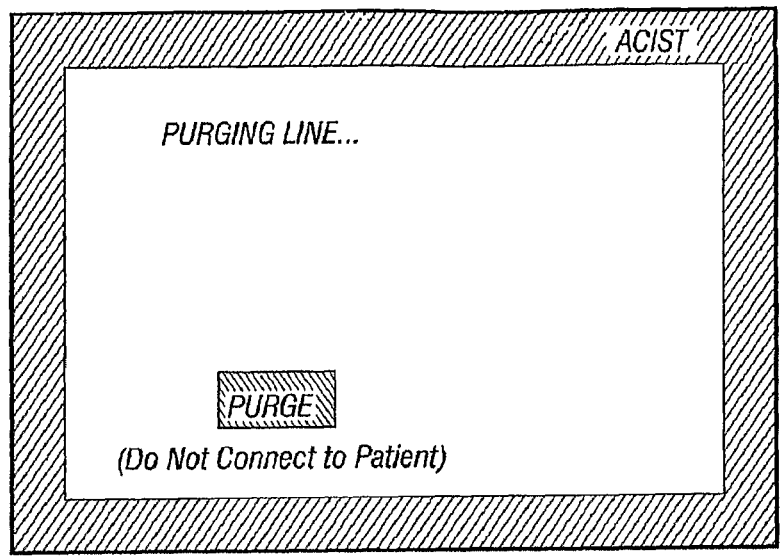
FIG. 26 is an illustration of a Purging Line Notice screen of the display of the system of FIG. 11.

Upon completion of the set-up instructions, before the system proceeds with filling of the syringe, the operator must activate the "OK" switch of the screen of FIG. 22. Upon activation of the "OK" switch, the system will proceed through an automated filling and purging operation. As the syringe piston is withdrawn to the rear of the syringe, drawing contrast material into the syringe, the screen of FIG. 23 will be displayed. Then, as the piston reverses direction and begins moving forward, air will be purged out of the upper port of the syringe, during which time the screen of FIG. 24 will be displayed. The syringe piston automatically stops before the lower valve within the patient manifold moves. Following the syringe purge operation, the screen of FIG. 25 will be displayed, providing instructions to the operator as to how to proceed with the purging of the line from the syringes lower port to the system's high pressure line. In order to purge the line, the operator must press and hold the "Purge" switch of the FIG. 25 screen and visually observe the purging process as air and bubbles are pushed out of the line between the syringe and the patient manifold, and from the front/nose of the patient manifold and out into the high pressure line. When this procedure has been completed, the operator releases the "Purge" switch and activates the "Done" switch of the FIG. 25 screen. When the operator is engaging the "Purge" switch, the screen of FIG. 26 will be displayed. When the operator releases contact with the "Purge" switch, the screen of FIG. 25 will reappear. After the "Done" switch of FIG. 25 has been activated, the display screen of FIG. 27 will be displayed.

Figure 27:
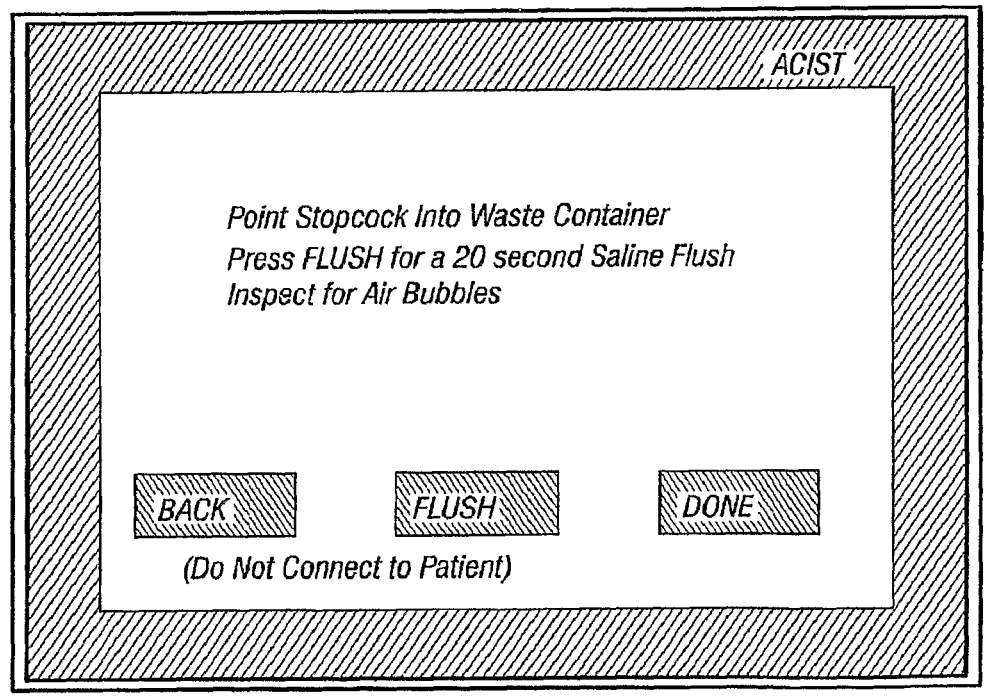
FIG. 27 is an illustration of a Final Saline Flush Instruction screen of the display of the system of FIG. 11.
Figure 28:
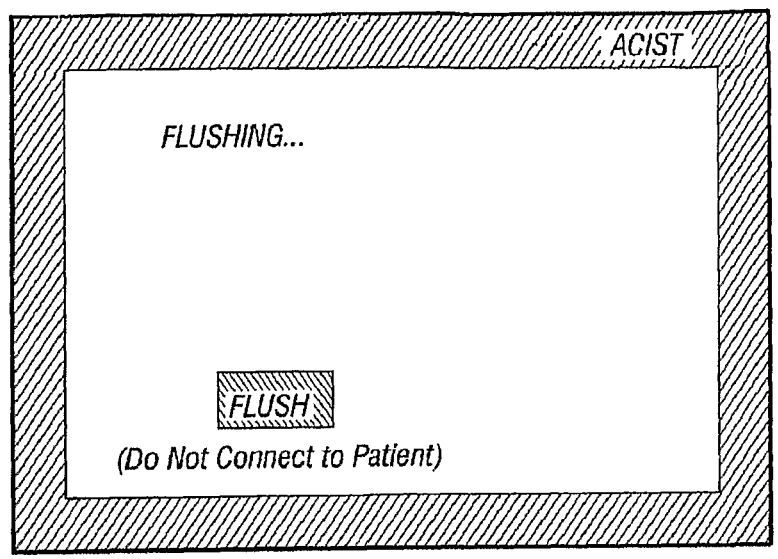
FIG. 28 is an illustration of a Saline Flushing Notice screen of the display of the system of FIG. 11.
Figure 29:
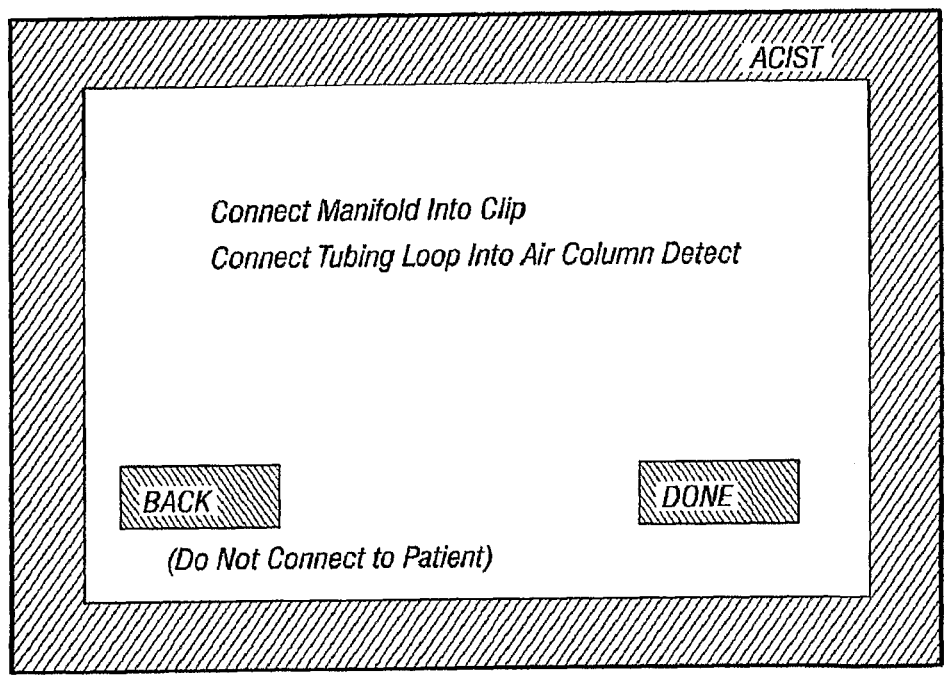
FIG. 29 is an illustration of a Final Start-Up screen of the display of the system of FIG. 11.

The FIG. 27 process steps relate to the final saline flush procedure. When the operator engages the "Flush" switch of the FIG. 27 screen, the system will flush the line from the saline bag to the stopcock, assuring that no air bubbles are present in the line. As long as the operator continues to engage the "Flush" switch of the FIG. 27 screen, the screen of FIG. 28 will be displayed. Upon completion of the final saline flush procedure, the operator will release the "Flush" switch and engage the "Done" switch of the screen of FIG. 27, which will cause the display screen of FIG. 29 to be displayed. The FIG. 29 screen is the final start-up screen. Following completion of the instructions of the FIG. 29 screen, the operator activates the "Done" switch of the display, completing the start-up procedure, and the system is now ready for connection to a catheter.

Figure 30:
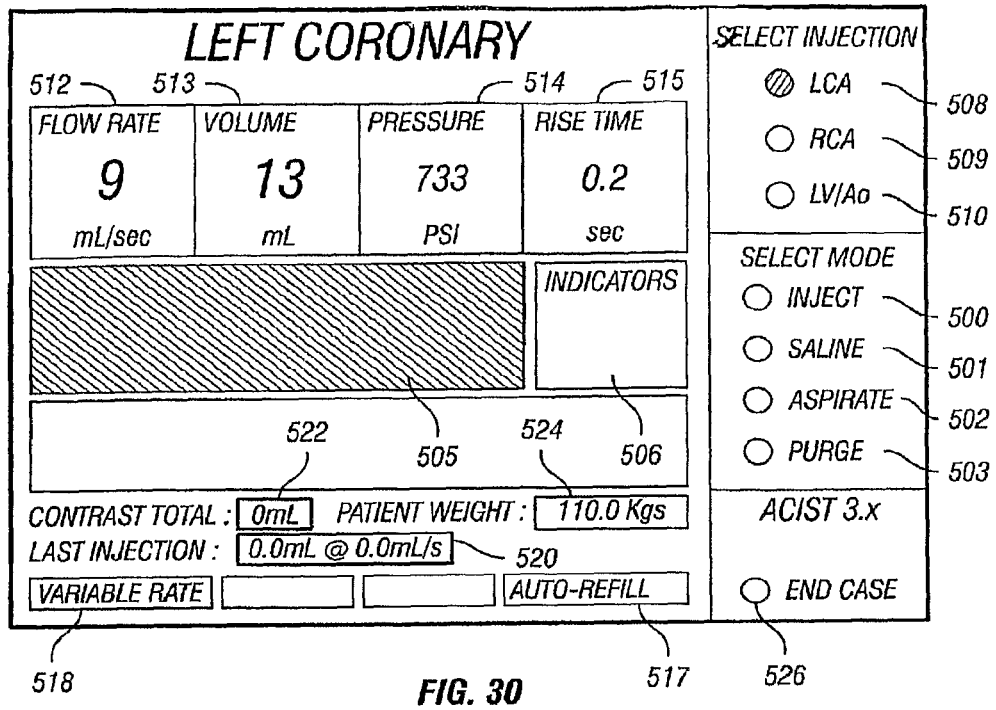
FIG. 30 is an illustration of the MAIN display screen of the system of FIG. 11.

Upon successful completion of the start-up procedure described above, the system displays the MAIN screen, generally indicated in FIG. 30. The MAIN display screen of the control panel of a preferred configuration thereof is divided into sections as illustrated in FIG. 30. It will be appreciated that all of the formatting for the display screen is provided by and under control of the PC microprocessor 410. Referring to FIG. 30, there are four "function keys" vertically aligned along the right side of the screen and designated as "Inject" (500); "Saline" (501); "Aspirate" (502); and "Purge" (503). The icons for these four function soft keys are aligned with appropriate switch pads of the touch screen 432 so that an operator can press selected ones of the function keys and bring up the status window for the chosen function. The Status window is indicated at 505, and an Indicator window is located at 506. The Status window is used to display system messages and to provide feedback to the user on the state of system operations. The Status indicator window 506 displays key system sensors when they are active.

Three "Injection Type" or "Select Injection" keys indicated as LCA (left coronary artery) 508; RCA (right coronary artery) 509; and LV/Ao (left ventricle/aorta) 510 are positioned above the function keys and provide operator input as to the type of injection procedure that will be performed. The injection type can be changed by simply pressing one of these three type buttons. When a new type is selected, the default parameter values for the selected type are calculated and displayed in the parameter keys. In the preferred embodiment (as hereinafter described in more detail) the injection parameters are calculated based on actual values such as weight of the patient to be treated. A verbal indication of the selected injection key is indicated at the very top of the display screen. In the sample screen indicated in FIG. 30, the LCA key has been selected and its associated indication "LEFT CORONARY" is displayed at the top of the screen.

The following parameters can be changed by pressing the icon of the desired parameter while the Injection Status window is open, or during the set-up procedure: Flow Rate; Injection Volume; Injection Pressure; and "Rise Time". The injection parameter/limit keys are located along the top of the display screen.

A "Flow Rate" window 512 displays the greatest flow rate obtainable if the hand remote controller is completely depressed. The units for flow rate are ml/sec. An "Injection Volume" panel 513 displays the total volume limit that can be injected during a single injection. The units for this parameter are ml. An "Injection Pressure" window 512 displays the maximum pressure within the syringe allowed during an injection. If this pressure is reached, a warning light will come on and the injection flow rate will be limited to the indicated pressure. The units for pressure are psi. A "Rise Time" window 515 displays the maximum rise time allowed during an injection. The units for rise time are seconds.

The system has the unique ability to either automatically or manually refill the syringe, as described in U.S. Pat. No. 5,800,397, entitled Angiographic Injector System with Automatic High/Low Pressure Switching", which is hereby incorporated by reference. The "Refill" key is located in the lowermost portion of the display screen comprises the "Options" portion of the display screen. The Refill key, generally indicated at 517 can be reset at any time during a case or procedure by simply pressing the desired icon.

A second Option key generally indicated as the "Rate Type" key is located at 518 which permits selection of the injection procedure as either a "Fixed" rate or a "Variable" rate which can be controlled in real time by the remote hand controller 14'.

Figure 31:
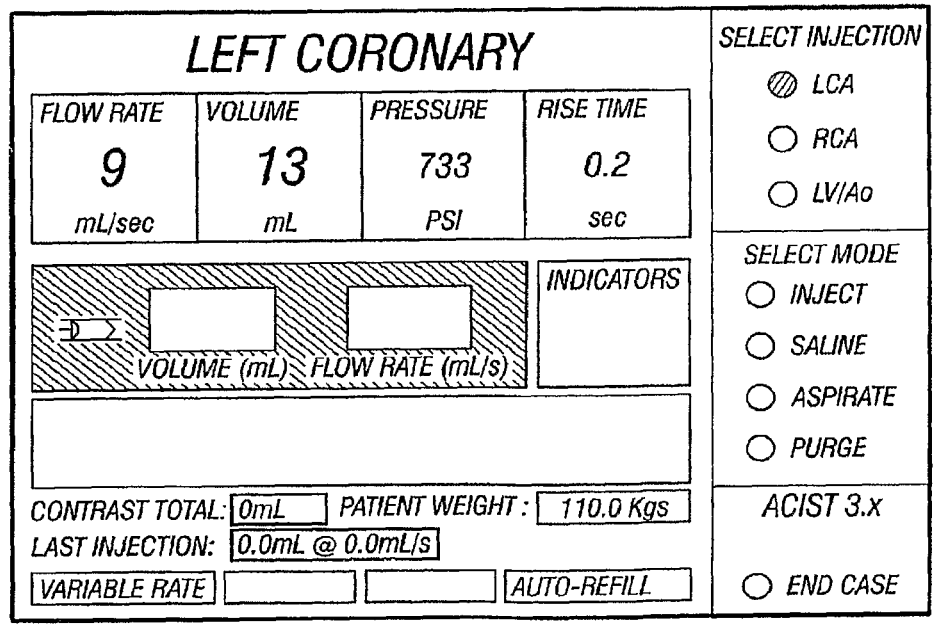
FIG. 31 is an illustration of the MAIN display screen of FIG. 30 illustrating operation in an injecting mode.

The processor provides real-time information to the user on the instantaneous conditions existing during an injection procedure. These conditions are displayed in the Status window 505 as indicated on the sample screen of FIG. 31. The display panel also displays the results of the last injection in a "Last Injection" window 520. The last injection results include the "total volume" and the "maximum flow rate" of the last injection performed. The display panel also indicates the cumulative total of contrast material that has been injected in a patient for the current case, indicated in the "Contrast Total" display window 522. The Last Injection and Contrast Total display windows are located near the lower left portion of the display screen. The Contrast Total display provides important information to have instantaneously available during the injection procedure, since a case procedure may involve numerous filling procedures of the syringe. Further, such filling procedures may represent either total or only partial filling of the syringe. Prior techniques depended upon the operator/user for maintaining a log of the total amount of contrast material that had been administered to a patient over the course of successive injections. Failure to maintain an accurate cumulative total for the amount of contrast material injected can result in overdose of injected material to the patient.

In the preferred embodiment, a display window/key indicated as a "Patient's Weight" is indicated at 524. In the preferred embodiment, this display window displays the weight of the current patient. Selection of this key will allow the user to enter a patient's weight in kilograms into the system. The patient weight is used to calculate injection values and limits (hereinafter described in more detail).

The final key on the display panel is the "End Case" key 526 located near the lower right portion of the display panel. Activation of this key will prompt the user through the proper steps before shut-down of the system or before starting a new case.

The Emergency button or switch 434 (FIG. 11) is physically located on the upper right hand portion of the control panel. This is the only functional switch (besides the Power Supply switches) which is not located on the display screen. The Emergency switch disables any on-going function and displays a message in the status window that the emergency button is engaged. The emergency button or switch is an alternate action type of switch. When engaged, the button is lit. To disengage the switch the user must press the button again.

The injection limits can be changed by pressing the key (512-515) of the desired parameter. If the injection (key 518) is set to a "Fixed" mode, a keypad will be presented to the user in the status window. This condition is illustrated in FIG. 32. A new value can now be entered. This new value will be checked by the processor to see if it within an acceptable range for the type of ejections elected. If the entered value is out of the acceptable range, a message will be displayed indicating this fact to the user. If the "Cancel" key is pressed, the previously set value will remain set. If the injection option (key 518) is set to the "variable" mode, a choice of six different values are displayed in the status window for the user to select. A sample display window corresponding to this situation is illustrated in FIG. 33. If the "Cancel" key is pressed, the previously set value will remain set.

An Injection is initiated by pressing the "Inject" button or key 500. If the LV/Ao (large injection button), is selected, the user will be asked to confirm this. The LV/Ao injection procedure represents the largest volume use of contrast material; whereas the RCA injection procedure uses the least amount of contrast material. The user is then asked by prompt on the display if it is okay to "Arm" the injection. The user must press the "OK" key in the status window. At this point, if there is not enough contrast in the syringe to perform the requested injection, the system will prompt for a refill. The refill will be automatic or manual, depending on the status of the "Refill" option key 517. When the volume level is correct, the user will be prompted to activate the hand controller 14' for initiating the injection procedure.

If the volume injected is less than 10% of the volume limit, the number of injections will not increase and the hand controller will remain armed. A "large" injection requires the user to press "Large OK" again before another injection is permitted. The user exit the inject function by pressing any key on the screen.

The Saline Flush function, initiated by activation of the "Saline" key 501, pulls saline from the saline bag and flushes the disposable and line connections. When this function is initiated, the "Saline Flush" status window will be displayed with a "Flush" key and a "Done" key. Pressing the "Flush" key will flush the disposable with saline for up to 10 seconds or until the user stops pressing the key. Pressing the "Done" button in the window will end the flush process and return the user to the "MAIN" screen.

The Aspirate function draws line fluid back into the waste bag from the catheter through the disposable. It may be used to remove bubbles if they are detected in the line. The aspirate function is initiated by selecting the "Aspirate" button or key 502 on the display panel. The "Aspirate" status window will be displayed on the screen. Pressing the "Aspirate" key will pull line fluid back through the disposable into the waste bag as long as the "Aspirate" key is depressed, for up to 10 seconds. Pressing the "Done" button will return the user to the "MAIN" screen.

Figures 34, 35:
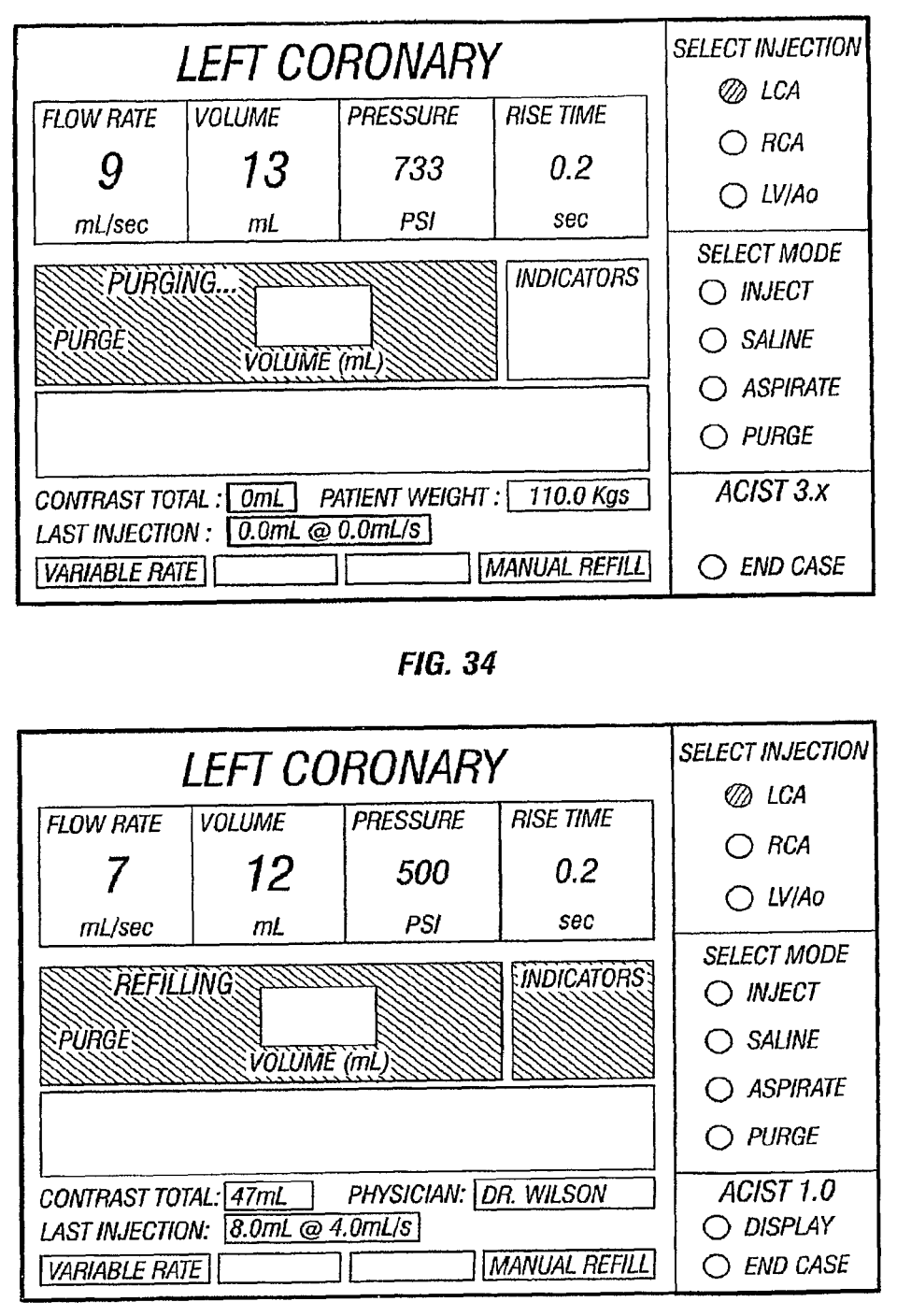

The manual purge function is used to flush air from the disposable. There are two choices when purging, comprising the Syringe Purge and the Line Purge. Syringe Purge involves purging air out-of the syringe and will be stopped when air has been purged from the syringe and the fluid pushes the syringe check valve closed. Line Purge purges air from the syringe to the stopcock through the patient manifold. This method will send contrast material through the disposable and will disengage the bubble detection device. This purge is done at system start-up in order to clear air out of the interconnect of the syringe to the patient manifold and the front on the patient manifold valve. During a procedure, Line Purge may also be used when an air bubble remains within the disposal after the aspirator flush procedures have been tried. To access the "Purge" function, the "Purge" key 503 is selected from the "MAIN" screen. The "Purge" status window will be displayed. Three options are presented on the screen: "Syringe", "Cancel", and "Line". Selecting "Cancel" will return to the "MAIN" screen. If "Line" is selected, the user is warned to disconnect the patient. The user must acknowledge this by pressing the "okay" key. At this point, or if "Syringe" has been selected, a "Purge" key and "Done" key are displayed in the window. The "Purge" key is a press and hold key which will initiate and continue the purging through the line or syringe until the user releases the key, for up to 10 seconds. The purge will stop automatically if the air is completely purged out and the contrast valve is successfully closed. If the user stops the purge before the valve closes, a message will indicate that the purge is not complete. Pressing the "Done" key or any other key on the screen will exit the purge function. A sample screen for a manual purge function is illustrated in FIG. 34.

If the automatic refill option is chosen by means of the key 517, the syringe will automatically refill to 110 ml. if there is not enough contrast media within the syringe for the desired injection volume limits. This will occur automatically at the time of injection. If manual refill is chosen, the "Refill" status window will be displayed. A "Purge" key, a "Done" key, and a "Refill" key are active in this window. Pressing and holding down the "Refill" key will draw the plunger back, filling the syringe. The current amount of contrast media in the syringe is displayed as it fills. When the "Refill" button is released, the refilling operation discontinues. Pressing the "Purge" key will purge air and fluid out of the syringe as long as the "Purge" key is depressed. Pressing the "Done" button will send the user back to the "MAIN" screen. If there is still not enough contrast in the syringe to satisfy the injection value of limits, the "Refill" status window will re-open at the time of injection. A sample screen for the manual refill operation is illustrated in FIG. 35.

To end a case, the "End Case" button 526 is activated. A "Cancel" key and an "End" key are displayed in the status box. If the "Cancel" key is selected, the user is returned to the "MAIN" screen. If the "End" key is selected, the end case sequence begins. When the high pressure line is disconnected and the contrast container is removed from the receptacle, the "No Contrast" indicator will appear. If the "Done" button is then depressed or selected, the plunger is automatically withdrawn from the syringe body and the syringe can be removed from the system by unlocking and opening the chamber.

Prior systems have not provided automated determination of default injection parameters that are directly related to values or characteristics of the patient to be treated. Such characteristics might include such things as weight, age, wellness of the person, vascular robustness, catheter size and the like. For example, prior systems have included memory recall features for stored injection parameter values that may have been stored by a physician for a particular patient or for a particular procedure wherein the stored parameters represent the typical injection parameter choices of that physician. Various embodiments of the present invention provides an automated method for determining suggested default injection parameter values just prior to an injection procedure, which injection parameter values are directly related to values or conditions of the patient to be treated. In a preferred embodiment implementation of this method, the injection parameter default values are calculated using the "weight" of the patient. As stated above, however, other unique patient factors could be used in creating the default value calculations. For a preferred embodiment determination of the default injection parameters based on the patient's weight, three different sets of formulas or algorithms have been used, corresponding to the three different types of injections that can be performed by the system (i.e., LCA, RCA or LV/Ao). For the LCA (Left Coronary procedure), the equations used for determining the four injection parameter default values are:

LCA Flow Rate Limit=3.5 Ln(weight)−7.6    Equation 1

LCA Volume Limit=5.17 Ln(weight)−11    Equation 2

LCA Rise Time=(flow rate+10)/100    Equation 3

LCA Pressure Limit=(flow rate+20)25    Equation 4

Table 1 provides a listing of calculated default injection parameter values determined by Equations 1-4 for selected patient weights.

TABLE 1

LEFT CORONARY DEFAULT PARAMETERS

| WEIGHT (KG) | FLOW RATE (MAX) (ML/SEC) | VOLUME (MAX) (ML) | RISE TIME (MAX) (SEC) | PRESSURE LIMIT (PSI) |
|---|---|---|---|---|
| 10 | 0 | 1 | 0.1 | 511 |
| 20 | 3 | 4 | 0.1 | 572 |
| 30 | 4 | 7 | 0.1 | 608 |
| 40 | 5 | 8 | 0.2 | 633 |
| 50 | 6 | 9 | 0.2 | 652 |
| 60 | 7 | 10 | 0.2 | 668 |
| 70 | 7 | 11 | 0.2 | 682 |
| 80 | 8 | 12 | 0.2 | 693 |
| 90 | 8 | 12 | 0.2 | 704 |
| 100 | 9 | 13 | 0.2 | 713 |
| 110 | 9 | 13 | 0.2 | 721 |
| 120 | 9 | 14 | 0.2 | 729 |
| 130 | 9 | 14 | 0.2 | 736 |

The default injection parameters for a RCA (Right Coronary procedure) preferred embodiment, determined by Equations 5-8:

RCA Flow Rate Limit=2.1 Ln(weight)−4.8    Equation 5

RCA Volume Limit=2.7 Ln(weight)−6    Equation 6

RCA Rise Time=(flow rate+10)/100    Equation 7

RCA Pressure Limit=(flow rate+15)25    Equation 8

Table 2 provides a listing of values of the four injection parameter values determined by Equations 5-8 for selected patient weights.

TABLE 2

RIGHT CORONARY DEFAULT PARAMETERS

| WEIGHT (KG) | FLOW RATE (MAX) (ML/SEC) | VOLUME (MAX) (ML) | RISE TIME (MAX) (SEC) | PRESSURE LIMIT (PSI) |
|---|---|---|---|---|
| 10 | 0 | 0 | 0.1 | 376 |
| 20 | 1 | 2 | 0.1 | 412 |
| 30 | 2 | 3 | 0.1 | 434 |
| 40 | 3 | 4 | 0.1 | 449 |
| 50 | 3 | 5 | 0.1 | 460 |
| 60 | 4 | 5 | 0.1 | 470 |
| 70 | 4 | 5 | 0.1 | 478 |

TABLE 2-continued

RIGHT CORONARY DEFAULT PARAMETERS

| WEIGHT (KG) | FLOW RATE (MAX) (ML/SEC) | VOLUME (MAX) (ML) | RISE TIME (MAX) (SEC) | PRESSURE LIMIT (PSI) |
|---|---|---|---|---|
| 80 | 4 | 6 | 0.1 | 485 |
| 90 | 5 | 6 | 0.1 | 491 |
| 100 | 5 | 6 | 0.1 | 497 |
| 110 | 5 | 7 | 0.2 | 502 |
| 120 | 5 | 7 | 0.2 | 506 |
| 130 | 5 | 7 | 0.2 | 511 |

Default injection parameter values for the LV/Ao injection selection (Left Ventricle/Aorta procedure), for the preferred embodiment, are calculated according to Equations 9-12.

LV/Ao Flow Rate Limit=7 Ln(weight)−16    Equation 9

LV/Ao Volume Limit=22 Ln(weight)−46    Equation 10

LV/Ao Rise Time=(flow rate+10)/100    Equation 11

LV/Ao Pressure Limit=60(flow rate)+200    Equation 12

Table 3 illustrates default injection parameter values determined by 9-12 for selected patient weights.

TABLE 3

LEFT VENTRICLE/AORTA DEFAULT PARAMETERS

| WEIGHT (KG) | FLOW RATE (MAX) (ML/SEC) | VOLUME (MAX) (ML) | RISE TIME (MAX) (SEC) | PRESSURE LIMIT (PSI) |
|---|---|---|---|---|
| 10 | 0 | 5 | 0.1 | 207 |
| 20 | 5 | 20 | 0.1 | 498 |
| 30 | 8 | 29 | 0.2 | 669 |
| 40 | 10 | 35 | 0.2 | 789 |
| 50 | 11 | 40 | 0.2 | 883 |
| 60 | 13 | 44 | 0.2 | 960 |
| 70 | 14 | 47 | 0.2 | 1024 |
| 80 | 15 | 50 | 0.2 | 1080 |
| 90 | 15 | 53 | 0.3 | 1130 |
| 100 | 16 | 55 | 0.3 | 1174 |
| 110 | 17 | 57 | 0.3 | 1214 |
| 120 | 18 | 59 | 0.3 | 1251 |
| 130 | 18 | 61 | 0.3 | 1284 |

Figure 36A:
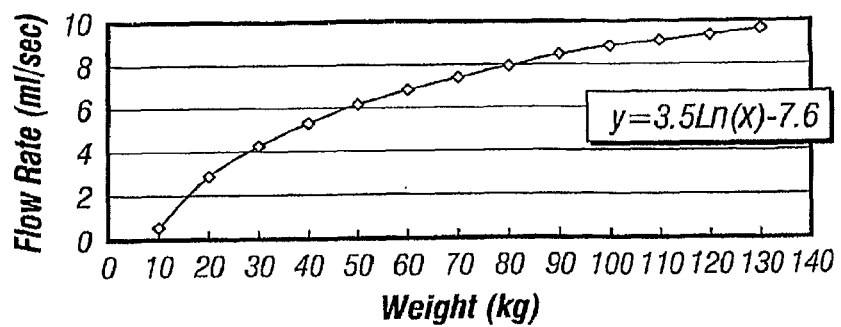
FIGS. 36A-C illustrate comparative graphs for default injection parameter values for Flow Rate Limits determined by algorithms relating to patient weight.
Figure 36B:
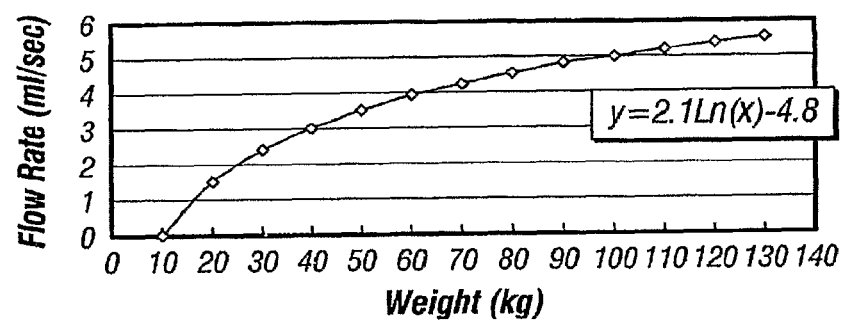
Figure 36C:
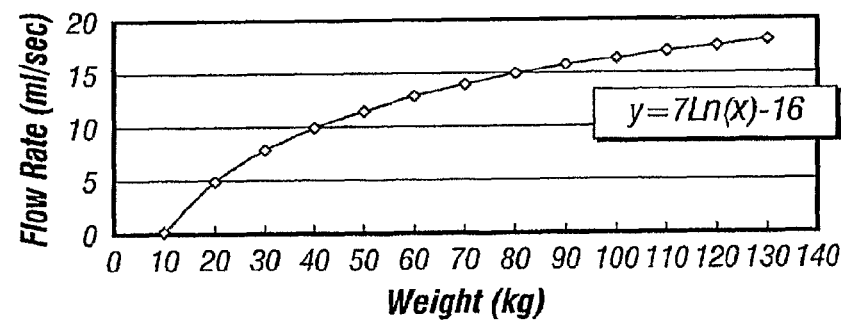

FIG. 36 illustrates comparative graphs for the default injection parameter values for Flow Rate Limits determined according to Equations 1, 5 and 9 respectively for the Left Coronary, the Right Coronary and the Left Ventricle/Aorta functions for patient weights from 10-130 kg.

Figure 37A:
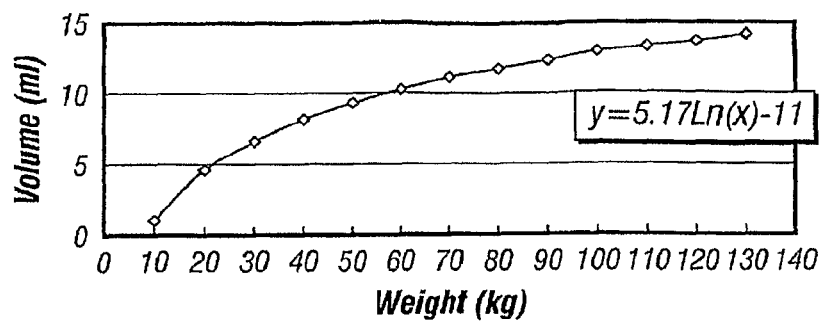
FIGS. 37A-C illustrate comparative graphs for default injection parameter values for Volume Limits determined by algorithms of this invention relating to patient weight.
Figure 37B:
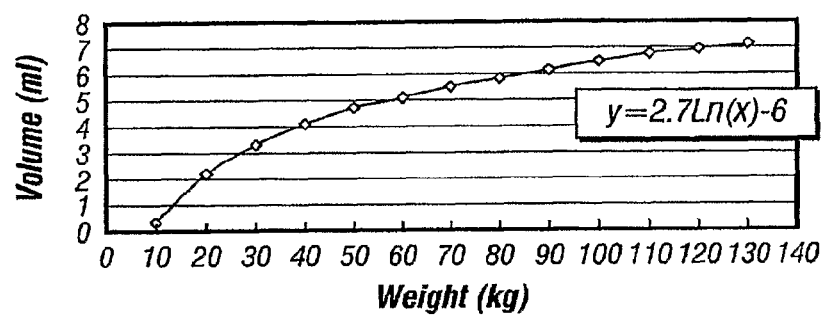
Figure 37C:
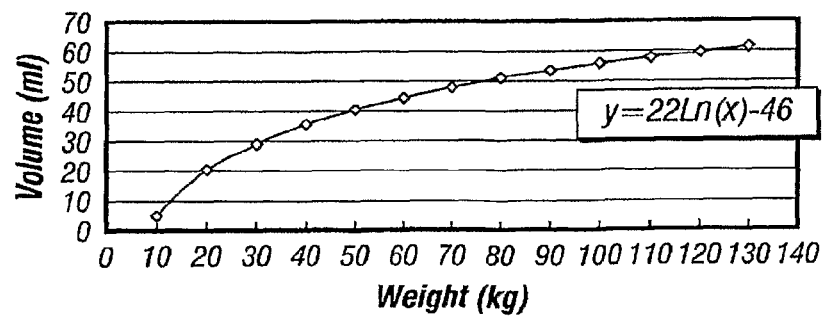

FIG. 37 illustrates comparative graphs of the Volume Limit default injection parameter calculated according to Equations 2, 6 and 10 for the Left Coronary, the Right Coronary and the Left Ventricle/Aorta selections respectively for patient weights ranging from 10-130 kg.

It will be appreciated that the automated determination of default injection parameter values based on the patient's unique characteristics (such as weight), minimizes guess factors associated with selection of proper default parameters for a particular patient, provides a method of determining the default parameters which accommodates changes in the patient's condition between injection procedures and eliminates the requirement for supplemental charts and graphs upon which the physician or operator administering the injection procedure might have to otherwise rely in order to select or determine proper injection parameter default values.

Figure 38:
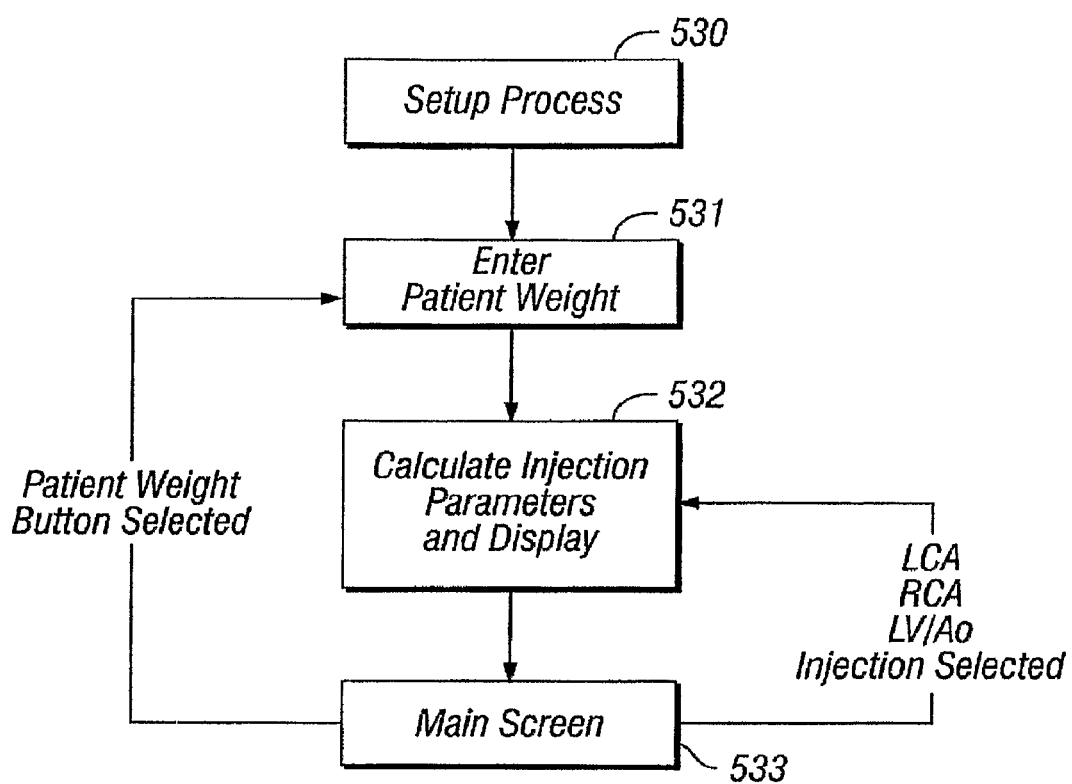
FIG. 38 is a diagrammatic flow chart illustrating the process used to determine the patient related default injection parameters of FIGS. 36 and 37.

Accordingly, in order to determine a set of default injection parameter values for a particular injection procedure, the user need simply select one of the three injection selectors provided by selection buttons 508-510 and to enter the patient's weight in kilograms in the patient weight window 524. A flow chart of this process is illustrated in FIG. 38. Referring thereto, after the initial set-up process which includes an initial selection of the type of injection to be performed (block 530) the operator enters the patient's weight (block 531). The microprocessor automatically determines the default injection parameters by using the appropriate algorithms therefor (block 532) according to the selected injection procedure (i.e., LCA, RCA or LV/Ao) and according to the patient weight entered into the system through the display panel. The calculated default injection parameter values are then displayed on the MAIN screen (block 533) to complete the process. The operator has the option of changing the determined values, but for most applications no changes to the default values will be required.

Figure 39A:
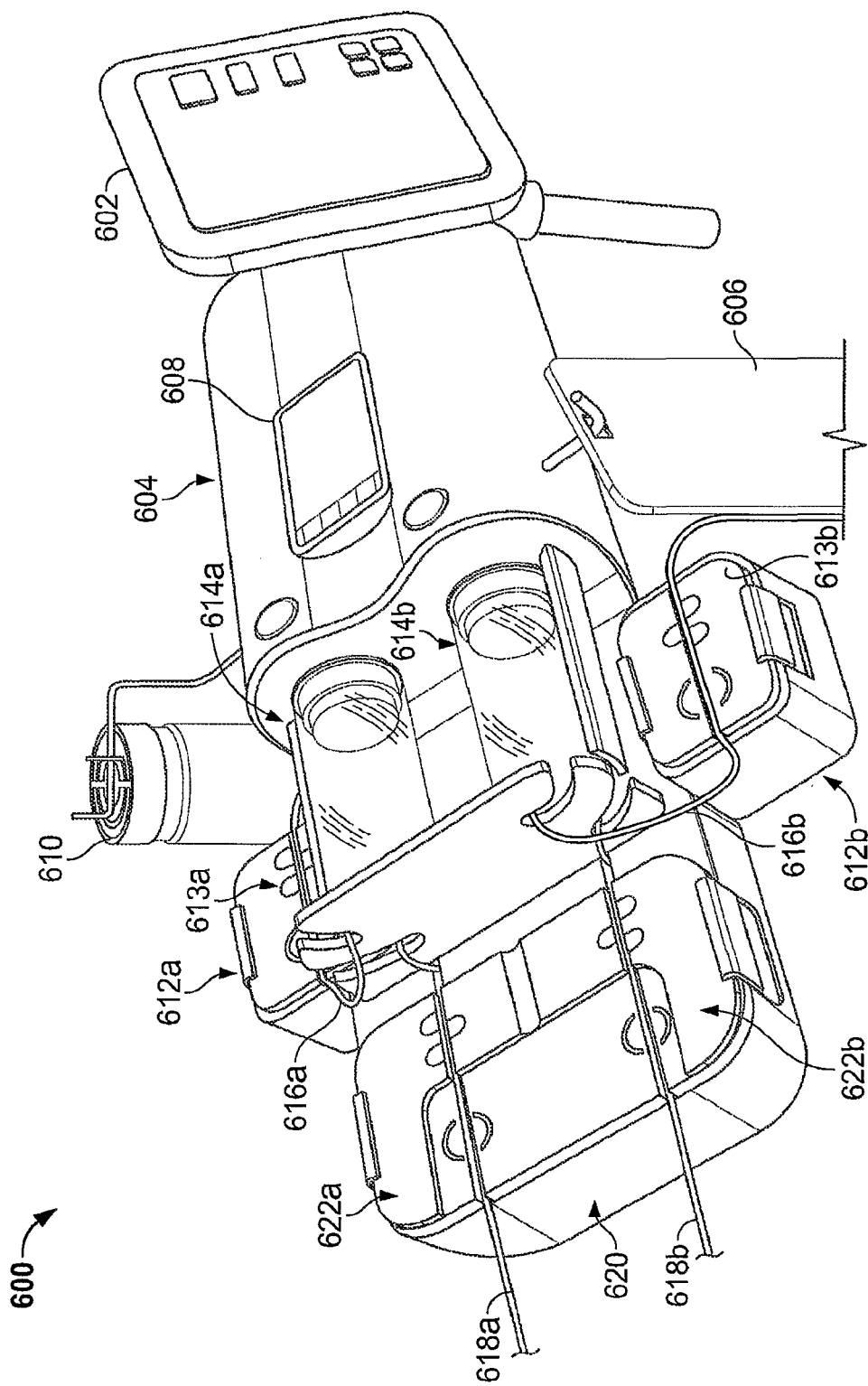
FIGS. 39A-C are views of a powered, dual-syringe contrast injection system, according to one embodiment.
Figure 39B:
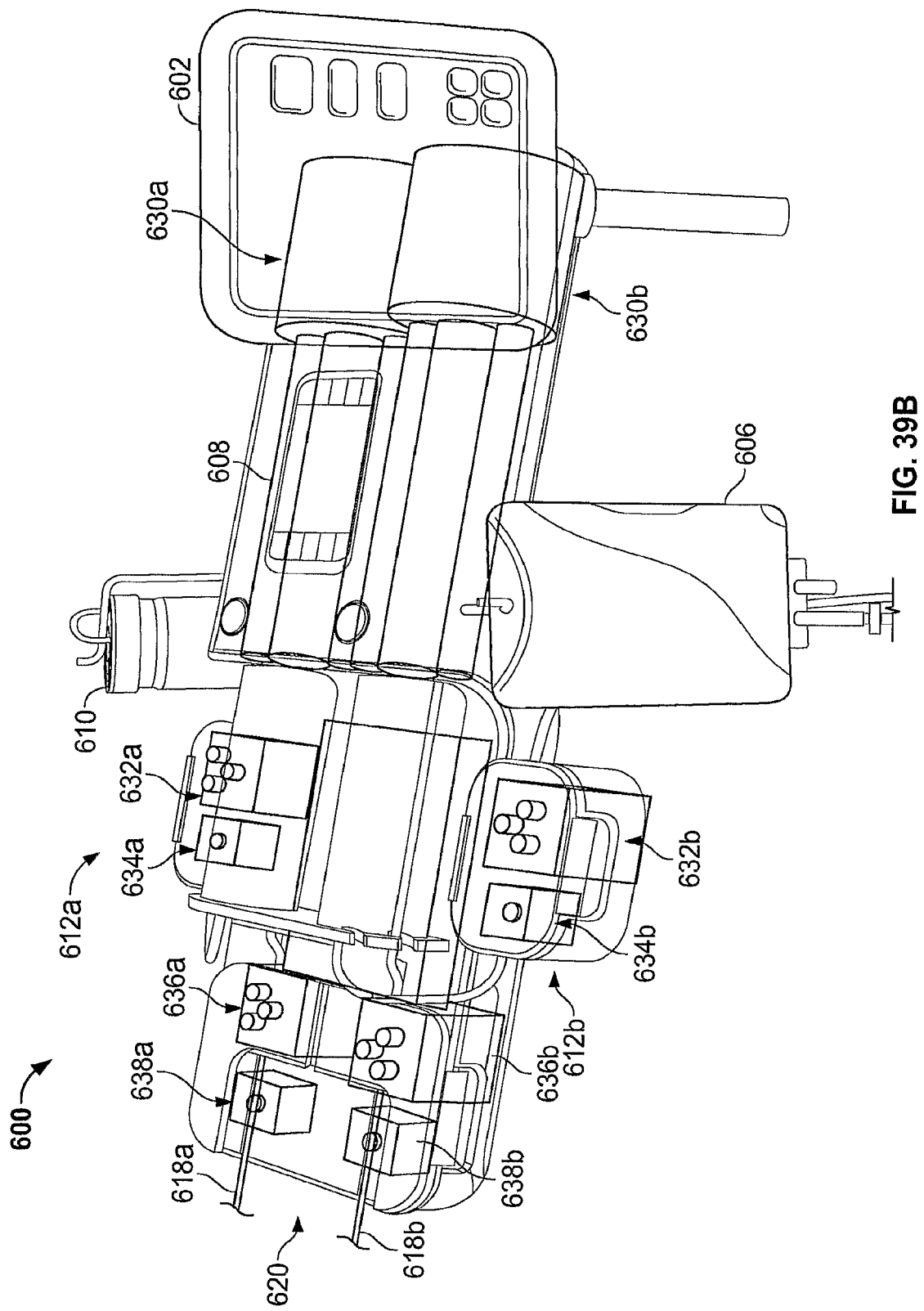
Figure 39C:
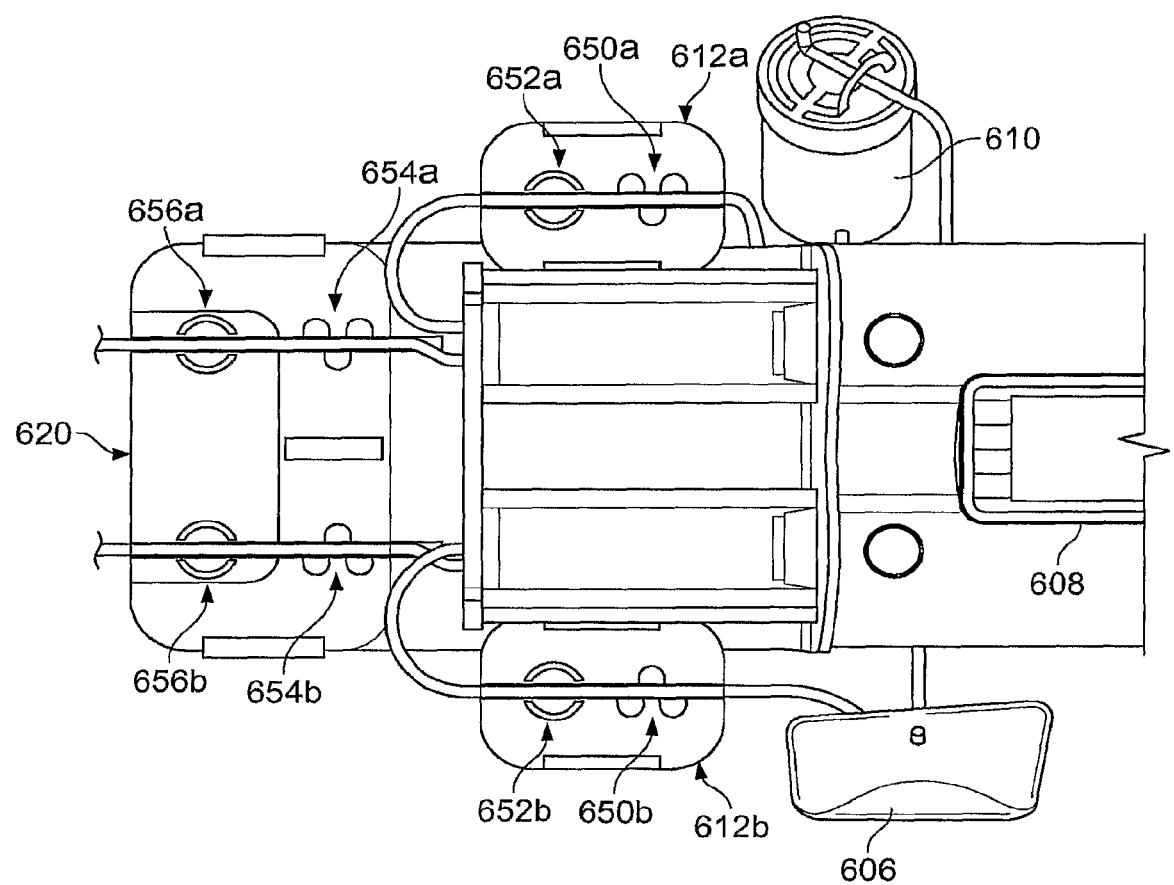

FIGS. 39A-C are views of a dual-syringe contrast injection system, according to one embodiment. FIG. 39A is a perspective view of the system 600. FIG. 39B is a view of the system 600 that shows various internal components. FIG. 39C is a top-view of a portion of the system 600. The system 600 shown in these figures is a dual-syringe system that includes a control panel 602, and injection head 604, and a power supply (not shown). A first reservoir of medical fluid 610 is attached to the injection head 604, and a second reservoir of medical fluid 606 is also attached to the injection head 604. In one embodiment, the reservoir 610 comprises a bottle of sterile contrast media, and the reservoir 606 comprises a bag of sterile diluent, such as saline.

The injection head 604 comprises various sub-components. For example, the injection head 604 includes a small display 608, first and second syringe/plunger assemblies 614a and 614b, first and second valve/air detect assemblies 612a and 612b, and assembly 620. The assembly 620 includes third and fourth valve/air detect assemblies. In one embodiment, the valves used in these assemblies comprise pinch valves. These pinch valves may be actuated by a solenoid, pneumatic, or other form of drive mechanism. The injection system 600 is capable of drawing fluid from the reservoir 610 into the first syringe/plunger assembly 614a via tubing 616a, and is further capable of drawing fluid from the reservoir 606 into the second syringe/plunger assembly 614b via tubing 616b. The tubing 616a runs through the first valve/air detect assembly 612a, and the tubing 616b runs through the second valve/air detect assembly 612b. A door 613a is used to cover the portion of the tubing 616a that runs through the assembly 612a, and a door 613b is used to cover the portion of the tubing 616b that runs through the assembly 612b. In one embodiment, the doors 613a and 613b are transparent or translucent, and are each hinged to an outer edge of their respective pinch valve/air detect assemblies (for opening an closing). In one embodiment, the doors 613a and 613b are each hinged to an inner edge of their respective valve/air detect assemblies.

The assembly 614a is capable of expelling medical fluid into output tubing 618a, and the assembly 614b is capable of expelling medical fluid into output tubing 618b. The output tubing 618a runs through a third valve/air detect assembly, and the output tubing 618b runs through a fourth valve/air detect assembly. A door 622a is used to cover the portion of the output tubing 618a that runs through the third assembly, and the door 622b is used to cover the portion of the output tubing 618b that runs through the fourth assembly. In one embodiment, the doors 622a and 622b are transparent or translucent, and are each hinged to an outer edge of the assembly 620 for opening and closing. In one embodiment, the doors 622a and 622b are each coupled to a common hinge assembly on the top portion of the assembly 620 for opening and closing.

In one embodiment, the air detectors comprise air-column detectors. The air detectors are also capable of detecting air bubbles, according to one embodiment.

The system 600 further includes both a main control panel 602 and also a small control panel 608. An operator of the system 600 may use the main control panel 602 to set up one or more parameters of an injection procedure prior to initiation of the procedure. The operator may also use the main control panel 602 to modify one or more aspects, parameters, etc. of an injection procedure during the procedure, or may also use the panel 602 to pause, resume, or end an injection procedure and begin a new procedure. The control panel 602 also displays various injection-related information to the operator, such as flow rate, volume, pressure, rise time, procedure type, fluid information, and patient information. In one embodiment, the main control panel 602 may be connected to a patient table, while being electrically coupled to the injector head 604. In this embodiment, the operator may manually move the main panel 602 to a desirable location, while still having access to all functionality provided by the panel 602.

In one embodiment, the small panel 608 provides a subset of functions provided by the main panel 602. For example, the operator may use the small panel 608 to manage injector setup. The operator may interact with the small panel 608 to manage the setup of the injector. The small panel 608 may display guided setup instructions that aid in this process. The small panel 608 may also display certain error and troubleshooting information to assist the operator. For example, the small panel may warn the operator of low contrast or saline fluid levels in the liquid reservoirs and/or syringes. In one embodiment, the small panel 608 provides unique display functionality and/or additional functions with regards to the main panel 602, as will be described in more detail below.

In one embodiment, there is further provided an additional remote display (not shown) that may be the size of a personal digital assistant (PDA). This additional remote display may be in communication with the main control panel 602 via a wireless connection, according to one embodiment. A physician may utilize this additional remote display with flexibility, because the display is mobile. Due to its size, the additional display is also very portable and convenient to use. The remote display is capable of receiving user input and providing display information as output, and may provide a subset of functionality that is provided by the main panel 602, according to one embodiment. In one embodiment, the additional remote display provides unique display functionality and/or additional functions with regards to the main panel 602.

In one embodiment, the output tubing 618a and 618b includes a reusable portion and a single-use portion. In this embodiment, the single-use portions of the output tubing 618a and 618b are coupled to the patient catheter and are discarded after a patient procedure. The reusable portions are those portions of the tubing that are directly coupled to the outputs of the syringe assemblies 614a and 614b. The reusable portions and single use portions may be coupled by fluid connectors, according to one embodiment. The valves in the assembly 620 (such as pinch valves) help prevent cross-contamination.

In one embodiment, the tubing 616a is coupled to a fluid input port of the syringe assembly 614a, and the tubing 616b is coupled to a fluid input port of the syringe assembly 614b. The output tubing 618a (or at least its reusable portion, in one embodiment) is coupled to a fluid output port of the syringe assembly 614a, and the output tubing 618b (or at least its reusable portion, in one embodiment) is coupled to a fluid output port of the syringe assembly 614b.

In one embodiment, the reservoir 606, the reservoir 610, the tubing 616a and 616b, the syringe assemblies 614a and 614b, along with the reusable portions of the tubing 618a and 618b are disposable components that may be reused across multiple patient procedures. The single-use portion of the tubing 618 and 618b are disposable components that are to be used for a single patient procedure only and discarded after such use.

FIG. 39B shows an internal view of certain components of system 600. FIG. 39B shows two motor/actuator assemblies 630a and 630b. Each motor in an assembly drives one of the linear actuators. Each linear actuator drives a plunger of one syringe. For example, the linear actuator in the motor/actuator assembly 630a can drive a plunger in the syringe assembly 614a, and the linear actuator in the motor/actuator assembly 630b can drive a plunger in the syringe assembly 614b. An individual plunger is capable of moving within the syringe barrel in either a forward or rearward direction. When moving in a forward direction, the plunger injects liquid into the patient line. For example, when a plunger within the syringe assembly 614a moves in a forward direction (to the left in FIG. 39B), the plunger is capable of injects liquid into the output tubing 618a. When moving in a rearward direction (to the right in FIG. 39B, the plunger is capable of filling liquid into the syringe assembly 614a from the reservoir 610.

As shown in FIG. 39B, the assembly 612a comprises a valve 632a and an air detector 634a. Likewise, the assembly 612b comprises a valve 632b and an air detector 634b. In one embodiment, the valves 632a and 632b comprise pinch valves. Each valve 632a and 632b may be opened or closed by the system 600 to control the fluid connections leading to syringe assemblies 614a and 614b, respectively. For example, the system 600 may open the valve 632a to fill fluid from the reservoir 610 into the syringe assembly 614a. The system 600 may also open the valve 632b to fill fluid from the reservoir 606 into the syringe assembly 614b. The system 600, in one embodiment, is capable of filling syringe assemblies 614a and 614b at the same, or substantially the same, time. The system 600 may close the valves 632a and/or 632b during injection of fluid. For example, the system 600 may close the valve 632a when the syringe assembly 614a is being used to inject fluid from the assembly 614a into the output tubing 618a.

The air detectors 634a and 634b detect the presence of air columns or air bubbles in the associated tubing 616a and 616b. These detectors may include optical, acoustic, or other form of sensors. When one or more of these sensors generates a signal indicating that air may be present in a fluid line leading to the syringe 614a and/or 614b, the system 600 may warn the user or terminate an injection procedure, according to one embodiment.

In the embodiment of FIG. 39B, the assembly 620 includes output valves 636a and 636b, as well as output air detectors 638a and 638b. In one embodiment, the valves 636a and 636b comprise pinch valves. The system 600 controls the output valves 636a and 636b to control when fluid may be injected into a patient via the output tubing 618a and/or 618b. For example, the system 600 may open the valve 636a to allow the assembly 614a to inject fluid into the output tubing 618a. The system may also open the valve 636b to allow the assembly 614b to inject fluid into the output tubing 618b. In one embodiment, the system 600 can inject fluid from syringe assemblies 614a and 614b into output tubing 618a and 618b at the same, or substantially the same, time. In this embodiment, both of the valves 636a and 636b would be open. The system 600 may close the valves 636a and 636b when the system 600 is filling fluid from the reservoirs 610 and/or 606 into the corresponding syringe assembly. For example, the system 600 may close the valve 636a when it fills fluid from the reservoir 610 into the syringe assembly 614a. In this case, the valve 632a would be open.

The air detectors 638a and 638b function similarly to the detectors 634a and 634b, though they are located further downstream in the associated output tubing 618a and 618b, respectively. These detectors 638a and 638b provide signals to the system 600 when they detect air bubbles or air columns in the associated tubing. When the system 600 receives and processes any such signals from the detectors 638a or 638b, the system 600 can alert the user, or may also automatically abort, or stop, an injection procedure to prevent the injection of air into a patient.

In one embodiment, the system 600 opens one or more of the valves 632a, 632b, 636a, or 636b when a user manually loads certain components into the system 600. For example, the system 600 may open an input valve, such as the valve 632a, when the user manually loads a syringe assembly and tubing, such as the assembly 614a and the tubing 616a. In another example, the system 600 may open an output valve, such as the valve 636b, when the user manually loads output tubing, such as the tubing 618b.

FIG. 39C shows a top view of a portion of the system 600. FIG. 39C shows an example of contextual lighting that may be used, according to one embodiment. In this embodiment, contextual lighting is associated with each valve and air detector. Lighted displays 650a and 650b are associated with the valves 632a and 632b, respectively, and are located in proximity to these components. In one embodiment, the lighted displays are adjacent to the associated components. Lighted displays 652a and 652b are associated with the air detectors 634a and 634b, and are located in proximity to these components. Lighted displays 654a and 654b are associated with the valves 636a and 636b, and are located in proximity to these components. Lighted displays 656a and 656b are associated with the air detectors 638a and 638b, and are located in proximity to these components. The individual lighted displays help indicate to an operator where specific components (such as the valves and air detectors) are located in the system 600. In one embodiment, the lighted displays 650a, 650b, 652a, 652b, 654a, 654b, 656a, and 656b comprise lighting patterns, such as lighted graphics.

In one embodiment, the system 600 provides a guided setup mode to a user who may be less familiar, or experienced, with the system 600. In this embodiment, the contextual lighting helps guide a user as to how to setup the system 600 for use. For example, the system 600 may cause one or more of the lighted displays to blink, change color, or provide another visual indication that setup is to proceed in a certain fashion, or that certain conditions exist. In one scenario, the system 600 may cause the display 650a to blink, indicating that the user is to load the tubing 616a through the valve 632a. Once the user has successfully loaded the tubing or otherwise properly performed a setup function, the system 600 may then causes the lighted display 650 to display a solid (non-blinking) light to indicate that loaded is complete, or successful. Similarly, a change in color of a display (e.g. red to green) may indicate that a step has been completed successfully. The remaining displays 650*b*, 652*a*, 652*b*, 654*a*, 654*b*, 656*a*, and 656*b* may be controlled in a similar fashion during a guided setup. In one embodiment, the system 600 will not solidly light the lighted display (indicating successful loading) until the user has closed the appropriate loading door 613*a*, 613*b*, 622*a*, and/or 622*b* or until the user has otherwise properly performed setup.

In one embodiment, the system 600 further provides an express setup mode for a user who is quite experienced in using the system 600. In this embodiment, the user may load the system components at the user's discretion, and the system 600 will light the displays after the user has successfully completed loading individual components or otherwise properly performed one or more setup functions. For example, after the user has loaded the output tubing 618*b* through both the valve 636*b* and the air detector 638*b*, the system 600 can cause the lighted displays 654*b* and 656*b* to visual display solid lights, indicating that the user has successfully completed loaded the output tubing 618 through these components. The system 600 may also cause one or more lighting patterns to display light of a specified color, such as green, to indicate successful loading.

In one embodiment, the system 600 may also cause the lighted displays to display identified colors to indicate potential or actual error conditions, or to indicate that the user has improperly performed a setup function. For example, the system 600 may cause the display 650*b* to show a solid, red color to indicate to the user that the valve 632*b* has malfunctioned. Or, the system 600 may cause the display 656*a* to show a solid, red color to indicate to the user that the air detector 638*a* has detected a presence of air. Various other visual or graphical patterns, displays, and the like may be provided for the lighted displays 650*a*, 650*b*, 652*a*, 652*b*, 654*a*, 654*b*, 656*a*, and 656*b* in the system 600.

FIGS. 40A-B and 41A-B are perspective views of certain embodiments of disposable fluid connections that may be used in a powered injection system, such as the system 600. Although the examples shown in these figures highlight disposable connections that may be used in a dual-syringe injection system, other embodiments provide use of these connections in injection systems having other configurations, for example as a syringe and a peristaltic pump, such as the system shown in FIG. 42. In various embodiments, the disposable fluid connections may be coupled to one or more pressurizing units, such as a syringe, a peristaltic pump, or other form of pump. Various embodiments of a disposable fluid connector help minimize the number of connections that are required to a powered injection system and/or to a patient line.

Figure 40A:
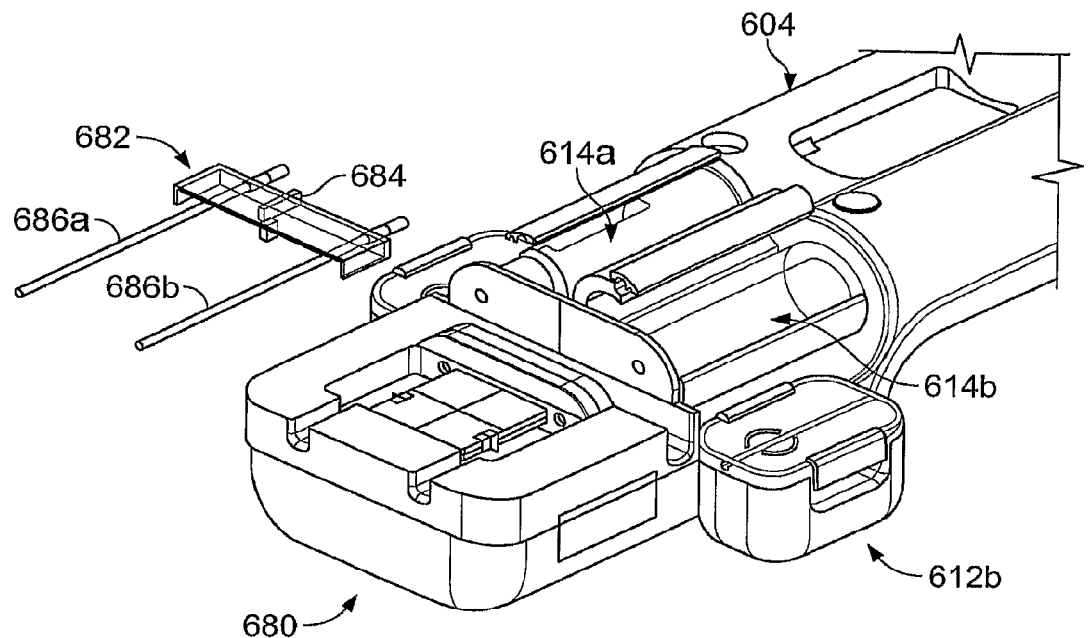
FIGS. 40A-B and 41A-B are perspective views of certain embodiments of disposable fluid connections that may be used in a powered injection system.
Figure 40B:
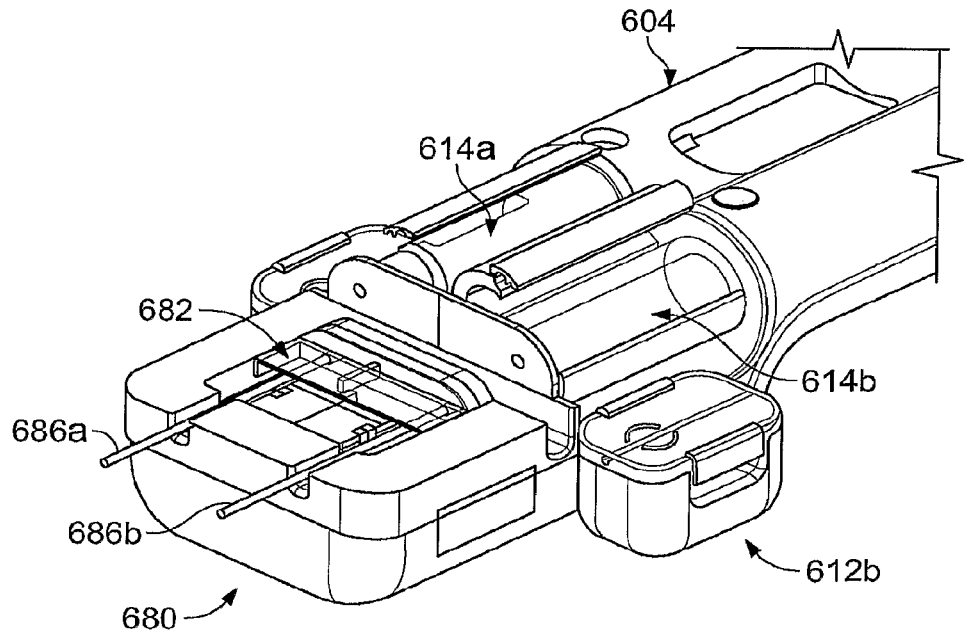

FIG. 40A shows one embodiment in which a disposable fluid connector 682 may be used with the injection system 600. In this embodiment, the disposable fluid connector 682 may be loaded into an assembly portion 680 of the injection head 604. As such, the connector 682 is coupled as one single assembly to the injector. FIG. 40B shows an example of the connector 682 after it has been loaded into the portion 680. The connector 682 is used only for a single patient procedure (single use), according to one embodiment. In this embodiment, the connector 682 is discarded after it has been used for an injection procedure on a particular patient. In one embodiment, the connector 682 is referred to as a "disposable cassette" that may be loaded and unloaded as one assembly into the portion 680 of the injector head 604. The portion, or member, of the connector 682 that seats onto a top portion of the portion 680 is made of a resilient material, such as plastic, according to one embodiment. This member is non-removably attached to both the tubing 686*a* and 686*b*, according to one embodiment. When manipulating the connector 682, or loading/unloading the connector 682 into the portion 680, a user may grasp and/or manipulate the member that is non-removably attached to both the tubing 686*a* and 686*b*. This allows the user to more easily and conveniently handle the connector 682, according to one embodiment. In one embodiment, the member may be removably connected to both the tubing 686*a* and 686*b*.

The connector 682 shown in FIG. 40A-B includes output tubing 686*a* and 686*b*. The connector 682 further includes a connection 684. The connection 684 may be used to connect the connector 682 to an external medical device or to an external signal source. The connection 684 is coupled to the injection head 604. For example, in one embodiment, the connection 684 may be connected to a pressure transducer, such that the system 600 may monitor hemodynamic signals. In this embodiment, a cable is used to connect the pressure transducer to the connection 684. The connection 684 includes an RJ-11 connector, and signals from the pressure transducer can then be routed to the system 600 via connection 684 for processing. In one embodiment, a cable may be used to directly connect an external medical device, such as a hemodynamic monitoring device or a balloon inflation device, to the system 600 via the connector 684. In one embodiment, the system 600 is capable of detecting the presence of the connector 682 to the head 604 by means of the connection 684. In this embodiment, the system 600 detects the presence of the connection 684 by way of an electrical connection to the portion 680 of the head 604.

As shown in FIG. 40A-B, the output tubing 686*a* and 686*b* rest in separate grooves, or channels, of the portion 680 when the connector 682 is loaded. The output tubing 686*a* and 686*b* comprise the single-use portions of the output tubing 618*a* and 618*b*, respectively. The tubing 686*a* and 686*b* are used only for a single use (patient), and are discarded after an individual patient procedure, according to one embodiment. The tubing 686*a* and 686*b* have proximal ends that are coupled to the respective portions of output tubing 618*a* and 618*b* that are reusable across multiple patient procedures and that are directly coupled to the output ports of the syringe assemblies 614*a* and 614*b*, respectively. The tubing 686*a* and 686*b* have distal ends that can each be coupled to a patient line connected to the patient. The use of the valves 636*a* and 636*b* (such as pinch valves) aid in the prevention of cross-contamination of the reusable portions of the output tubing 618*a* and 618*b*. In one embodiment, the tubing 686*a* and 686*b* are coupled to a fluid valve, such as the elastomeric valve shown and described in reference to FIGS. 55A and 55B (below). In this embodiment, the tubing 686*a* is coupled to a first input port of the valve, and the tubing 686*b* is coupled to a second input port of the valve. The output port of the valve is then coupled to the patient line. The valve controls the flow of fluid through the tubing 686*a* or 686*b* to the patient line.

Figure 41A:
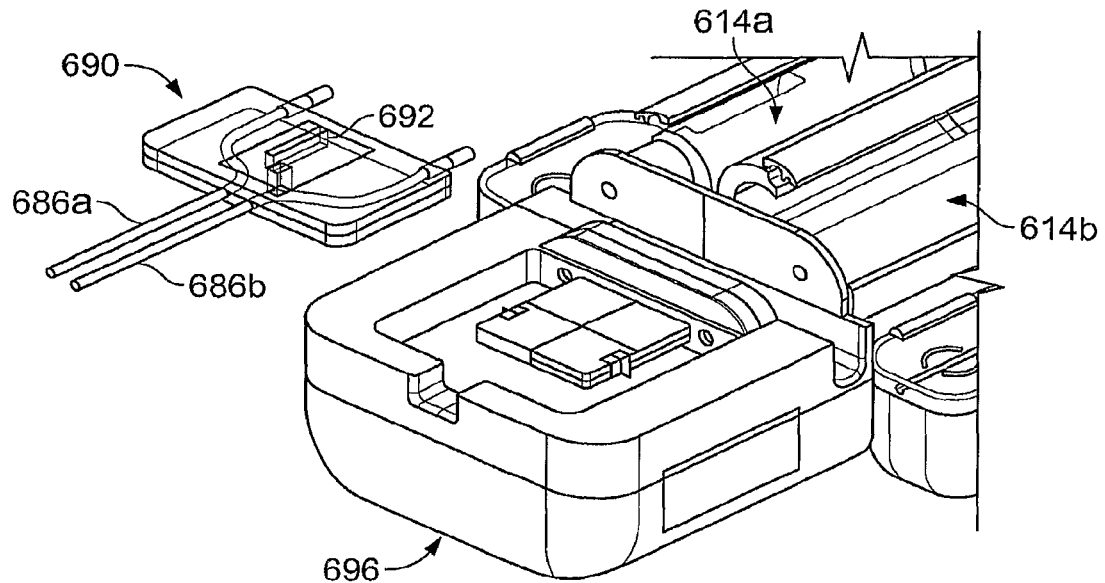
Figure 41B:
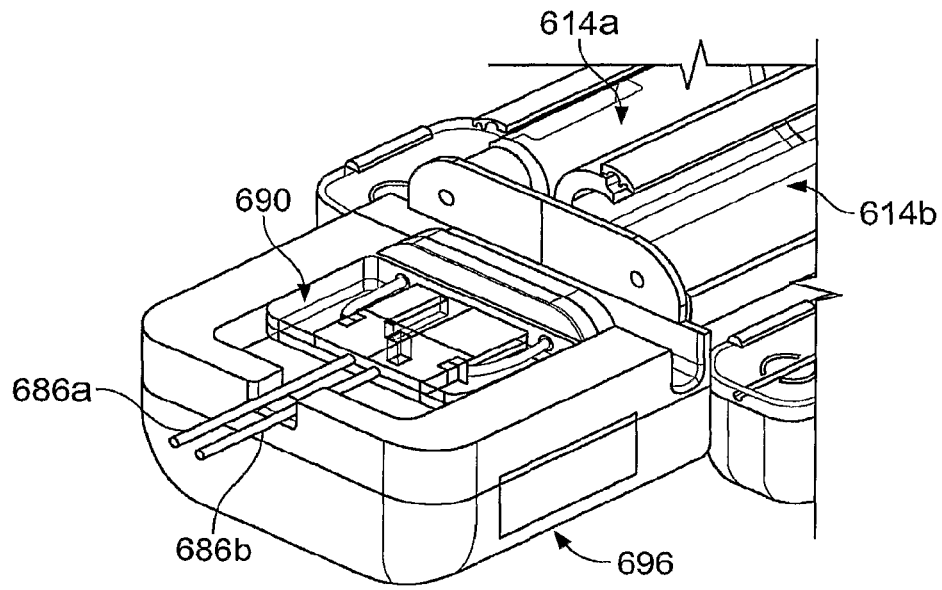

FIGS. 41A-B are perspective views of disposable fluid connections that may be used in a powered injection system, such as the system 600, according to another embodiment. FIG. 41A shows an example of a disposable connector 690 that may be used in the system 600, and FIG. 41B shows an example of the connector 690 after it has been loaded into an assembly portion 696 of the injector head 604. The connector 690 includes a connection 692 that is similar to the connection 684 shown and described previously. The connector 690 comprises a component for loading into the portion 696 having a larger size than the connector 682 shown in the previous figures. In one embodiment, this larger-size component slides into and over a receptacle area of the portion 696, and the output tubing 686a and 686b are located in close proximity as they pass through a narrow groove, or channel, of the portion 696.

Figure 42:
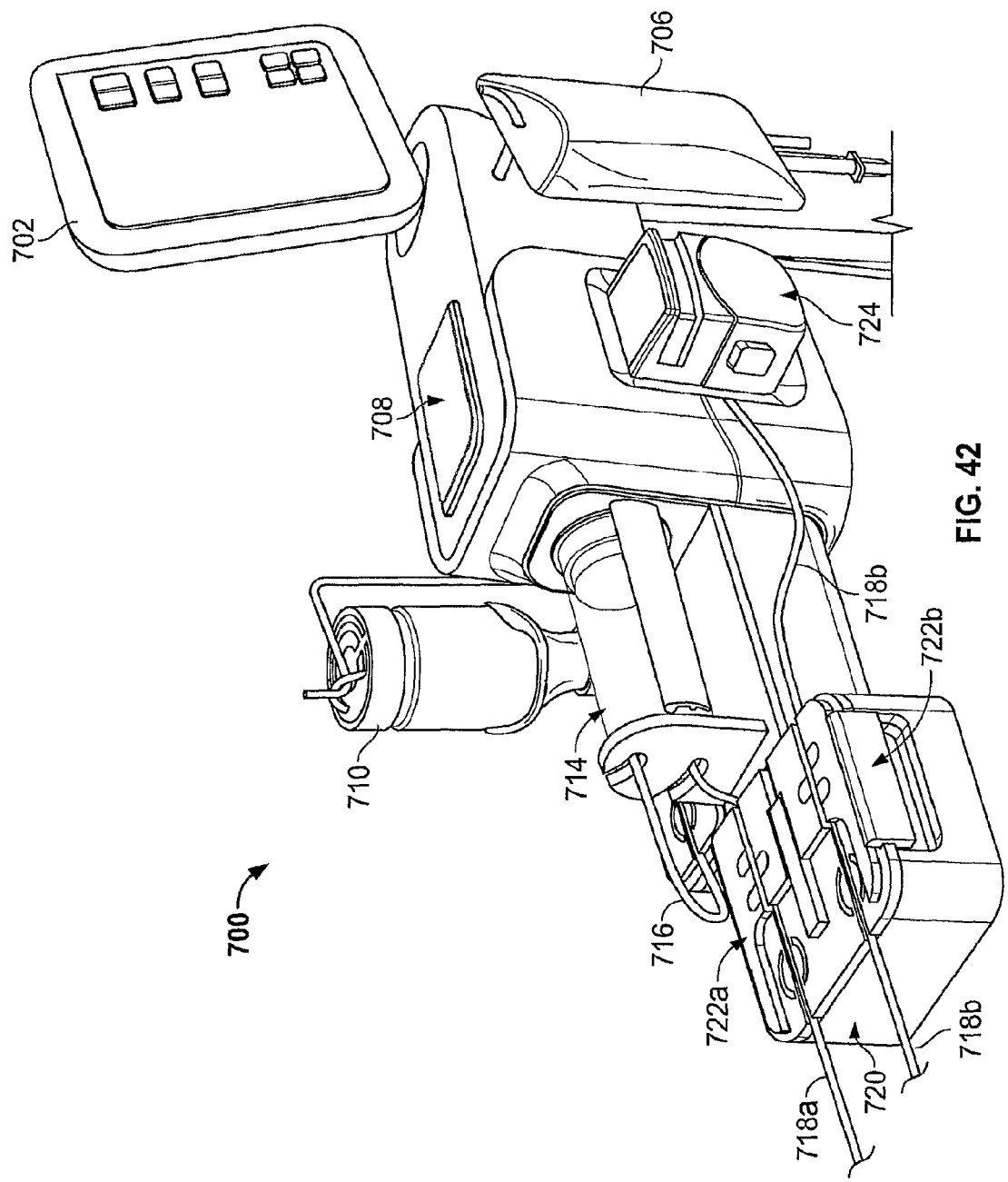
FIG. 42 is a perspective view of a powered injection system that includes a syringe and a peristaltic pump, according to one embodiment.

FIG. 42 is a perspective view of a powered injection system 700 that includes a syringe 714 and a pump, such as a peristaltic pump 724, according to one embodiment. In this embodiment, the syringe 714 is used to deliver a first medical fluid, such as contrast media, to a patient, and the pump 724 is used to deliver a second fluid, such as a saline diluent, to the patient. The system 700 also includes a main control panel 702, a small control panel 708, a first fluid reservoir 710, a second fluid reservoir 706, input tubing 716, output tubing 718a and 718b, an assembly 720, and doors 722a and 722b.

In one embodiment, the control panel 702 is similar in shape and function to the panel 602 shown in FIG. 39A, and the small panel 708 is similar in shape and function to the panel 608. The reservoir 710 contains a first medical fluid, such as contrast media, and the reservoir 706 contains a second fluid, such as saline. As is shown in the example of FIG. 42, the reservoir 710 is a glass bottle and the reservoir 706 is a plastic bag. In other embodiments, other reservoir types may be used. The fluid within the reservoir 710 is filled into the syringe 714 through tubing 716 upon retraction of a plunger within the syringe 714. The system 700 is capable of controlling movement of the plunger. In one embodiment, the system 700 controls movement of the plunger upon receipt of user input, such as user input from a hand-control device or user input provided on the panel 702 and/or 708. The fluid within the reservoir 706 is moved through the tubing 718b by operation of the peristaltic pump 724. The pump 724 is also controlled by the system 700.

Medical fluid contained within the syringe 714 may be injected into the patient via output tubing 718a, and medical fluid from the reservoir 706 may be injected into the patient via output tubing 718b through operation of the pump 724. The output tubing 718a and 718b are operatively connected to a patient catheter in one embodiment.

In one embodiment, the tubing 18a comprises a single-use portion and a multi-use portion. The single-use portion is operatively coupled to the patient line (catheter), and the multi-use portion is coupled to the output of the syringe 714. The single-use portion and the multi-use portion are coupled via a connector.

In one embodiment, the reservoir 706, the reservoir 710, the tubing 716, the syringe 714, and the reusable portion of tubing 718a are disposable components that may be re-used across multiple patient procedures, whereas the single-use portion of tubing 718a and the tubing 718b are disposable components that are used only for a single patient procedure. The assembly 720 includes two valve and air-detector assemblies (one each associated with the syringe 714 and the pump 724). The doors 722a and 722b are hinged to the assembly 720 and function similarly to the doors 622a and 622b. In one embodiment, the system 700 further includes a valve and an air detector (not shown) between the reservoir 710 and the syringe assembly 714, similar to valve 632a and air detector 634a shown in FIG. 39B. The tubing 716 runs through this valve and through the air detector. In one embodiment, the valves comprise pinch valves.

In one embodiment, there is further provided an additional remote display (not shown) that may be the size of a personal digital assistant (PDA). This additional remote display may be in communication with the main control panel 702 via a wireless connection, according to one embodiment. A physician may utilize this additional remote display with flexibility, because the display is mobile. Due to its size, the additional display is also very portable and convenient to use. The remote display is capable of receiving user input and providing display information as output, and may provide a subset of functionality that is provided by the main panel 702, according to one embodiment. In one embodiment, the additional remote display provides unique display functionality and/or additional functions with regards to the main panel 702.

FIG. 43-FIG. 54 illustrate various embodiments of screen displays that may be provided within a graphical user interface (GUI) in a powered injection system, such as, for example, the system 600 shown in FIG. 39A or the system 700 shown in FIG. 42. These screen displays may be provided on a control panel of the system, such as the control panels 602, 608, 702, and/or 708 shown and described previously. In one embodiment, these screen displays may also be provided on an additional, small, remote and portable display that is coupled to the main panel. Examples of such small, remote displays have been described previously.

Figure 43:
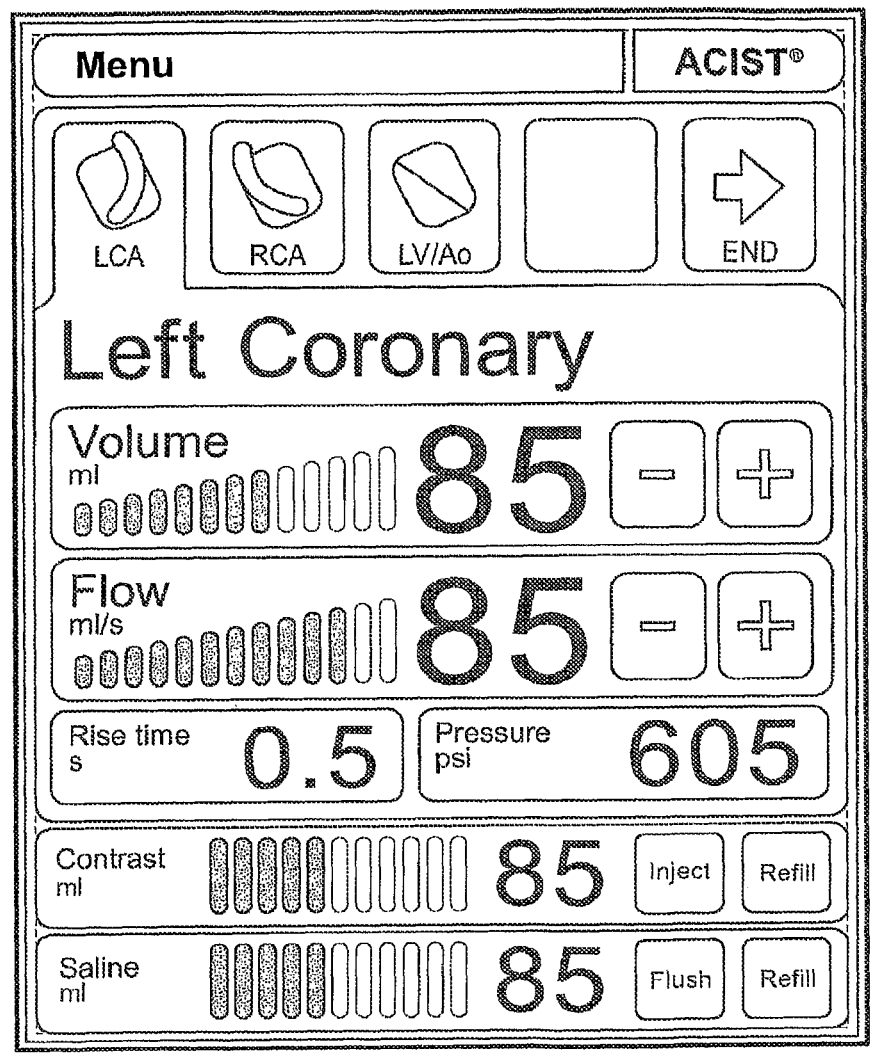
FIG. 43-FIG. 54 illustrate various embodiments of screen displays that may be provided within a graphical user interface (GUI) in a powered injection system.

In one embodiment, the screen display shown in FIG. 43 is provided on a main console, or control panel, of the system, such as the control panel 602 or 702. As shown in FIG. 43, the user of the system can interact with the screen display that is provided, since the control panel includes a touch-screen interface. In one embodiment, the control panel also includes hard buttons that may be depressed by the user to provide input to the system. In other embodiments, other forms of user interfaces (such as voice activated, hand controlled, foot controlled) may be used.

The user may select the type of procedure to be performed by selecting one of the displayed options. In FIG. 43, the displayed options are "LCA" (left coronary artery), "RCA" (right coronary artery), and "LV/Ao" (left ventricle/aorta). Each option is associated with a corresponding graphical symbol, such as an icon. Each symbol is associated with information about a medical procedure that may be performed on a patient. In one embodiment, the symbols each represent an anatomical location of a patient (e.g., LCA, RCA, LV/Ao) that is associated with the medical procedure to be performed, as shown in the example of FIG. 43. In this example, the user has selected "LCA". In one embodiment, the symbols each represent a type of medical device or equipment that is to be used in performing the medical procedure.

Once the user has made a selection, default injection parameters for that selection, which are associated with the corresponding medical procedure, are retrieved and displayed to the user. In the example of FIG. 43, default parameters for the selection "LCA" are displayed, which are associated with an injection procedure into the left coronary artery. These default parameters are stored within the system and are configured by the manufacturer, in one embodiment. In one embodiment, the user has the ability to customize the default parameters that are stored. These parameters apply to an individual patient injection procedure. After the parameters are displayed to a user, the user may then modify one or more of the parameters using the GUI, according to one embodiment.

The use of the graphical symbols, or icons, helps provide the user with quick and recognizable graphics associated with the appropriate procedure to be performed. This can help improve workflow and speed of setup, as well as possibly help prevent mistakes. In one embodiment, the graphical icons can also be displayed in different colors to indicate the status, or state, or the device. In one embodiment, different colors may be used for the following states: unselected, selected, armed (injector), and touched (by the user). For example, after a user has selected one of the options, the system may prominently display the selected option within the GUI by changing the color of the selected option (and corresponding graphical symbol).

In FIG. 43, the user may modify the maximum injection volume, the maximum flow rate, the rise time, and maximum injection pressure. The screen display also includes bar indicators, along with associated numeric values, to indicate the amount of contrast or saline remaining in the associated contrast reservoirs (such as reservoirs 706 or 710). The user may press the "inject" button to cause an injection of fluid to commence, or may press the "refill" button to cause a refill operation to commence. The user may press "inject" for one fluid medium (such as contrast) and press "refill" for the second fluid medium (such as saline) at the same, or substantially the same, time (according to one embodiment). In one embodiment, the system has knowledge of reservoir size/volume based upon previously entered input into the system.

Figure 44:
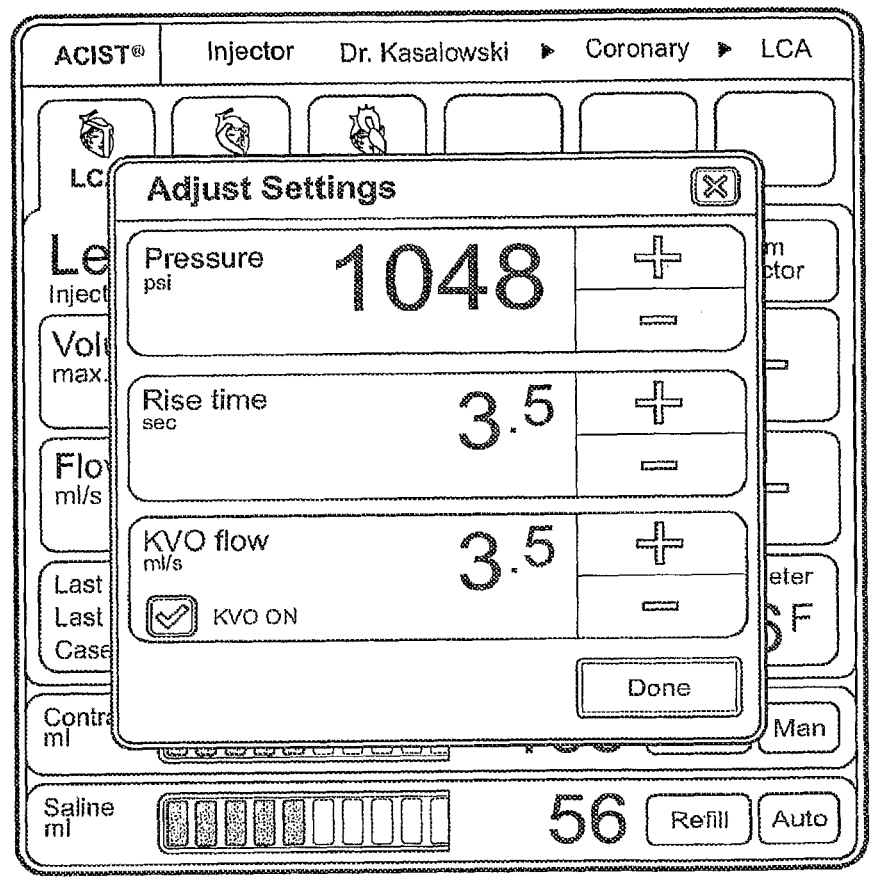

FIG. 44 shows an example of active and inactive screen portions on the display, according to one embodiment. In this embodiment, the screen window entitled "Adjust settings" is the active window, and all other background menus or windows are inactive (grayed out). In this fashion, the user's focus may be directed solely to the active portion of the display, while the rest of display is entirely disabled. In this example, the user's attention is directed solely to the adjustment of settings, based upon the user's prior selection for modification. The active window may be used by the user to adjust maximum pressure, rise time, and KVO (keep vein open) flow (if the KVO feature is turned on).

Figure 45:
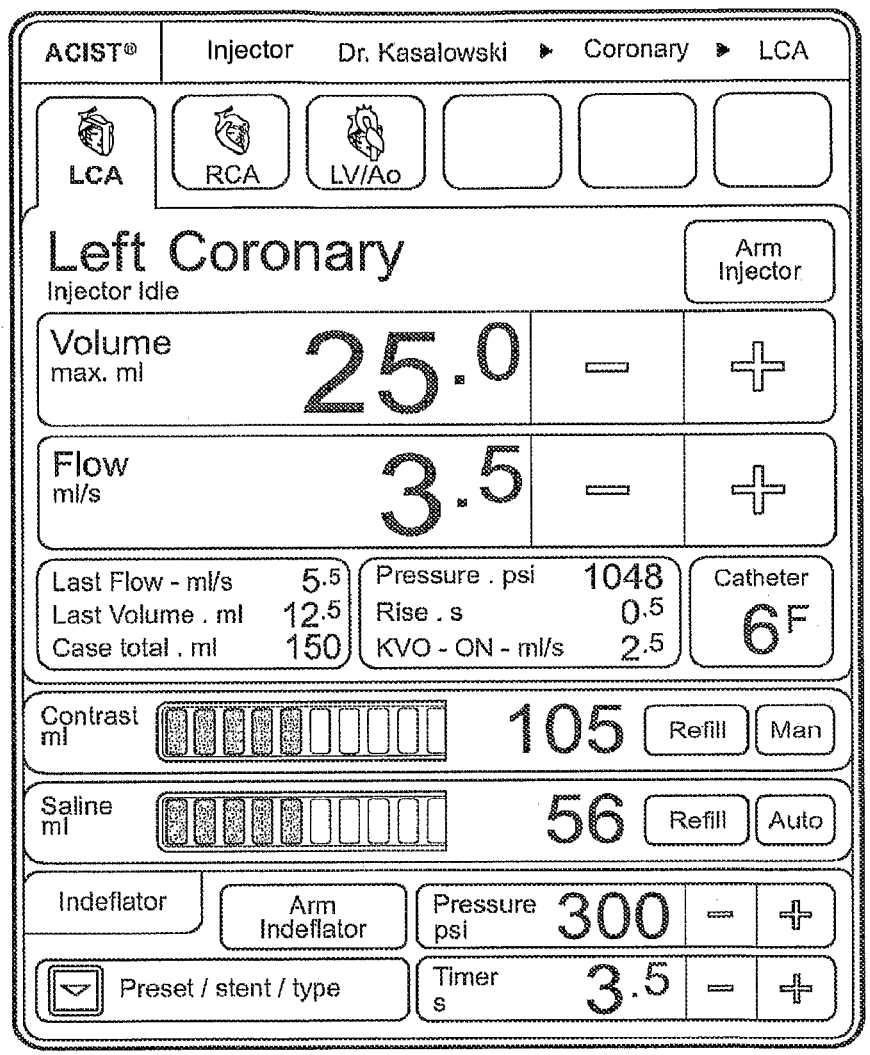

FIG. 45 shows a screen display similar to the one shown in FIG. 43. The display of FIG. 45, however, includes a few additional features. As shown, the screen display provides additional details, such as the flow rate of the prior injection, the injection volume of the prior injection, and the total amount of fluid injected for the given case. The screen display also provides details about the current size of the catheter being use, the calculated pressure of injection, the rise time, and the rate for KVO. In addition, the screen display provides controls and settings at the bottom of the screen for controlling and managing an external medical device, such as a balloon inflation device ("indeflator", for inflation/deflation). In one embodiment, the balloon inflation device may be an automated inflation device. Using the GUI on the screen display, the user may arm/disarm the inflation device, select the type of balloon/stent/etc. that is to be used in the procedure, and adjust various inflation/deflation parameters, such as pressure and time on inflation/deflation. The screen display shown in FIG. 45 provides the user with a myriad of options for controlling multiple medical devices from a single GUI displayed on a control panel.

Figure 46A:
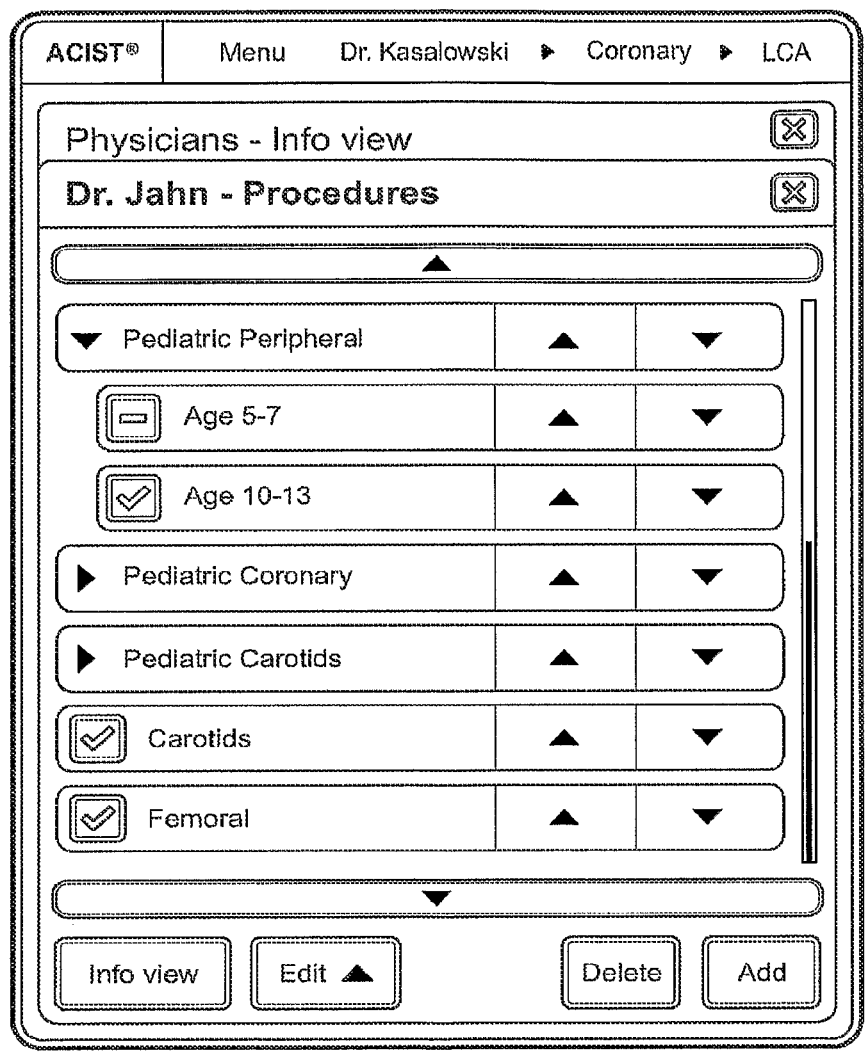
Figure 46B:
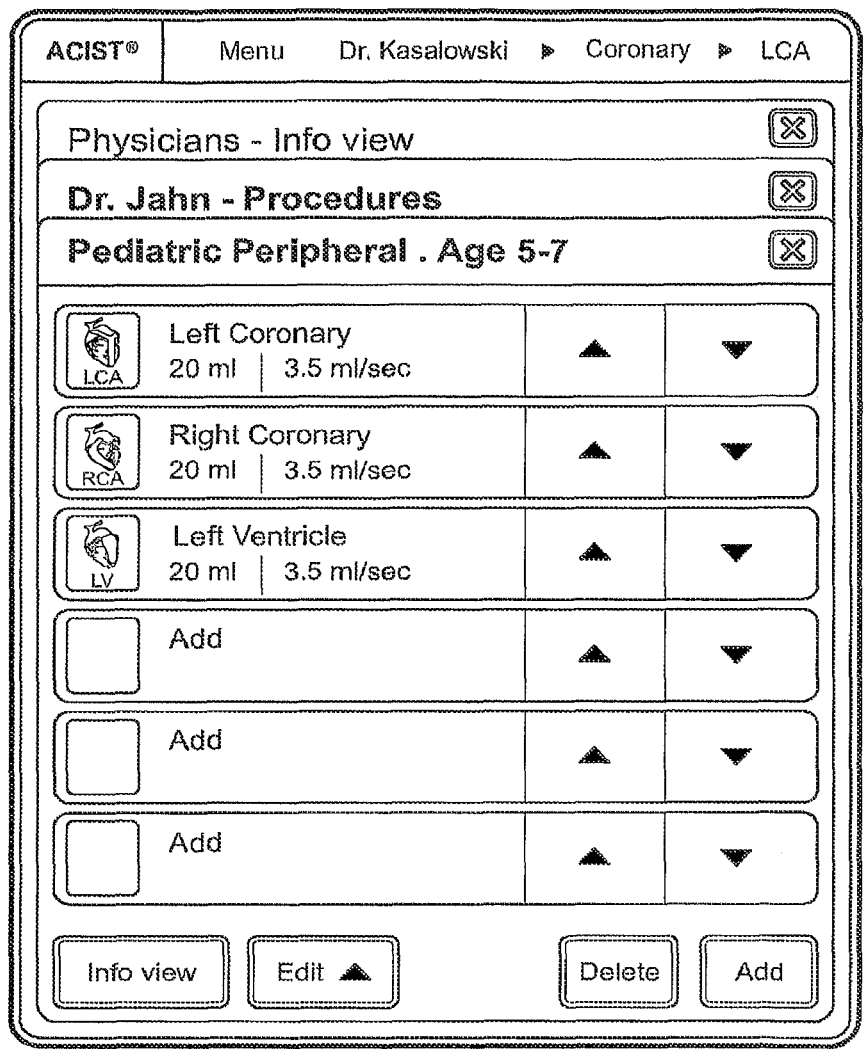

FIGS. 46A and 46B show exemplary screen displays that may be provided to a user for customization of various injection settings, or parameters, for a particular individual, such as a physician. Because an individual injection system may be used over time by multiple different physicians or operators, it may often be useful for physicians to create a profile, or multiple profiles, for their own selected or preferred, settings for given procedure types or scenarios. When an individual user wishes to use the system, that user may then recall his or her profile(s) of preferences as stored in the system quickly and conveniently.

As shown in FIG. 46A, a user has selected procedures for an exemplary physician. Various procedures are displayed, such as "pediatric peripheral", "pediatric coronary", and "pediatric carotids". A default set of procedures may be loaded into the system by the manufacturer, but may further be customized by the user. Within individual procedure types, the system may display additional categories of patients, such as ages or age groups of patients.

In the example of FIG. 46B, the user has selected "Age 5-7" for the general procedure type of "Pediatric Peripheral" for the indicated physician. For this physician, the indicated parameters would be stored as default parameters for the specified procedure type and patient falling within the designated age range. As is shown in FIG. 46B, the screen displays parameters for specific procedures for the selected type. These exemplary procedures are "Left Coronary", "Right Coronary", and "Left Ventricle". Associated graphical representations, or icons, are displayed next to the textual descriptions of the procedures. Also shown are the designated parameters for each procedure, such as maximum injection volume and maximum flow rate. The user may select or change any of the procedure parameters for use with the indicated physician, and these may then be saved into the system for later use.

Figure 47:
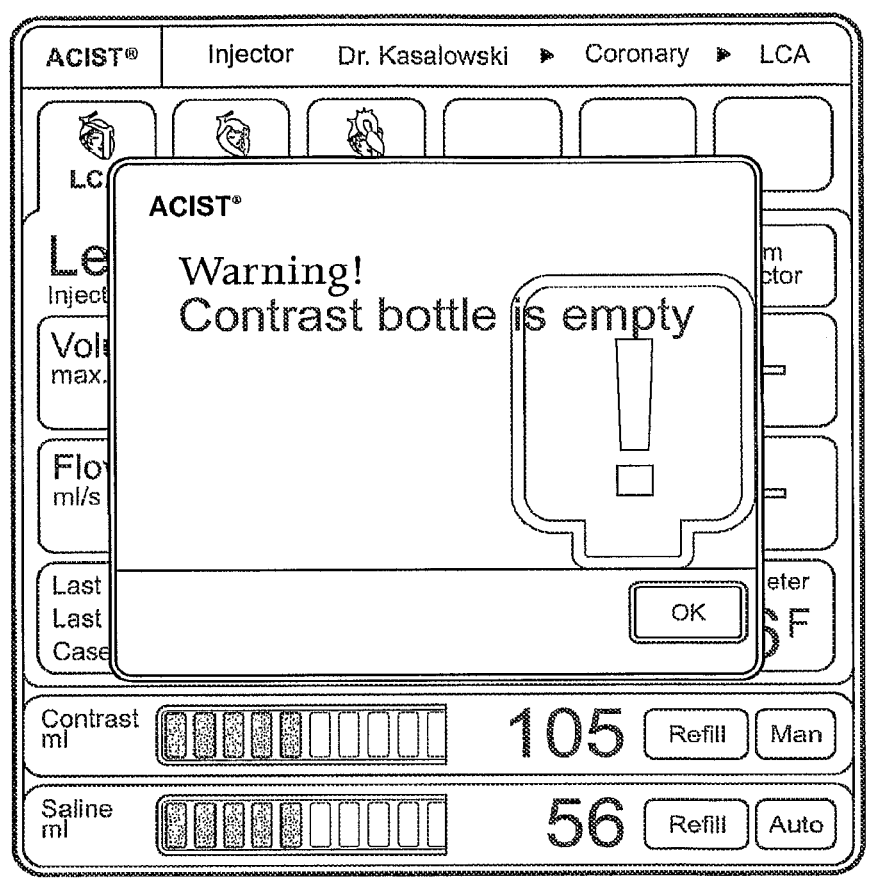

FIG. 47 shows an exemplary screen display with an error indicator. As shown, this particular error indicator graphically indicates to the user of a specific warning. In this scenario, the warning indicates that the contrast bottle is empty. In this embodiment, the user must click on the "OK" button before returning to the screen that had previously been displayed. The warning window provides another example of a highlighted window of focus that is displayed to the user, while all other windows and/or portions of the GUI are dimmed/grayed out and out of focus. In one embodiment, the warning shown in FIG. 47 is displayed in a particular color, such as yellow. In this embodiment, one color is used for certain types of warnings, and other colors are used for other types of warnings, or errors. The use of colors assists the user in quickly and accurately identifying and resolving issues that may occur, or have occurred, in the system.

Figure 48:
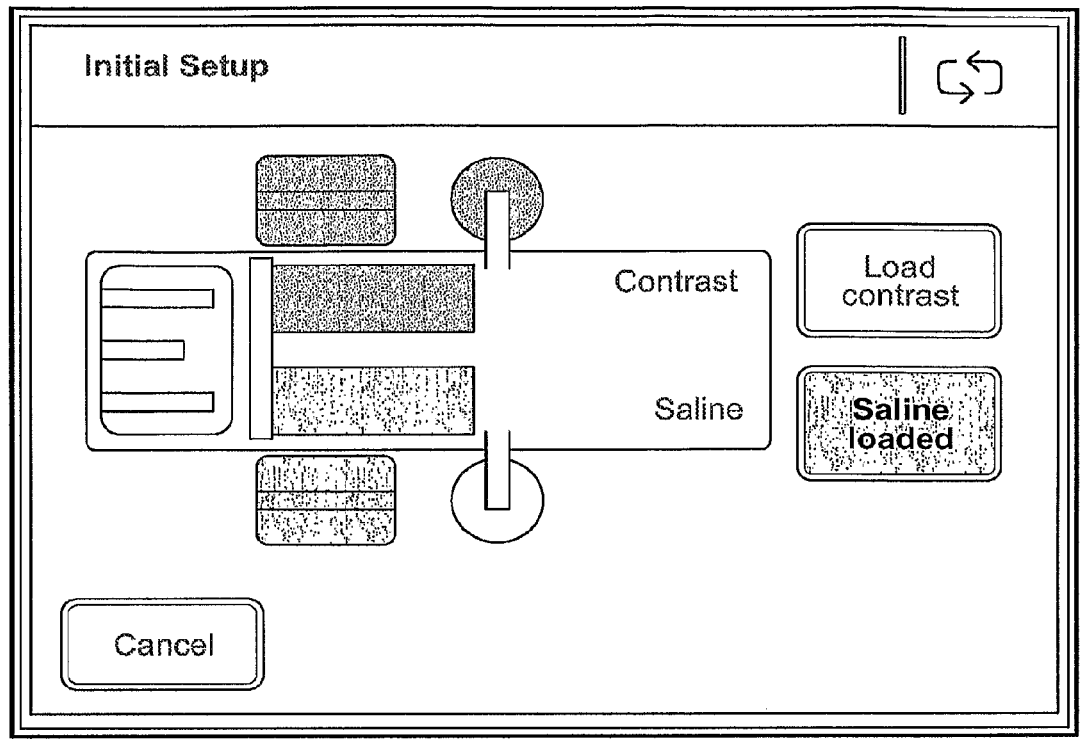
Figure 49:
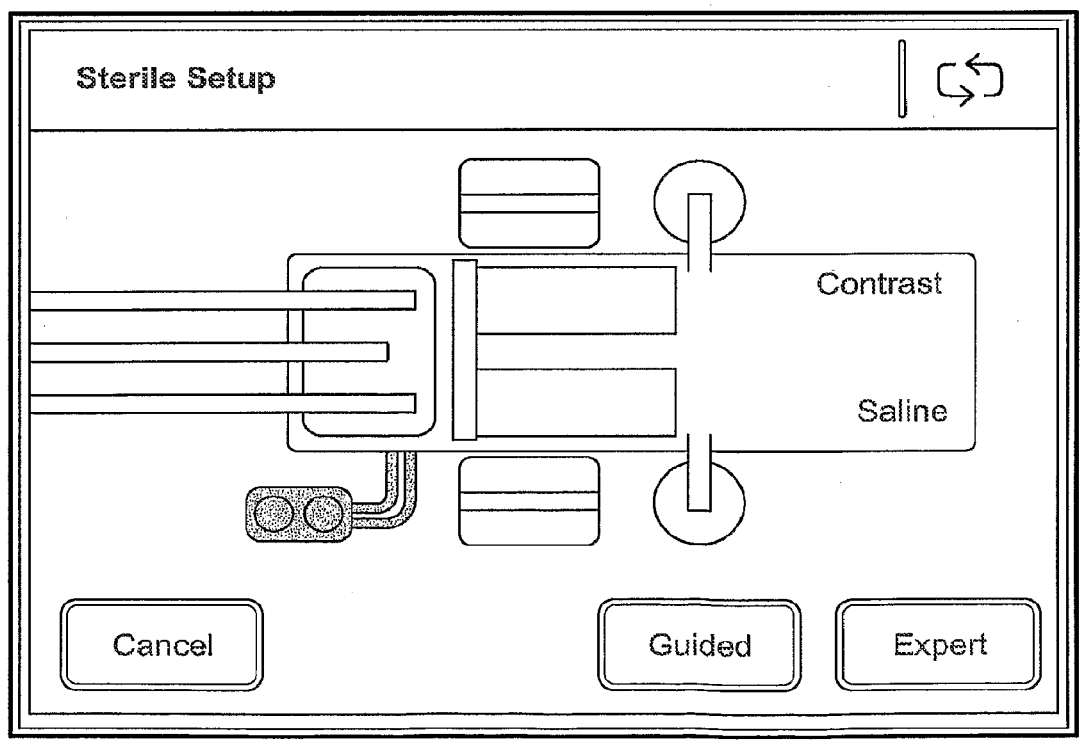
Figure 50:
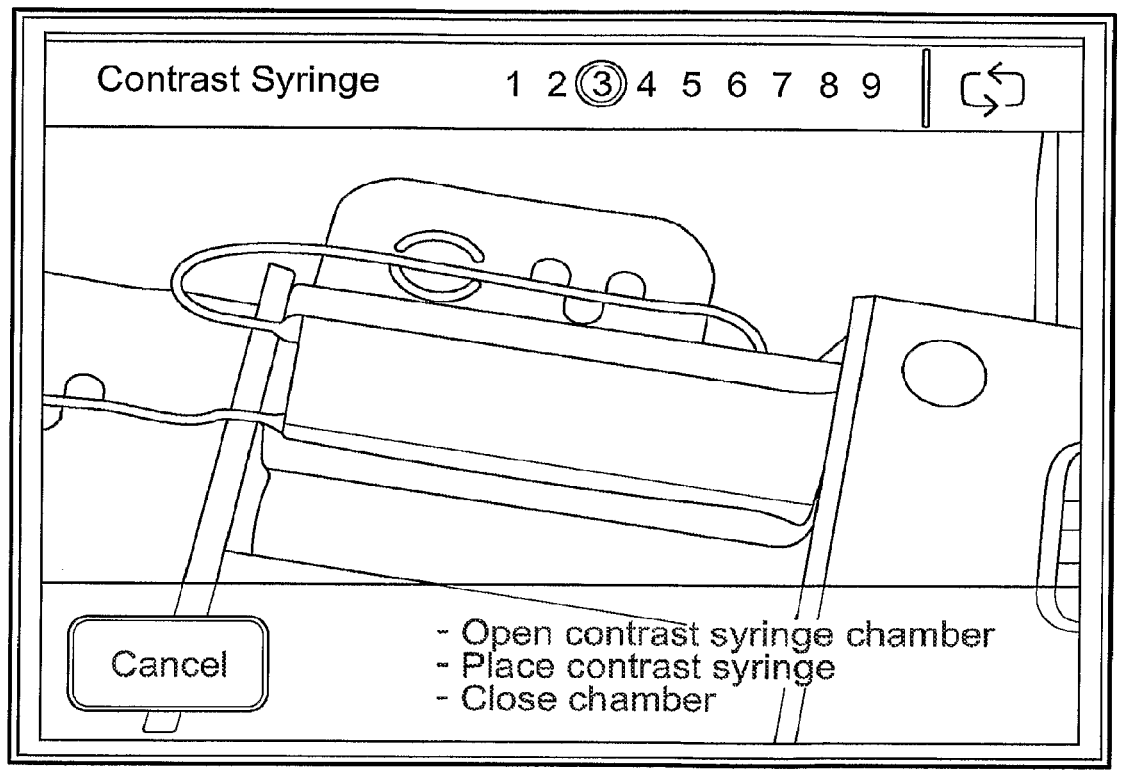

FIG. 48 through FIG. 50 provide examples of screen displays that may be provided by the system for setup of the injection system (such as the system 600 or 700). In one embodiment, the setup screens are capable of being provided on both a main control panel (such as the panel 602) and a small panel on the injection head (such as the panel 608). In this embodiment, the main control panel may be capable of providing certain setup information (or setup screens), while the small control panel may be capable of providing other setup information (or screens), based upon the type or sequence of setup information. In one embodiment, the setup screens are provided only on either the main control panel or the small control panel. In one embodiment, the setup screens may also be provided on a small, remote, portable panel (that may be the size of the PDA), as well.

In one embodiment, the injection system provides both a guided setup and an express, or expert, setup mode. The guided setup mode may be used by a user who is somewhat less familiar, or experienced, with the system, or who may want more specific instructions as to how to use the system. In the guided setup mode, contextual lighting on the injection head may further help guide a user as to how to setup the system for use. For example, while proceeding through instructions on the GUI (graphical user interface on the console) for the guided setup mode, the system may cause one or more of the lighted displays, such as patterns, on the injection head to blink, change color, or provide some other form of visual indication that setup is to proceed in a certain fashion, or that certain conditions (such as error conditions) exist. For example, in one scenario, the GUT may specify that the user is to load the contrast syringe. On the injection head, the contextual lighted display associated with contrast syringe may blink in a particular color, such as yellow, to instruct the user where to take action. The GUI may then provide graphical and textual instructions to the user regarding loading of the contrast syringe. In this fashion, the user receives guided setup instructions from the GUI and corresponding indicators (via contextual lighting) on the injector head to provide setup assistance. Additional instructions may be provided for other setup tasks, such as loading reservoirs, loading tubing, loading cartridges, installing hand controller to the system, and the like. Different colors and color patterns may also be used. For example, the system may provide yellow lights/lighting patterns to indicate that certain setup steps are to be performed, white lights/patterns to indicate that certain setup steps have been successfully performed, or red lights/patterns to indicate that one or more errors have occurred. In addition, the system may provide blinking or solid light patterns for different status conditions. For example, the system may provide blinking lights to indicate that certain setup steps are to be performed, or provide solid lights to indicate that certain setup steps have been completed.

In one embodiment, the system further provides an express, or expert, setup mode for a user who is more experienced in using the system, or who may not wish to go through an interactive setup procedure. In this embodiment, the user may load the system components at the user's discretion, and the system will implement certain lighting patterns to indicate that the user has successfully completed certain setup phases. For example, after the user has loaded tubing through both a valve and an air detector, the system can cause the lighted displays on the injection head to visual display solid lights, indicating that the user has successfully completed loaded the tubing. The system may also cause one or more lighting patterns to display light of a specified color, such as green, to indicate successful loading. FIG. 49 shows an example of a GUI that may be used by the user to select either the guided or expert setup mode. A graphical representation of the injector head, along with its coupling to the hand controller, is displayed. Different lights and lighting patterns may be used once setup is initiated.

FIG. 48 shows one example of a GUI that may be provided on the console during initial setup of the injector in the guided and/or express mode. A graphical representation of various components of the injection head is shown within the GUI, such as the fluid reservoirs, the syringes, and the various different valve/air detector assemblies. The icon and light color coding that is used with the graphical representation indicates that saline has been loaded from the saline reservoir into the syringe. Contextual lighting patterns on the injection head may also be used in conjunction with the instructions on the GUI during this initial setup. If the user has selected the guided setup mode, the system would display on the GUI the next setup step, or instruction, after the saline has been successfully loaded. By using various forms of visual indicators within the GUI (such as, for example, graphical symbols or textual instructions), the system is capable of indicating to a user which specific setup function, or functions, are to be performed on corresponding components of the system. In one embodiment, graphical symbols such as arrows or even colored highlighting may be used within the GUI. The graphical symbols may be displayed in various different colors. In a guided setup mode, the GUI may provide a series of visual indicators or instructions to provide the user with detailed setup instructions for the system.

FIG. 50 shows an example of a GUI that may be provided during a guided setup procedure, according to one embodiment. In this example, the GUI provides instructions to the user for setting up the contrast syringe. The GUT provides a graphical representation of the contrast syringe loaded in the injector head, along with representation of input and output tubing. The input tubing, as shown, runs through a valve and an air detector. The textual instructions within the GUI indicate that the user is to open the contrast syringe chamber, place the syringe within the chamber, and then close the chamber. The combination of graphical and textual information within the GUI provides the user with multiple forms of useful information during the setup process.

Figure 51:
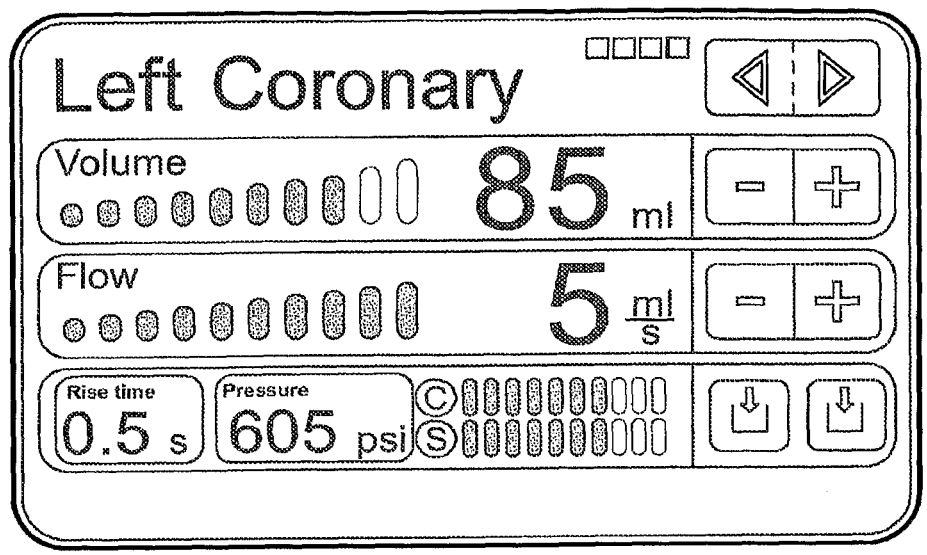

FIG. 51 through FIG. 54 provide examples of graphical information that may be displayed within a small control panel, such as the panel 608 and 708. FIG. 51 shows an example of a screen that may be provided within a GUI to display details and parameters for a left coronary injection procedure. The user may modify the maximum volume of medical fluid to be delivered during the procedure, along with the maximum flow rate, using the "+" and "−" buttons. In one embodiment, these buttons are hard-buttons provided on the housing of the control panel. In one embodiment, these buttons are provided within a touch-screen panel. FIG. 51 also displays the rise time and calculated or measured fluid pressure, as well as bar indicators for the amount of fluid remaining in the contrast and saline fluid reservoirs. When a user is not located in proximity to the main control panel, the user may find information displayed on the small control panel (located on the injector head) to be of particular use and convenience.

Figure 52:
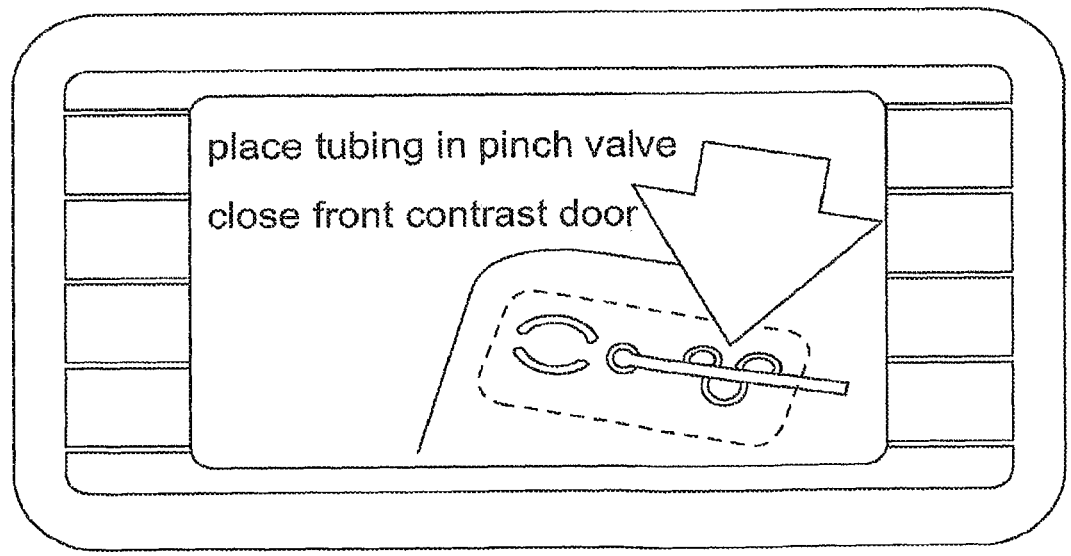

FIG. 52 provides another example of setup information that may be provided within a GUI. As shown, this particular example provides information pertinent to a guided setup process. The textual information instructs a user to place tubing through a valve and to close the door. The graphical information shows a representation of the tubing placed through the valve, with an arrow pointing to the valve for identification by the user.

Figure 53:
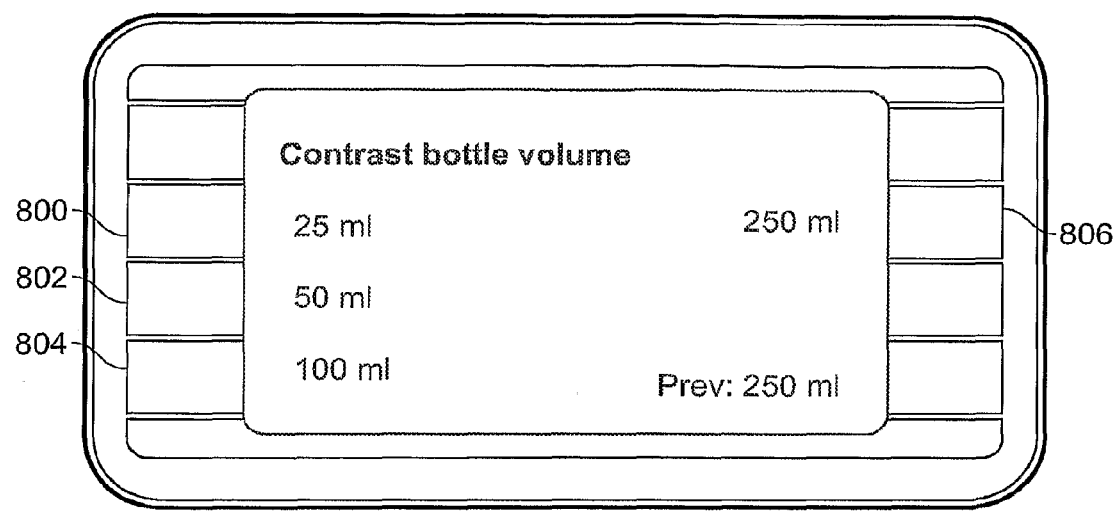

FIG. 53 provides an example of a bottle selection screen. Through interaction with the GUI, the user may select the contrast bottle volume, or size, that is to be used, according to one embodiment. As shown FIG. 53, the user may select from the displayed options by a touching button 800, 802, 804, or 806. The volume, or size, of the previous contrast reservoir that was used is also displayed in the GUI. In one embodiment, the buttons 800, 802, 804, and 806 are hard buttons. In one embodiment, the buttons 800, 802, 804, and 806 are buttons that are selectable on a touch-screen.

Figure 54:
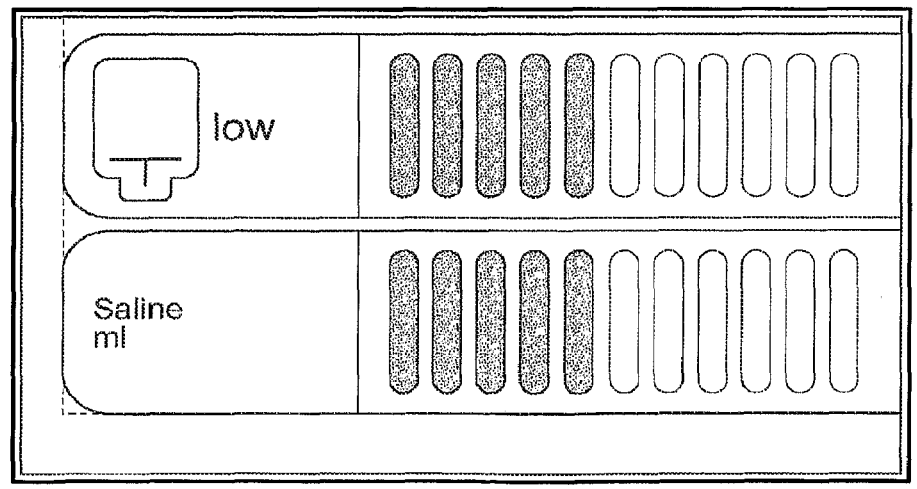

FIG. 54 provides an example of a warning that may be displayed to the user. For example, this warning may be provided on the screen display shown in FIG. 51 on a small control panel. This particular warning indicates that a fluid reservoir is running low on fluid. An icon, or graphical representation, is displayed next to the corresponding bar indicator. In FIG. 54, the warning indicates that the contrast reservoir is low. When a user sees this warning, the user is aware the replacement may be imminently required. A separate warning or error indicator may be displayed when the contrast reservoir is actually empty.

Various screens may be displayed on a remote, small display or control panel. This remote panel may communicate with the main panel using a wireless connection, according to one embodiment. In one embodiment, the remote panel is portable and small, such as the size of a PDA (personal digital assistant). The screen size of the remote panel may be smaller than that of the main panel, according to one embodiment, but may still be capable of providing a large amount of display information to a user, including information in a plurality of different colors. The user may also be able to input information using the remote panel, according to one embodiment, that is then transmitted back to the main panel.

Figure 55A:
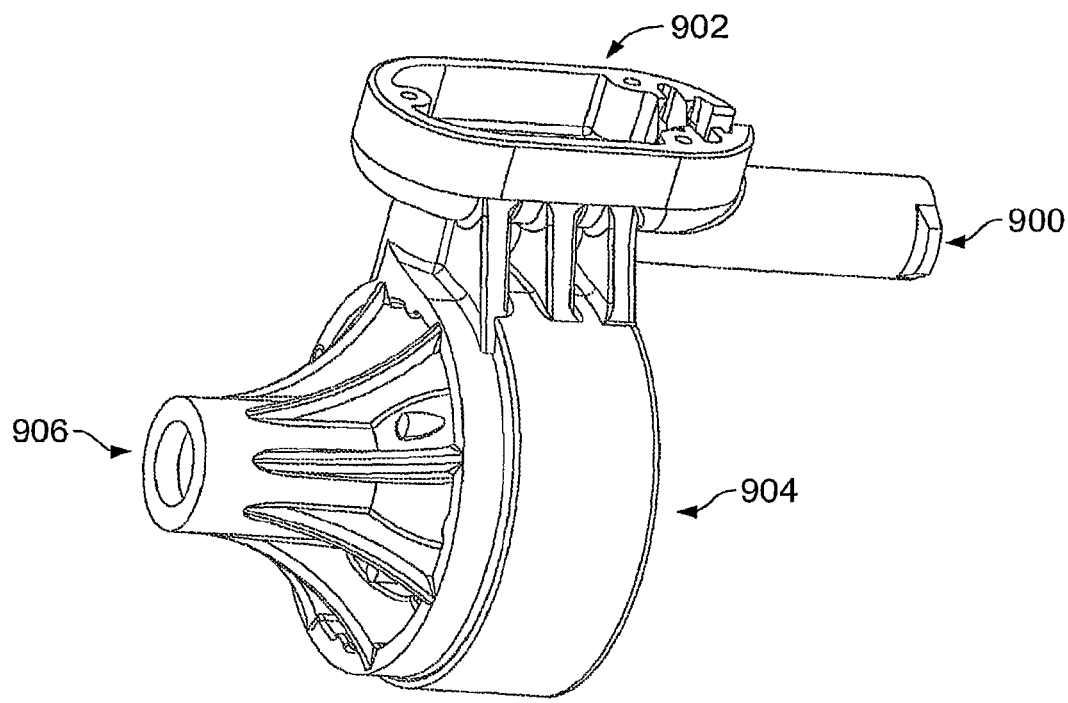
FIG. 55A is a perspective view of one embodiment of a valve that may be used with a powered injection system.

FIG. 55A is a perspective view of one embodiment of a valve that may be used with a powered injection system. For example, the valve may be used with the system 600 shown in FIG. 39A or in the system 700 shown in FIG. 42, according to one embodiment. In one embodiment, the valve comprises an elastomeric valve assembly that is part of a patient line, single-use kit. The valve as shown in FIG. 55A includes a first input port 900, a second input port 904, a transducer connection 902, and an output port 906. The transducer connection 902 may be coupled to a pressure transducer for use in monitoring hemodynamics. The pressure transducer may then be coupled to a hemodynamic monitoring system. The input port 900 may be connected to a first fluid output line, such as the output tubing 618b shown in FIG. 39A. In one embodiment, the input port 900 is coupled to a low-pressure line. The input port 904 may be connected to a second fluid output line, such as the output tubing 618a. In one embodiment, the input port 904 is coupled to a high-pressure line. The output port 906 is coupled to a patient line that leads to a catheter. Fluid is expelled out of the port 906 and injected into a patient in this embodiment. In one embodiment, the valve functions as a one-way valve that allows fluid to flow from either port 900 or 904 to port 906, but not in the opposite direction. In one embodiment, the valve may be capable of providing bi-directional fluid flow.

Figure 55B:
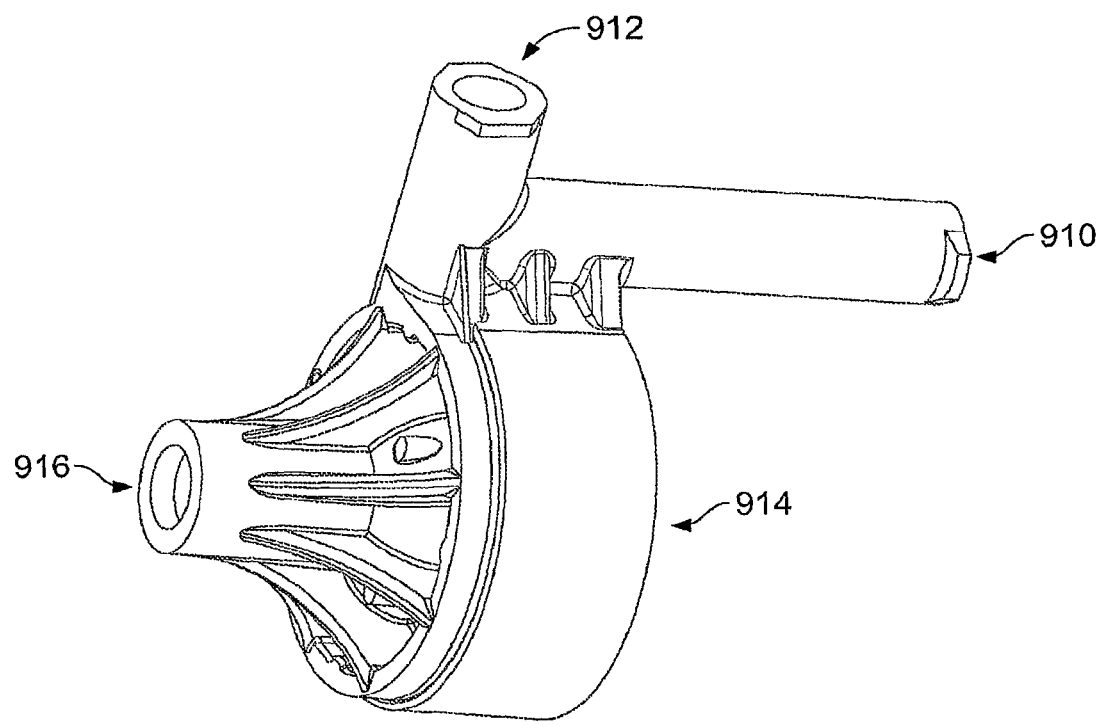
FIG. 55B is a perspective view of another embodiment of a valve that may be used with a powered injection system.

FIG. 55B is a perspective view of another embodiment of a valve that may be used with a powered injection system, such as the system 600 or system 700. In this embodiment, the valve comprises a first input port 910, a second input port 914, an output port 916, and a vent 912. The valve shown in FIG. 55B does not include a transducer connection, but instead includes a vent 912.

Figure 56:
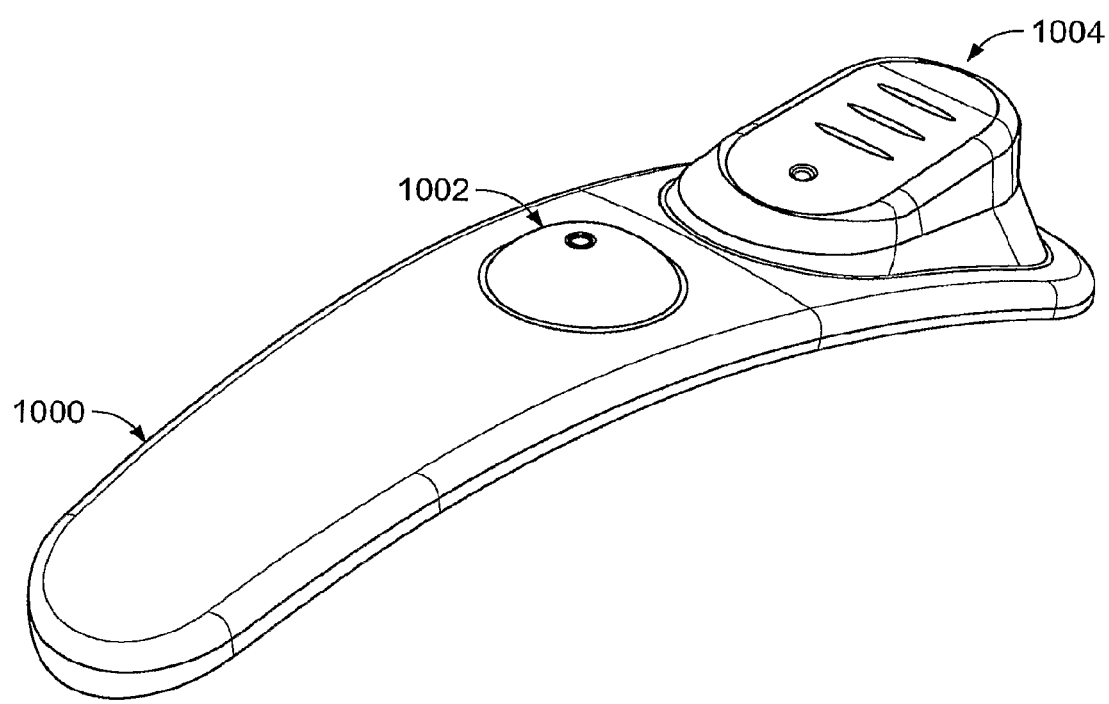
FIG. 56 is a perspective view of one embodiment of a hand controller that may be used with a powered injection system.

FIG. 56 is a perspective view of one embodiment of a hand controller that may be used with a powered injection system, such as the system 600 or system 700. This hand controller may be coupled to the system and used by a user to control the injection of fluid into a patient. In one embodiment, the hand controller is a disposable component that is discarded after each patient procedure. In one embodiment, the hand controller is reusable across multiple procedures.

The hand controller comprises a housing 1000, a first button 1002, and a second button 1004. As shown, the housing 1000 is ergonomic, thin, and may fit well into a palm of a user's hand. In one embodiment, the housing 1000 is made of a plastic material, and the buttons 1002 and 1004 are made of a flexible material, such as silicone or rubber. The user may press the button 1002 to inject a first fluid into the patient, such as saline. The user may press the button 1004 to inject a second fluid into the patient, such as contrast. In one mode, the user may press the button 1002 to inject a predetermined amount of fluid. In one mode, the user may press the button 1004 to inject a variable amount of fluid at a variable flow rate, depending on how long and how hard the user presses the button 1004. In one embodiment, the user may use the same finger, such as a thumb, to press either the button 1002 or the button 1004. In one embodiment, the user may press the buttons 1002 and 1004 at the same, or substantially the same, time using different fingers. In one embodiment, the hand controller and corresponding buttons are coupled to the injection system using a pneumatic interface or electronic interface. In other embodiments, other interfaces may be used. In one embodiment, the hand controller shown in FIG. 56 may replace the hand controller 14 shown in FIG. 1.

It will be appreciated that while preferred embodiment descriptions and applications of the invention have been disclosed, other modifications not specifically disclosed or referred to herein will be apparent to those skilled in the art in light of the foregoing description. This description is intended to provide specific examples of preferred embodiments, structures, methods, algorithms and applications. Accordingly, the invention is not limited to any particular embodiment or configuration or component parts thereof.

What is claimed is:

1. A disposable fluid connector to be used with a powered injector that injects medical fluid into a patient, the disposable fluid connector comprising:
    a first single-use tubing component having proximal and distal ends, the proximal end of the first single-use tubing component to be operatively coupled to an output of a first re-usable syringe of the powered injector, and the distal end of the first single-use tubing component to be operatively coupled to a patient line;
    a second single-use tubing component having proximal and distal ends, the proximal end of the second single-use tubing component to be operatively coupled to an output of a second re-usable syringe of the powered injector, and the distal end of the second single-use tubing component to be operatively coupled to the patient line, wherein the first single-use tubing component and the second single-use tubing component are each usable only for a single patient procedure, and wherein the first re-usable syringe and the second re-usable syringe are each reusable for multiple patient procedures; and
    a connection comprising an electrical connector that is configured to electrically connect the connection to both the powered injector and to an external medical device,
    wherein when the connection is electrically connected to the powered injector and electrically connected to the external medical device, the connection is configured to electrically connect the external medical device to the powered injector, and
    wherein the disposable fluid connector comprises a disposable cassette including a portion that is non-removably attached to both the first single-use tubing component and the second single-use tubing component, such that the disposable fluid connector is loadable and unloadable as one assembly into the powered injector.

2. The disposable fluid connector of claim 1, wherein:
    the proximal end of the first single-use tubing component, when connected to the powered injector, is coupled to first re-usable tubing that is coupled an output port of the first syringe; and
    the proximal end of the second single-use tubing component, when connected to the powered injector, is coupled to second re-usable tubing that is coupled to an output port of the second syringe.

3. The disposable fluid connector of claim 2, wherein:
    the distal end of the first single-use tubing component is coupled to a first input port of a fluid valve;

the distal end of the second single-use tubing component is coupled to a second input port of the fluid valve; and an output port of the fluid valve is coupled to the patient line.

4. The disposable fluid connector of claim 3, wherein the fluid valve is an elastomeric valve.

* * * * *